United States Patent
Okamoto et al.

(10) Patent No.: US 10,539,583 B2
(45) Date of Patent: *Jan. 21, 2020

(54) SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

(71) Applicant: PHC HOLDINGS CORPORATION, Tokyo (JP)

(72) Inventors: Fusatoshi Okamoto, Ehime (JP); Masahiro Johno, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 158 days.

This patent is subject to a terminal disclaimer.

(21) Appl. No.: 15/535,345

(22) PCT Filed: Dec. 11, 2015

(86) PCT No.: PCT/JP2015/084738
§ 371 (c)(1),
(2) Date: Jun. 12, 2017

(87) PCT Pub. No.: WO2016/093332
PCT Pub. Date: Jun. 16, 2016

(65) Prior Publication Data
US 2017/0350910 A1 Dec. 7, 2017

(30) Foreign Application Priority Data
Dec. 12, 2014 (JP) ................................ 2014-251903

(51) Int. Cl.
*G01N 35/00* (2006.01)
*G01N 35/08* (2006.01)
*G01N 37/00* (2006.01)

(52) U.S. Cl.
CPC . *G01N 35/00069* (2013.01); *G01N 35/00584* (2013.01); *G01N 35/08* (2013.01); *G01N 37/00* (2013.01); *G01N 2035/00495* (2013.01)

(58) Field of Classification Search
CPC ......... G01N 35/00069; G01N 35/1016; G01N 35/0098; G01N 35/00584; G01N 35/08;
(Continued)

(56) References Cited

U.S. PATENT DOCUMENTS

| 4,495,295 A | 1/1985 | Neurath |
| 4,673,653 A | 6/1987 | Guigan |

(Continued)

FOREIGN PATENT DOCUMENTS

| EP | 0326100 A2 | 8/1989 |
| EP | 0724156 A1 | 7/1996 |

(Continued)

OTHER PUBLICATIONS

Extended European Search Report issued in European Patent Application No. 15866519.0, dated Jun. 19, 2018.
(Continued)

*Primary Examiner* — Michael L Hobbs
(74) *Attorney, Agent, or Firm* — McDermott Will & Emery LLP

(57) ABSTRACT

A substrate for sample analysis including: a substrate including a rotation axis; a first chamber, which includes a first space which retains the liquid; a second chamber, which includes a second space which retains the liquid discharged from the first chamber; and a first flow passage, which includes a path connecting the first chamber and the second chamber in which the first flow passage has a first opening and a second opening, the first opening and the second opening are connected to the first chamber and the second chamber, respectively, and the first opening is positioned on
(Continued)

a side closer to the rotation axis than the second opening, in which the first space includes a first region, which includes a portion extending from the first opening and in which the first space of the first chamber has a capacity larger than a capacity of the first flow passage.

22 Claims, 23 Drawing Sheets

(58) Field of Classification Search
CPC ............... G01N 35/00; G01N 37/00; G01N 2035/00495; B01L 3/50273; B01L 2200/0668; B01L 2200/0621; B01L 2300/0867; B01L 2300/0864; B01L 2300/0806; B01L 2400/0457; B01L 2400/0409; B01L 2400/0406; B01L 2400/043

See application file for complete search history.

(56) References Cited

U.S. PATENT DOCUMENTS

| | | | |
|---|---|---|---|
| 4,745,077 A | 5/1988 | Holian et al. | |
| 4,916,081 A | 4/1990 | Kamada et al. | |
| 4,918,025 A | 4/1990 | Grenner | |
| 4,990,075 A | 2/1991 | Wogoman | |
| 5,160,702 A * | 11/1992 | Kopf-Sill | B01L 3/502753 422/72 |
| 5,173,262 A | 12/1992 | Burtis et al. | |
| 5,466,574 A | 11/1995 | Liberti et al. | |
| 5,627,041 A | 5/1997 | Shartle | |
| 5,741,714 A | 4/1998 | Liberti | |
| 5,912,134 A | 6/1999 | Shartle | |
| 6,063,589 A | 5/2000 | Kellogg et al. | |
| 6,103,537 A | 8/2000 | Ullman et al. | |
| 6,238,538 B1 | 5/2001 | Parce et al. | |
| 6,274,384 B1 | 8/2001 | Starzl et al. | |
| 6,458,553 B1 | 10/2002 | Colin et al. | |
| 6,551,841 B1 | 4/2003 | Wilding et al. | |
| 7,476,543 B2 | 1/2009 | Becker et al. | |
| 7,867,753 B2 | 1/2011 | Andersson | |
| 7,897,398 B2 | 3/2011 | Saiki | |
| 8,058,010 B2 | 11/2011 | Erickson et al. | |
| 8,415,140 B2 | 4/2013 | Saiki et al. | |
| 8,703,070 B1 | 4/2014 | Parng et al. | |
| 8,956,879 B2 | 2/2015 | Tanaka et al. | |
| 2002/0019059 A1 | 2/2002 | Chow et al. | |
| 2002/0071788 A1 | 6/2002 | Fujii et al. | |
| 2002/0119482 A1 | 8/2002 | Nelson et al. | |
| 2002/0137218 A1 * | 9/2002 | Mian | B29C 59/14 436/45 |
| 2002/0151078 A1 | 10/2002 | Kellogg et al. | |
| 2002/0180975 A1 | 12/2002 | Ogura et al. | |
| 2003/0026740 A1 | 2/2003 | Staats | |
| 2003/0077204 A1 | 4/2003 | Seki et al. | |
| 2003/0138819 A1 | 7/2003 | Gong et al. | |
| 2003/0211010 A1 | 11/2003 | Nagaoka et al. | |
| 2004/0089616 A1 | 5/2004 | Kellogg et al. | |
| 2004/0137607 A1 | 7/2004 | Tanaami et al. | |
| 2004/0181343 A1 | 9/2004 | Wigstrom et al. | |
| 2005/0079634 A1 | 4/2005 | Wilding et al. | |
| 2005/0123447 A1 | 6/2005 | Koike et al. | |
| 2005/0178218 A1 | 8/2005 | Montagu | |
| 2005/0221281 A1 | 10/2005 | Ho | |
| 2005/0287577 A1 | 12/2005 | Yamamichi | |
| 2006/0061760 A1 | 3/2006 | Matsumoto et al. | |
| 2006/0263242 A1 | 11/2006 | Yang et al. | |
| 2006/0292641 A1 | 12/2006 | Nakanishi et al. | |
| 2007/0141576 A1 | 6/2007 | Koide | |
| 2007/0160979 A1 | 7/2007 | Andersson | |
| 2007/0166721 A1 | 7/2007 | Phan et al. | |
| 2007/0189927 A1 | 8/2007 | Ballhom et al. | |
| 2007/0218566 A1 | 9/2007 | Barten et al. | |
| 2007/0224304 A1 | 9/2007 | Kunimatsu et al. | |
| 2007/0243111 A1 | 10/2007 | Momose | |
| 2007/0266777 A1 | 11/2007 | Bergman et al. | |
| 2008/0035579 A1 | 2/2008 | Lee et al. | |
| 2008/0073546 A1 | 3/2008 | Andersson et al. | |
| 2008/0102537 A1 | 5/2008 | Harding et al. | |
| 2008/0131978 A1 | 6/2008 | Fujimura et al. | |
| 2008/0138831 A1 | 6/2008 | Hataoka | |
| 2008/0156079 A1 | 7/2008 | Momose | |
| 2008/0171400 A1 | 7/2008 | Cho et al. | |
| 2008/0176272 A1 | 7/2008 | Bergman et al. | |
| 2008/0219891 A1 | 9/2008 | McDevitt et al. | |
| 2008/0240996 A1 | 10/2008 | Harding et al. | |
| 2008/0242556 A1 | 10/2008 | Cao et al. | |
| 2009/0042317 A1 | 2/2009 | Ikeda | |
| 2009/0053108 A1 | 2/2009 | Cho et al. | |
| 2009/0111190 A1 | 4/2009 | Andersson et al. | |
| 2009/0123337 A1 | 5/2009 | Noda et al. | |
| 2009/0126516 A1 | 5/2009 | Yamamoto et al. | |
| 2009/0155125 A1 | 6/2009 | Michiue et al. | |
| 2009/0169430 A1 | 7/2009 | Yamamoto et al. | |
| 2009/0253130 A1 | 10/2009 | Yoo | |
| 2009/0317896 A1 | 12/2009 | Yoo | |
| 2010/0071486 A1 | 3/2010 | Kim et al. | |
| 2010/0074801 A1 | 3/2010 | Saiki | |
| 2010/0078322 A1 | 4/2010 | Yamanishi et al. | |
| 2010/0132820 A1 | 6/2010 | Ozaki et al. | |
| 2010/0151560 A1 | 6/2010 | Wo et al. | |
| 2010/0159600 A1 | 6/2010 | Shin et al. | |
| 2010/0184228 A1 | 7/2010 | Saiki | |
| 2010/0221741 A1 | 9/2010 | Saiki et al. | |
| 2010/0255589 A1 | 10/2010 | Saiki et al. | |
| 2010/0262389 A1 | 10/2010 | Nakanishi et al. | |
| 2010/0281961 A1 | 11/2010 | Saiki et al. | |
| 2010/0290955 A1 | 11/2010 | Cho et al. | |
| 2011/0045505 A1 | 2/2011 | Warthoe et al. | |
| 2011/0058985 A1 | 3/2011 | Saiki et al. | |
| 2011/0117665 A1 | 5/2011 | Saiki et al. | |
| 2011/0124128 A1 | 5/2011 | Oosterbroek et al. | |
| 2011/0126646 A1 | 6/2011 | Saiki et al. | |
| 2011/0250695 A1 | 10/2011 | Sarofim et al. | |
| 2012/0024083 A1 | 2/2012 | Wo et al. | |
| 2012/0135533 A1 | 5/2012 | Shikida et al. | |
| 2012/0244607 A1 | 9/2012 | Iwamoto et al. | |
| 2012/0261256 A1 | 10/2012 | Chang et al. | |
| 2012/0269701 A1 | 10/2012 | Linder et al. | |
| 2012/0275971 A1 | 11/2012 | Momose | |
| 2012/0322683 A1 | 12/2012 | Liu et al. | |
| 2013/0029361 A1 | 1/2013 | Hamachi et al. | |
| 2013/0074962 A1 | 3/2013 | Garcia da Fonseca et al. | |
| 2013/0142697 A1 | 6/2013 | Kim et al. | |
| 2013/0164763 A1 | 6/2013 | Saiki et al. | |
| 2013/0206701 A1 | 8/2013 | Strohmeier et al. | |
| 2013/0260481 A1 | 10/2013 | Shimizu et al. | |
| 2013/0261010 A1 | 10/2013 | Bailey et al. | |
| 2013/0266956 A1 | 10/2013 | Tia et al. | |
| 2013/0288351 A1 | 10/2013 | Nitta | |
| 2014/0004505 A1 | 1/2014 | Su et al. | |
| 2014/0073041 A1 | 3/2014 | Kijima | |
| 2014/0234184 A1 | 8/2014 | Oshika et al. | |
| 2014/0242721 A1 | 8/2014 | Kellogg et al. | |
| 2014/0270459 A1 | 9/2014 | Moll et al. | |
| 2014/0273192 A1 | 9/2014 | Sharpe et al. | |
| 2015/0087544 A1 | 3/2015 | Putnam et al. | |
| 2015/0093771 A1 | 4/2015 | Griss et al. | |
| 2015/0098864 A1 | 4/2015 | Yang | |
| 2015/0111778 A1 | 4/2015 | McDevitt et al. | |
| 2015/0251183 A1 | 9/2015 | Saiki | |
| 2015/0355132 A1 | 12/2015 | Crooks et al. | |
| 2017/0131304 A1 * | 5/2017 | Johno | G01N 35/00069 |
| 2017/0131305 A1 * | 5/2017 | Okamoto | G01N 35/00069 |
| 2017/0138972 A1 | 5/2017 | Johno et al. | |
| 2017/0168046 A1 | 6/2017 | Saiki et al. | |
| 2017/0350910 A1 | 12/2017 | Okamoto et al. | |

FOREIGN PATENT DOCUMENTS

| | | |
|---|---|---|
| EP | 0871539 A1 | 10/1998 |
| EP | 1105457 A1 | 6/2001 |
| EP | 2072134 A2 | 6/2009 |

(56) References Cited

FOREIGN PATENT DOCUMENTS

| | | |
|---|---|---|
| EP | 2133150 A1 | 12/2009 |
| EP | 2 175 278 A1 | 4/2010 |
| EP | 2253958 A1 | 11/2010 |
| EP | 2311565 A1 | 4/2011 |
| EP | 2402460 A1 | 1/2012 |
| EP | 2602025 A1 | 6/2013 |
| JP | S60-159651 A | 8/1985 |
| JP | S61-264263 A | 11/1986 |
| JP | H01-227061 A | 9/1989 |
| JP | H05-297001 A | 11/1993 |
| JP | H05-322894 A | 12/1993 |
| JP | H07-500910 A | 1/1995 |
| JP | H08-262024 A | 10/1996 |
| JP | H09-218201 A | 8/1997 |
| JP | H09-257796 A | 10/1997 |
| JP | H09-325148 A | 12/1997 |
| JP | H10-300752 A | 11/1998 |
| JP | 2001-502793 A | 2/2001 |
| JP | 2002-236131 A | 8/2002 |
| JP | 2003-043052 A | 2/2003 |
| JP | 2004-163104 A | 6/2004 |
| JP | 2005-010031 A | 1/2005 |
| JP | 2005-345160 A | 12/2005 |
| JP | 2006-010535 A | 1/2006 |
| JP | 2006-068384 A | 3/2006 |
| JP | 2006-112824 A | 4/2006 |
| JP | 2006-177850 A | 7/2006 |
| JP | 2006-258696 A | 9/2006 |
| JP | 2007-003361 A | 1/2007 |
| JP | 2007-003414 A | 1/2007 |
| JP | 2007-010341 A | 1/2007 |
| JP | 2007-024851 A | 2/2007 |
| JP | 2007-047031 A | 2/2007 |
| JP | 2007-064742 A | 3/2007 |
| JP | 2007-071557 A | 3/2007 |
| JP | 2007-071655 A | 3/2007 |
| JP | 2007-078676 A | 3/2007 |
| JP | 2007-101240 A | 4/2007 |
| JP | 2007/279069 A | 10/2007 |
| JP | 2007-285792 A | 11/2007 |
| JP | 2007-530938 A | 11/2007 |
| JP | 2007-315879 A | 12/2007 |
| JP | 2008-064701 A | 3/2008 |
| JP | 2008-064748 A | 3/2008 |
| JP | 2008-128906 A | 6/2008 |
| JP | 2008-134126 A | 6/2008 |
| JP | 2008-15708 A | 7/2008 |
| JP | 2008-164360 A | 7/2008 |
| JP | 2008-164434 A | 7/2008 |
| JP | 2008/216237 A | 9/2008 |
| JP | 2009-014529 A | 1/2009 |
| JP | 2009-031116 A | 2/2009 |
| JP | 2009-042104 A | 2/2009 |
| JP | 2009-109251 A | 5/2009 |
| JP | 2009-121860 A | 6/2009 |
| JP | 2009-128342 A | 6/2009 |
| JP | 2009/133831 A | 6/2009 |
| JP | 2009-139289 A | 6/2009 |
| JP | 2009-156717 A | 7/2009 |
| JP | 2009-156778 A | 7/2009 |
| JP | 2009-162701 A | 7/2009 |
| JP | 2009-180688 A | 8/2009 |
| JP | 2009-180697 A | 8/2009 |
| JP | 2009-186296 A | 8/2009 |
| JP | 2009-210564 A | 9/2009 |
| JP | 2009/287971 A | 12/2009 |
| JP | 2010/071644 A | 4/2010 |
| JP | 2010-122022 A | 6/2010 |
| JP | 2010-151447 A | 7/2010 |
| JP | 2010-210531 A | 9/2010 |
| JP | 2010-243373 A | 10/2010 |
| JP | 2010-286297 A | 12/2010 |
| JP | 2011-007778 A | 1/2011 |
| JP | 2011-069618 A | 4/2011 |
| JP | 2011-183589 A | 9/2011 |
| JP | 2011-196849 A | 10/2011 |
| JP | 2012-143204 A | 8/2012 |
| JP | 2012-159325 A | 8/2012 |
| JP | 2012-215515 A | 11/2012 |
| JP | 2012-229985 A | 11/2012 |
| JP | 2013-050435 A | 3/2013 |
| JP | 2013-079812 A | 5/2013 |
| JP | 2013-205305 A | 10/2013 |
| JP | 2014-032018 A | 2/2014 |
| JP | 2014-044077 A | 3/2014 |
| JP | 2014-048209 A | 3/2014 |
| JP | 2014-106207 A | 6/2014 |
| JP | 2014-190906 A | 10/2014 |
| JP | 2014-232023 A | 12/2014 |
| JP | 2015-121493 A | 7/2015 |
| JP | 2015-197338 A | 11/2015 |
| JP | 2015-223562 A | 12/2015 |
| WO | 90/013016 A1 | 11/1990 |
| WO | 90/015321 A2 | 12/1990 |
| WO | 92/016844 A1 | 10/1992 |
| WO | 93/08893 A1 | 5/1993 |
| WO | 96/026011 A1 | 8/1996 |
| WO | 98/13684 A | 4/1998 |
| WO | 1999/064836 A1 | 12/1999 |
| WO | 01/087485 A2 | 11/2001 |
| WO | 02/23163 A1 | 3/2002 |
| WO | 05/075997 A1 | 8/2005 |
| WO | 2007/005077 A1 | 1/2007 |
| WO | 2007/105584 A1 | 9/2007 |
| WO | 2007/116909 A1 | 10/2007 |
| WO | 07/122943 A1 | 11/2007 |
| WO | 2008/053743 A1 | 5/2008 |
| WO | 2008/139697 A1 | 11/2008 |
| WO | 2010/044598 A2 | 4/2010 |
| WO | 10/058303 A1 | 5/2010 |
| WO | 2010/077159 A1 | 7/2010 |
| WO | 2012/164552 A1 | 12/2012 |
| WO | 2014/017018 A1 | 1/2014 |

OTHER PUBLICATIONS

International Search Report issued in International Patent Application No. PCT/JP2015/084738, dated Mar. 15, 2016; with English translation.
International Search Report issued in corresponding International Patent Application No. PCT/JP2015/068729, dated Sep. 1, 2015; with English translation.
International Search Report issued in corresponding International Patent Application No. PCT/JP2015/068724, dated Sep. 1, 2015; with English translation.
International Search Report issued in corresponding International Patent Application No. PCT/JP2015/068723, dated Sep. 29, 2015; with English translation.
International Search Report issued in corresponding International Patent Application No. PCT/JP2015/068722, dated Sep. 29, 2015; with English translation.
Chinese Search Report issued in corresponding Chinese Patent Application No. 201580035558.6, dated Dec. 15, 2017; with partial English translation.
Extended European Search Report dated Dec. 21, 2017, issued in counterpart European Patent Application No. 15814780.1.
Non-Final Office Action issued in related U.S. Appl. No. 15/323,007, dated Jan. 4, 2019.
Non-Final Office Action issued in related U.S. Appl. No. 15/323,001, dated Jun. 3, 2019.
Final Office Action issued in related U.S. Appl. No. 15/323,007, dated May 16, 2019.
Notice of Allowance issued in related U.S. Appl. No. 15/322,977, dated Sep. 11, 2019.
Notice of Allowance issued in related U.S. Appl. No. 15/322,910, dated Feb. 25, 2019.

* cited by examiner

SUBSTRATE FOR SAMPLE ANALYSIS, SAMPLE ANALYSIS DEVICE, SAMPLE ANALYSIS SYSTEM, AND PROGRAM FOR SAMPLE ANALYSIS SYSTEM

RELATED APPLICATIONS

This application is the U.S. National Phase under 35 U.S.C. § 371 of International Patent Application No. PCT/JP2015/084738, filed on Dec. 11, 2015, which in turn claims the benefit of Japanese Application No. 2014-251903, filed on Dec. 12, 2014, the disclosures of which Applications are incorporated by reference herein.

TECHNICAL FIELD

The present application relates to a substrate for sample analysis, a sample analysis device, a sample analysis system, and a program for a sample analysis system.

BACKGROUND ART

There has hitherto been known a technology using a substrate for sample analysis in order to analyze a specific component in a specimen such as urine or blood. For example, in Patent Document No. 1, there is disclosed a technology using a disc-shaped substrate for sample analysis having flow passages, chambers, and the like formed therein. The disclosed technology involves rotation of the disc-shaped substrate for sample analysis to perform transportation, distribution, and mixing of solutions, analysis of a component in a specimen solution, and the like.

CITATION LIST

Patent Literature

Patent Document No. 1: Japanese Patent Application Laid-Open Publication No. 7-500910

SUMMARY OF INVENTION

Technical Problem

As analysis of a specific component in a specimen, there is given an analysis method including complicated reaction steps, using an enzyme reaction, an immune reaction, and the like. There has been a demand for a technology capable of performing such analysis method including complicated reaction steps in a substrate for sample analysis.

Non-limiting and illustrative embodiments of the present application provide a substrate for sample analysis, a sample analysis device, a sample analysis system, and a program for a sample analysis system, which are adaptable to an analysis method involving analysis of a component in a specimen through more complicated reaction steps.

Solution to Problem

A substrate for sample analysis according to this disclosure is a substrate for sample analysis, which involves transportation of a liquid through rotational motion, the substrate for sample analysis including: a substrate including a rotation axis; a first chamber, which is positioned in the substrate and includes a first space configured to retain the liquid; a second chamber, which is positioned in the substrate and includes a second space configured to retain the liquid discharged from the first chamber; and a first flow passage, which is positioned in the substrate, includes a path configured to connect the first chamber and the second chamber to each other, and is capable of being filled with the liquid retained in the first space through a capillary phenomenon, in which the first flow passage has a first opening and a second opening, the first opening and the second opening are connected to the first chamber and the second chamber, respectively, and the first opening is positioned on a side closer to the rotation axis than the second opening, in which the first space includes a first region, which is connected to the first opening and includes a portion extending from the first opening toward a side farther from the rotation axis, and in which the first space of the first chamber has a capacity larger than a capacity of the first flow passage.

Advantageous Effects of Invention

A substrate for sample analysis, a sample analysis device, a sample analysis system, and a program for a sample analysis system according to one embodiment of the present application are adaptable to an analysis method involving analysis of a component in a specimen through complicated reaction steps.

DESCRIPTION OF EMBODIMENTS

In an analysis method for a component in a specimen such as urine or blood, a binding reaction of an analyte, which is an object to be analyzed, and a ligand that specifically binds to the analyte is used in some cases. As such analysis method, there are given, for example, immunoassay and genetic diagnosis.

As an example of the immunoassay, there are given a competitive method and a non-competitive method (sandwich immunoassay method). Further, as an example of the genetic diagnosis, there is given a gene detection method using hybridization. In the immunoassay and the gene detection method, for example, magnetized particles (sometimes referred to as "magnetized beads", "magnetic particles", "magnetic beads", or the like) are used. As an example of those analysis methods, the sandwich immunoassay method using magnetized particles is specifically described.

Figure 1:
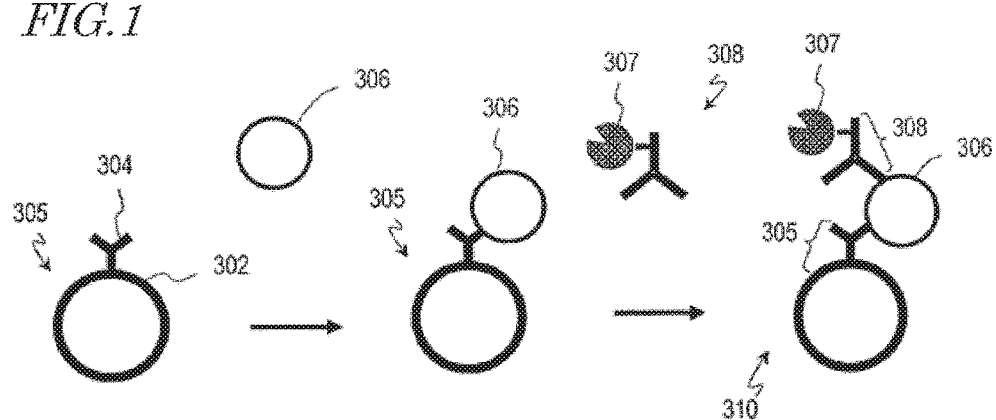
FIG. 1 is an exemplary schematic view for illustrating a sandwich immunoassay method using magnetized particles.

As illustrated in FIG. 1, first, a primary antibody 304 immobilized onto a surface of a magnetized particle 302 (hereinafter referred to as "magnetized particle immobilized antibody 305") and an antigen 306, which is an object to be measured, are caused to bind to each other by an antigen-antibody reaction. Next, a secondary antibody having a labeling substance 307 bound thereto (hereinafter referred to as "labeled antibody 308") and the antigen 306 are caused to bind to each other by the antigen-antibody reaction. With this, a complex 310 in which the magnetized particle immobilized antibody 305 and the labeled antibody 308 are bound to the antigen 306 is obtained.

Signals based on the labeling substance 307 of the labeled antibody 308 bound in the complex 310 are detected, and an antigen concentration is measured in accordance with an amount of the detected signals. As the labeling substance 307, there are given, for example, an enzyme (for example, peroxidase, alkaline phosphatase, luciferase, or the like), a chemiluminescent substance, an electrochemiluminescent substance, a fluorescent substance, and the like. Signals such as a dye, luminescence, fluorescence, and the like in accordance with each labeling substance 307 are detected.

In the above-mentioned series of reactions, in order to obtain the complex 310, which is a reaction product, it is necessary to separate an unreacted substance in a specimen, a substance that non-specifically adsorbs to the magnetized particle and the like, and an unreacted substance, for example, the labeled antibody 308 that has not been involved in formation of the complex 310. This separation is called bound/free separation (B/F separation). In the immunoassay using a competitive method and the gene detection method using hybridization, the step of the B/F separation is similarly required.

In the foregoing, the sandwich immunoassay method using magnetized particles is described as an example. However, the B/F separation is required when the immunoassay using a competitive method or a non-competitive method and the gene detection method using hybridization are performed, regardless of whether or not the magnetized particles are used. As the case of not using the magnetized particles, there are given, for example, the case of using a ligand immobilized onto a solid phase made of a material, for example, polystyrene or polycarbonate, through physical adsorption, the case of using a ligand immobilized onto a solid phase through chemical bonding, the case of using a ligand immobilized onto a surface of a metal substrate made of gold or the like (for example, immobilized through use of a self-assembled monolayer (SAM)), and the like.

In order to satisfactorily perform the B/F separation, it is preferred that the complex 310 including the magnetized particle be washed with a washing liquid a plurality of times. Specifically, first, in a reaction solution containing the complex 310, the unreacted antigen 306, the labeled antibody 308, and the like, only the reaction solution is removed under a state in which the complex 310 including the magnetized particle is trapped with a magnet. After that, a washing liquid is added to wash the complex 310. Then, the washing liquid is removed. This washing is repeated a plurality of times so that the B/F separation which satisfactorily removes the unreacted substance and the non-specific adsorbing substance may be achieved. In this respect, description is also given by way of an example using the magnetized particles. However, the same holds true for the general sandwich-type assay, regardless of whether or not the magnetized particles are used.

The above-mentioned operation of performing washing a plurality of times has hitherto been manually performed by an operator through use of an analysis instrument, or achieved through use of large analysis equipment having a complicated mechanism. Therefore, there has been a demand for a technology of performing washing a plurality of times more simply.

The inventors of the present application have made detailed investigations on a technology enabling the washing step to be performed a plurality of times through use of the substrate for sample analysis as disclosed in Patent Document No. 1. As a result, the inventors have conceived a substrate for sample analysis, a sample analysis device, a sample analysis system, and a program for a sample analysis system, which are novel. The substrate for sample analysis, the sample analysis device, the sample analysis system, and the program for sample analysis system according to one embodiment of the present application are described below.

[Item 1]

A substrate for sample analysis, which involves transportation of a liquid through rotational motion, the substrate for sample analysis including:

a substrate including a rotation axis;

a first chamber, which is positioned in the substrate and includes a first space configured to retain the liquid;

a second chamber, which is positioned in the substrate and includes a second space configured to retain the liquid discharged from the first chamber; and a first flow passage, which is positioned in the substrate, includes a path configured to connect the first chamber and the second chamber to each other, and is capable of being filled with the liquid retained in the first space through a capillary phenomenon, in which the first flow passage has a first opening and a second opening, the first opening and the second opening are connected to the first chamber and the second chamber, respectively, and the first opening is positioned on a side closer to the rotation axis than the second opening, in which the first space includes a first region, which is connected to the first opening and includes a portion extending from the first opening toward a side farther from the rotation axis, and in which the first space of the first chamber has a capacity larger than a capacity of the first flow passage.

[Item 2]

The substrate for sample analysis according to Item 1, in which the first space further includes a second region connected to the extending portion of the first region at a position farther from the rotation axis than the first opening.

[Item 3]

The substrate for sample analysis according to Item 1, in which a part of the first chamber and a part of the first flow passage are positioned in a radial direction with the rotation axis being a center with the first opening interposed therebetween.

[Item 4]

The substrate for sample analysis according to Item 1 or 2, in which the first flow passage includes a first portion having the first opening and a second portion having the second opening, and in which the second portion has a capillary force larger than a capillary force of the first portion.

[Item 5]

The substrate for sample analysis according to Item 4, in which the substrate has a substrate shape having a predetermined thickness, and the second portion has a thickness smaller than a thickness of the first portion in a direction of the predetermined thickness.

[Item 6]

The substrate for sample analysis according to Item 4 or 5, in which the first flow passage is adjacent to the first portion and further includes a space positioned on the rotation axis side from the first portion and an opening communicating to the space, and in which the space is free from being a capillary path.

[Item 7]

The substrate for sample analysis according to any one of Items 1 to 6, in which the first region of the first space includes a connecting portion connected to the first opening, and the connecting portion is capable of sucking the liquid retained in the first space through the capillary phenomenon, and in which the connecting portion has an opening larger than the first opening in the first region.

[Item 8]

The substrate for sample analysis according to Item 7, in which the connecting portion has a thickness smaller than a thickness of the first region in the direction of the predetermined thickness.

[Item 9]

The substrate for sample analysis according to Item 2, in which the extending portion of the first region is capable of sucking the liquid retained in the second region through the capillary phenomenon.

[Item 10]

The substrate for sample analysis according to any one of Items 1 to 9, in which the first space of the first chamber has a capacity that is twice or more of a capacity of the first flow passage.

[Item 11]

The substrate for sample analysis according to any one of Items 1 to 10, further including:

a third chamber, which is positioned farther from the rotation axis than the second chamber in the substrate and includes a third space configured to retain the liquid discharged from the second chamber; and a second flow passage, which is positioned in the substrate, includes a path configured to connect the second chamber and the third chamber to each other, and is capable of being filled with the liquid retained in the second space through the capillary phenomenon.

[Item 12]

The substrate for sample analysis according to Item 11, further including:

a fourth chamber, which is positioned in the substrate and includes a fourth space configured to retain the liquid; and another flow passage, which is positioned in the substrate, includes a path configured to connect the fourth chamber and the second chamber to each other, and is capable of being filled with the liquid retained in the fourth space through the capillary phenomenon.

[Item 13]

The substrate for sample analysis according to Item 12, in which the first chamber and the fourth chamber are arranged in two regions divided by a straight line connecting a vicinity of a center of the second chamber and the rotation axis to each other in the substrate, respectively.

[Item 14]

The substrate for sample analysis according to Item 12, in which both the first chamber and the fourth chamber are arranged in one of two regions divided by a straight line connecting a vicinity of a center of the second chamber and the rotation axis to each other in the substrate.

[Item 15]

The substrate for sample analysis according to any one of Items 1 to 14, further including a magnet positioned adjacent to the second chamber.

[Item 16]

A sample analysis system, including:

the substrate for sample analysis of any one of Items 1 to 15; and a sample analysis device including:

a motor, which is configured to rotate the substrate for sample analysis about the rotation axis under a state in which the rotation axis is held at an angle of more than 0° and 90° or less with respect to a gravity direction;

a rotation angle detection circuit, which is configured to detect a rotation angle of a rotation axis of the motor;

a drive circuit, which is configured to control the rotation angle of the motor at a time of rotation and stoppage based on a detection result of the rotation angle detection circuit; and a control circuit, which includes a computing unit, a memory, and a program stored in the memory and configured to be executable by the computing unit, and which is configured to control operations of the motor, the rotation angle detection circuit, and the drive circuit based on the program, in which, when the substrate for sample analysis having the first chamber filled with the liquid is mounted to the sample analysis device, the program executes the steps of:

(a) stopping the substrate for sample analysis at a predetermined first angle, to thereby fill the first flow passage with a part of the liquid of the first chamber through the capillary phenomenon; and (b) rotating the substrate for sample analysis, to thereby transport the part of the liquid in the first flow passage to the second chamber.

[Item 17]

The sample analysis system according to Item 16, in which the substrate for sample analysis includes the substrate for sample analysis of Item 11, and in which, after the step (b), the program executes the steps of:

(c) stopping the substrate for sample analysis at a predetermined second angle, to thereby fill the second flow passage with the part of the liquid transported to the second chamber through the capillary phenomenon; and (d) rotating the substrate for sample analysis, to thereby cause the liquid transported to the second chamber to move to the third chamber through the second flow passage with a centrifugal force.

[Item 18]

The sample analysis system according to Item 17, in which, after the step (d), the program executes the steps of:

(e) stopping the substrate for sample analysis at a predetermined third angle, to thereby fill the first flow passage with another part of the liquid in the first chamber through the capillary phenomenon; and (f) rotating the substrate for sample analysis, to thereby transport the another part of the liquid in the first flow passage to the second chamber.

[Item 19]

The sample analysis system according to Item 18, in which, after the step (f), the program executes the steps of:

(g) stopping the substrate for sample analysis at a predetermined fourth angle, to thereby fill the second flow passage with the another part of the liquid transported to the second chamber through the capillary phenomenon; and (h) rotating the substrate for sample analysis, to thereby cause the another part of the liquid transported to the second chamber to move to the third chamber through the second flow passage with the centrifugal force.

[Item 20]

The sample analysis system according to Item 19, in which, after the step (h), the program executes the steps of:

(i) stopping the substrate for sample analysis at a predetermined fifth angle, to thereby fill the another flow passage with a part of the liquid in the fourth chamber through the capillary phenomenon; and (j) rotating the substrate for sample analysis, to thereby transport the part of the liquid to the second chamber.

[Item 21]

The sample analysis system according to Item 20, in which the sample analysis device further includes an optical measurement unit, and in which, after the step (j), the program executes the step of (k) causing the optical measurement unit to perform optical measurement of the liquid transported to the second chamber.

[Item 22]

The sample analysis system according to Item 16, in which the program executes the steps (a) and (b) repeatedly twice or more.

[Item 23]

A sample analysis device, including:

a motor, which is configured to rotate the substrate for sample analysis of any one of Items 1 to 15 about the rotation axis under a state in which the rotation axis is held at an angle of more than 0° and 90° or less with respect to a gravity direction;

a rotation angle detection circuit, which is configured to detect a rotation angle of a rotation axis of the motor;

a drive circuit, which is configured to control the rotation angle of the motor at a time of rotation and stoppage based on a detection result of the rotation angle detection circuit; and a control circuit, which includes a computing unit, a memory, and a program stored in the memory and configured to be executable by the computing unit, and which is configured to control operations of the motor, the rotation angle detection circuit, and the drive circuit based on the program, in which, when the substrate for sample analysis having the first chamber filled with the liquid is mounted to the sample analysis device, the program executes the steps of:

(a) stopping the substrate for sample analysis at a predetermined first angle, to thereby fill the first flow passage with a part of the liquid in the first chamber through the capillary phenomenon; and (b) rotating the substrate for sample analysis, to thereby transport the part of the liquid in the first flow passage to the second chamber.

[Item 24]

A program for a sample analysis system, the sample analysis system including:

the substrate for sample analysis of any one of Items 1 to 15; and a sample analysis device including:

a motor, which is configured to rotate the substrate for sample analysis about the rotation axis under a state in which the rotation axis is held at an angle of more than 0° and 90° or less with respect to a gravity direction;

a rotation angle detection circuit, which is configured to detect a rotation angle of a rotation axis of the motor;

a drive circuit, which is configured to control the rotation angle of the motor at a time of rotation and stoppage based on a detection result of the rotation angle detection circuit; and a control circuit, which includes a computing unit, a memory, and a program stored in the memory and configured to be executable by the computing unit, and which is configured to control operations of the motor, the rotation angle detection circuit, and the drive circuit based on the program, in which, when the substrate for sample analysis having the first chamber filled with the liquid is mounted to the sample analysis device, the program executes the steps of:

(a) stopping the substrate for sample analysis at a predetermined first angle, to thereby fill the first flow passage with a part of the liquid in the first chamber through the capillary phenomenon; and (b) rotating the substrate for sample analysis, to thereby transport the part of the liquid in the first flow passage to the second chamber.

Now, with reference to the drawings, detailed description is made of the substrate for sample analysis, the sample analysis device, the sample analysis system, and the program for a sample analysis system according to this embodiment. In the substrate for sample analysis, the sample analysis device, the sample analysis system, and the program for a sample analysis system according to this embodiment, a liquid retained in one chamber can be weighed in a predetermined amount and transported to another chamber in divided portions. In this embodiment, the liquid is exemplified by a washing liquid. However, the liquid is not limited to the washing liquid and may be various liquids used in sample analysis.

First Embodiment

Figure 2A:
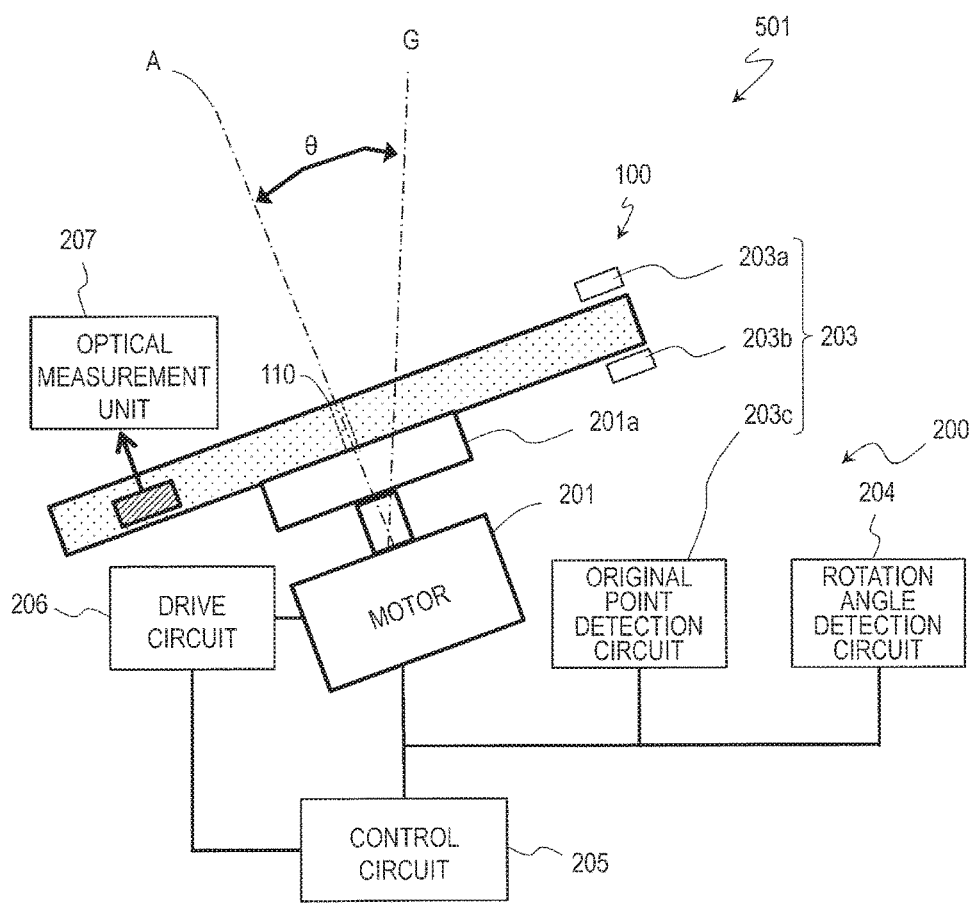
FIG. 2A is a schematic view for illustrating an example of a configuration of a sample analysis system according to an embodiment.

FIG. 2A is a schematic view for illustrating an entire configuration of a sample analysis system 501. The sample analysis system 501 includes a substrate 100 for sample analysis and a sample analysis device 200.

Configuration of Sample Analysis Device 200

The sample analysis device 200 includes a motor 201, an original point detector 203, a rotation angle detection circuit 204, a control circuit 205, a drive circuit 206, and an optical measurement unit 207.

The motor 201 includes a turntable 201a and a rotation axis A inclined from a gravity (vertical) direction G at an angle θ of more than 0° and 90° or less with respect to the gravity direction and is configured to rotate the substrate 100 for sample analysis mounted to the turntable 201a about the rotation axis A. The rotation axis A is inclined, and hence the movement caused by gravity as well as the centrifugal force caused by rotation can be used for transporting a liquid in the substrate 100 for sample analysis. The inclination angle of the rotation axis A with respect to the gravity direction G is preferably 5° or more, more preferably 10° or more and 45° or less, still more preferably 20° or more and 30° or less. The motor 201 may be, for example, a DC motor, a brushless motor, an ultrasonic motor, or the like.

Figure 2B:
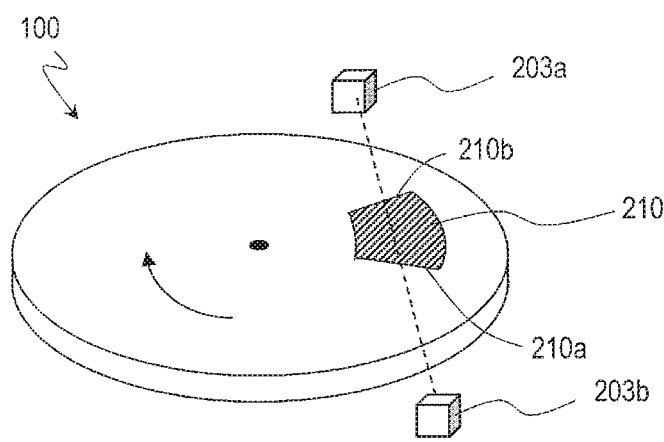
FIG. 2B is a schematic view for illustrating an example of a configuration for detecting an original point of a substrate for sample analysis in the sample analysis system.

The original point detector 203 is configured to detect an original point of the substrate 100 for sample analysis mounted to the motor 201. For example, as illustrated in FIG. 2A, the original point detector 203 includes a light source 203a, a light receiving element 203b, and an original point detection circuit 203c, and is arranged so that the substrate 100 for sample analysis is positioned between the light source 203a and the light receiving element 203b. For example, the light source 203a is a light-emitting diode, and the light receiving element 203b is a photodiode. As illustrated in FIG. 2B, the substrate 100 for sample analysis includes a marker 210 formed at a certain position. The marker 210 has, for example, a light blocking property of blocking at least a part of light emitted from the light source 203a. In the substrate 100 for sample analysis, a region of the marker 210 has a small transmittance (for example, 10% or less), and a region other than the marker 210 has a large transmittance (for example, 60% or more).

When the substrate 100 for sample analysis is rotated by the motor 201, the light receiving element 203b outputs a detection signal in accordance with a light amount of incident light to the original point detection circuit 203c. The detection signal increases or decreases at an edge 210a and an edge 210b of the marker 210 depending on a rotation direction. The original point detection circuit 203c is configured to detect a decrease in detected light amount and output the detection as an original point signal, for example, when the substrate 100 for sample analysis is rotated clockwise as represented by the arrow of FIG. 2B. The position of the edge 210a of the marker 210 is herein defined as an original point position of the substrate 100 for sample analysis (reference angle position of the substrate 100 for sample analysis). However, a certain angle position which is suitably determined based on the position of the edge 210a of the marker 210 may be defined as an original point. Further, when the marker 210 has a fan shape, and the center angle thereof is smaller than detection accuracy of an angle required for sample analysis, the marker 210 itself may be defined as the original point position.

The original point position is used for the sample analysis device 200 to obtain information on the rotation angle of the substrate 100 for sample analysis. The original point detector 203 may have another configuration. For example, the substrate 100 for sample analysis may include a magnet for detecting an original point, and the original point detector 203 may be a magnetism detection element configured to detect magnetism of the magnet. Further, a magnet configured to trap magnetized particles described later may be used for detecting an original point. Further, when the substrate 100 for sample analysis can be mounted to the turntable 201a only at a certain angle, the original point detector 203 may be omitted.

The rotation angle detection circuit 204 is configured to detect a rotation angle of the rotation axis A of the motor 201. The rotation angle detection circuit 204 may be, for example, a rotary encoder mounted to the rotation axis A. When the motor 201 is a brushless motor, the rotation angle detection circuit 204 may include a Hall element, which is arranged in the brushless motor, and a detection circuit, which is configured to receive an output signal from the Hall element and output an angle of the rotation axis A.

The drive circuit 206 is configured to rotate the motor 201. Specifically, the drive circuit 206 is configured to rotate the substrate 100 for sample analysis in a clockwise direction or in a counterclockwise direction based on an instruction from the control circuit 205. Further, the drive circuit 206 is configured to stop swing and rotation of the substrate 100 for sample analysis in accordance with detection results of the rotation angle detection circuit 204 and the original point detector 203 based on an instruction from the control circuit 205.

The optical measurement unit 207 is configured to detect signals (for example, a dye, luminescence, fluorescence, and the like) in accordance with the labeling substance 307 of the labeling antibody 308 bound in the complex 310 (FIG. 1) held by the substrate 100 for sample analysis.

The control circuit 205 includes, for example, a CPU arranged in the sample analysis device 200. The control circuit 205 is configured to execute a computer program read into a random access memory (RAM; not shown), thereby transmitting commands to other circuits in accordance with a procedure of the computer program. Each of the circuits that receives the command is configured to operate as described herein, thereby realizing functions of each of the circuits. For example, as illustrated in FIG. 2A, the command from the control circuit 205 is transmitted to the drive circuit 206, the rotation angle detection circuit 204, the optical measurement unit 207, and the like. The procedure of the computer program is illustrated in a flowchart of the accompanying drawing.

The RAM into which the computer program is read, that is, the RAM storing the computer program, may be volatile or non-volatile. A volatile RAM is a RAM that cannot hold stored information without supply of electric power. For example, a dynamic random access memory (DRAM) is a typical volatile RAM. A non-volatile RAM is a RAM capable of holding information even without supply of electric power. Examples of the non-volatile RAM include a magneto-resistive RAM (MRAM), a resistive random access memory (ReRAM), and a ferroelectric random access memory (FeRAM). In this embodiment, it is preferred to adopt a non-volatile RAM.

Both the volatile RAM and the non-volatile RAM are examples of a non-transitory computer-readable recording medium. A magnetic recording medium such as a hard disk and an optical recording medium such as an optical disc are also examples of the non-transitory computer-readable recording medium. That is, a computer program according to this disclosure may be recorded on various non-transitory computer-readable media, other than media (transitory media) such as air, which cause the computer program to propagate as a radio signal.

The control circuit 205 is herein described as a component which is separate from the rotation angle detection circuit 204 and the original point detection circuit 203c of the original point detector 203. However, those circuits may be realized with common hardware. For example, the CPU (computer) arranged in the sample analysis device 200 may execute a computer program that serves as the control circuit 205, a computer program that serves as the rotation angle detection circuit 204, and a computer program that serves as the original point detection circuit 203c of the original point detector 203 in series or in parallel. With this, the CPU is allowed to be seemingly operated as a different component.

Substrate 100 for Sample Analysis

Figure 3A:
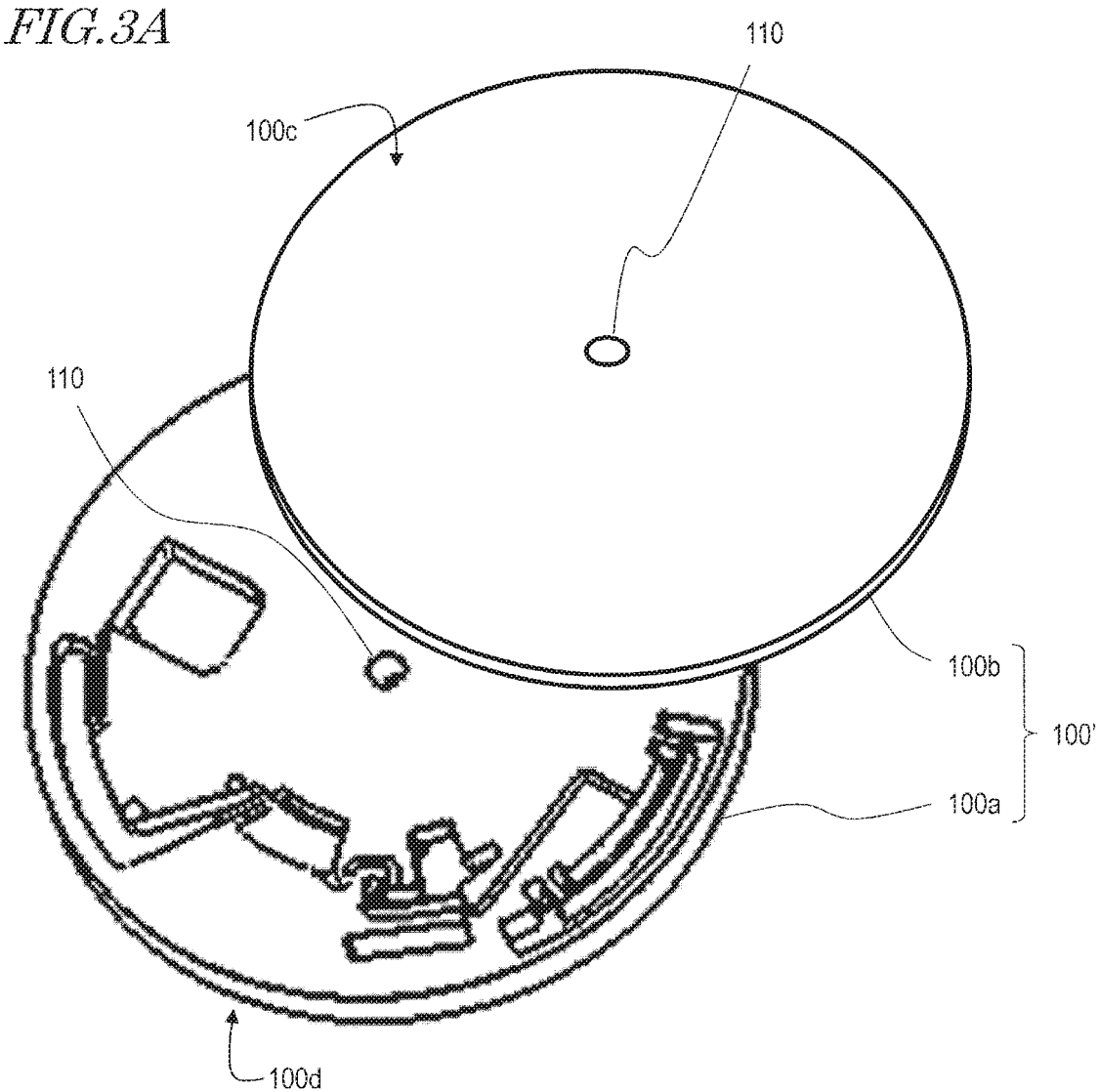
FIG. 3A is an exploded perspective view for illustrating an example of the substrate for sample analysis.

FIG. 3A is an exploded perspective view of the substrate 100 for sample analysis. The substrate 100 for sample analysis includes a rotation axis 110 and a plate-like substrate 100' having a predetermined thickness in a direction parallel to the rotation axis 110. The substrate 100' of the substrate 100 for sample analysis includes a base substrate 100a and a cover substrate 100b. In this embodiment, the substrate 100' of the substrate 100 for sample analysis has a circular shape. However, the substrate 100' may have, for example, a polygonal shape, an oval shape, a fan shape, or the like. The substrate 100' has two principal surfaces 100c and 100d. In this embodiment, the principal surface 100c and the principal surface 100d are parallel to each other, and a thickness of the substrate 100' defined by an interval between the principal surface 100c and the principal surface 100d (distance between the two principal surfaces) is equal at any position of the substrate 100'. However, the principal surfaces 100c and 100d are not always necessary to be parallel to each other. For example, the two principal surfaces may be partially non-parallel or parallel to each other, or may be entirely non-parallel to each other. Further, a recess or a protrusion may be formed on at least one of the principal surfaces 100c and 100d of the substrate 100'.

Figure 3B:
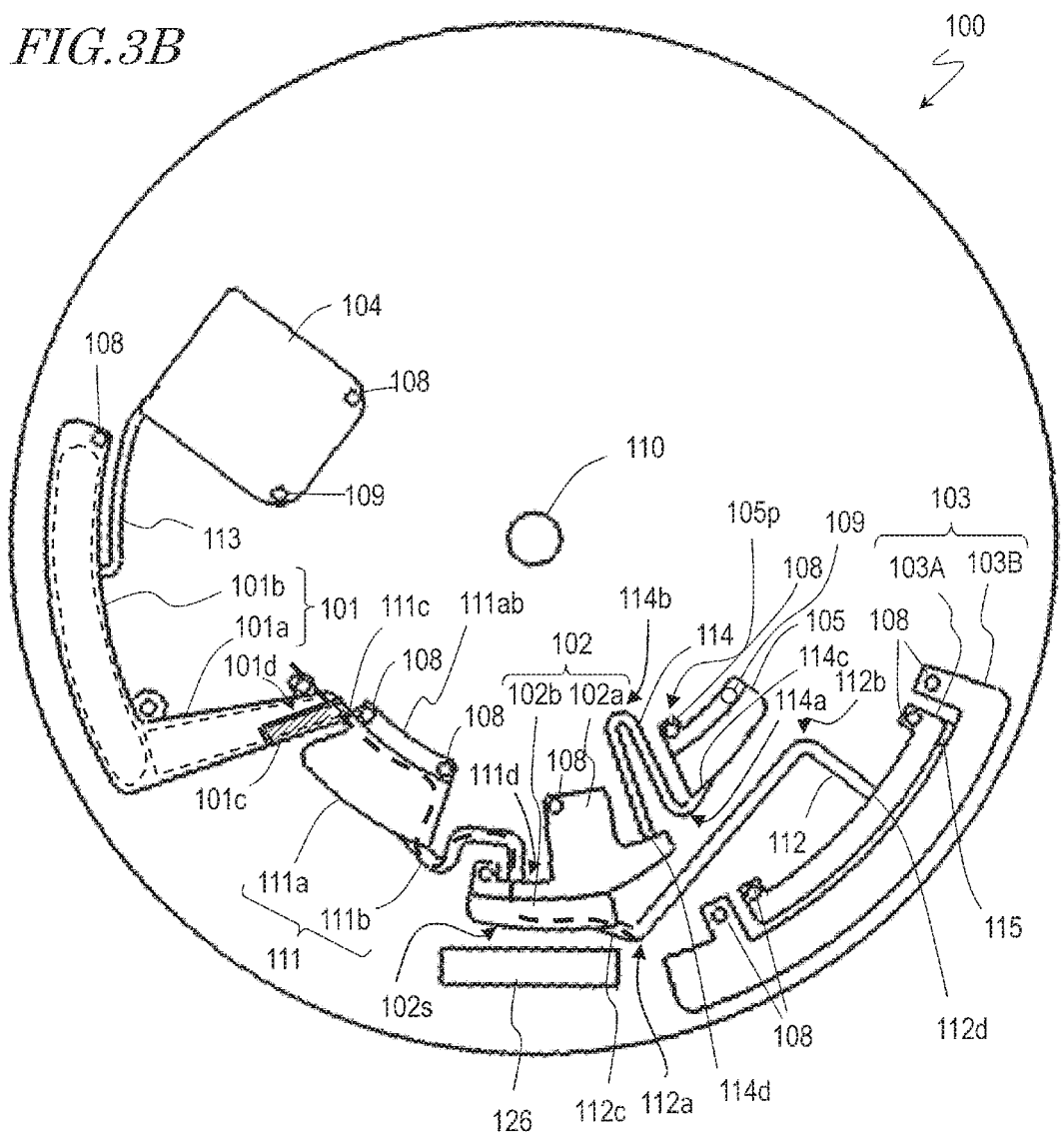
FIG. 3B is a plan view for illustrating an example of the substrate for sample analysis.

FIG. 3B is a plan view of the base substrate 100a. As illustrated in FIG. 3B, the substrate 100 for sample analysis includes a first chamber 101, a second chamber 102, a third chamber 103 (first sub-chamber 103A and second sub-chamber 103B), a storage chamber 104, and a reaction chamber 105, which are positioned in the substrate 100'. The shape of each chamber is not particularly limited unless otherwise stated below, and each chamber may have any suitable shape. Each chamber has a space defined substantially by an upper surface and a lower surface that are parallel to the two principal surfaces 100c and 100d of the substrate 100', and four side surfaces positioned between the upper surface and the lower surface. Two surfaces adjacent to each other of the upper surface, the lower surface, and the side surfaces are not always necessary to be divided by a clear ridge line. The shape of each chamber may be, for example, a flat sphere or a spheroid.

The substrate 100 for sample analysis further includes a first flow passage 111, a second flow passage 112, a third flow passage 113, a fourth flow passage 114, and a fifth flow passage 115, which are positioned in the substrate 100'. The first flow passage 111 is configured to connect the first chamber 101 and the second chamber 102 to each other. The second flow passage 112 is configured to connect the second chamber 102 and the third chamber 103 (first sub-chamber 103A) to each other. The third flow passage 113 is configured to connect the storage chamber 104 and the first chamber 101 to each other. The fourth flow passage 114 is configured to connect the reaction chamber 105 and the second chamber 102 to each other. The fifth flow passage 115 is configured to connect the first sub-chamber 103A and the second sub-chamber 103B to each other.

The transportation of a liquid between the chambers through the flow passage may be realized by various methods. For example, transportation using gravity and transportation using a capillary force and a centrifugal force caused by rotation may be used. Those two transportation methods are generally described below.

For example, as illustrated in FIG. 2A, the substrate 100 for sample analysis is supported with the rotation axis 110 being inclined within a range of more than 0° and 90° or less with respect to the gravity direction G. Then, the rotation angle position of the substrate 100 for sample analysis is changed so that a chamber serving as a transportation origin, in which a liquid is present, is arranged at a position higher than a chamber serving as a transportation destination. The term "higher" as used herein refers to being positioned higher in the gravity direction G. With this, the liquid may be transported to another chamber through use of gravity. In this case, a flow passage connecting the chambers is not a capillary path. The term "capillary path" refers to a flow passage having a narrow space in which at least a part of an inner portion can be filled with the liquid through a capillary phenomenon.

Further, the liquid may also be transported to another chamber through use of the capillary path. The transportation of the liquid through use of the capillary path is described by taking as an example a configuration including a chamber A and a chamber B which are not capillary path spaces, and a capillary path configured to connect the chamber A and the chamber B to each other. When a liquid retained in the chamber A is brought into contact with an opening serving as a connecting portion between the chamber A and the capillary path, the liquid is sucked into the capillary path with a capillary force, and an inner portion of the flow passage is filled with the liquid. However, when the substrate 100 for sample analysis is rotated at a rotation speed (also including a state in which rotation is stopped) at which a centrifugal force equal to or less than a capillary force applied to the liquid in the flow passage can be applied, the liquid in the capillary path is retained in the capillary path space without being transported to the chamber B. In order to fill the inner portion of the capillary path with the liquid through the capillary phenomenon, an air hole (air passage between an external environment and the chamber) is required to be arranged on the chamber B side, that is, on an outlet side of the capillary path. Further, in order to transport the liquid through the capillary phenomenon in a closed space such as the chamber A, the chamber B, and the capillary path, an air hole is required to be arranged also on the chamber A side, that is, an inlet side of the capillary path from the relationship in atmospheric pressure between each of the chambers and the flow passage. Then, in the case where the chamber B is arranged at a position farther from the rotation axis than the chamber A, when the substrate 100 for sample analysis is rotated at a rotation speed at which a centrifugal force larger than a capillary force applied to the liquid in the capillary path can be applied under a state in which the capillary path is filled with the liquid, the liquid in the chamber A can be transported to the chamber B with the centrifugal force.

When the liquid is transported with a capillary force and a centrifugal force caused by rotation, the substrate 100 for sample analysis having a diameter of, for example, 60 mm may be rotated within a range of from 100 rpm to 8,000 rpm. The rotation speed is determined in accordance with the shapes of each of the chambers and each of the flow passages, physical properties of the liquid, timing of transportation and processing of the liquid, and the like.

In this embodiment, each space of the first chamber 101, the second chamber 102, the third chamber 103 (first sub-chamber 103A and second sub-chamber 103B), the storage chamber 104, and the reaction chamber 105 is formed in the base substrate 100a, and the base substrate 100a is covered with the cover substrate 100b, to thereby form an upper portion and a lower portion of each space. That is, those spaces are defined by inner surfaces of the substrate 100'. The first flow passage 111, the second flow passage 112, the third flow passage 113, the fourth flow passage 114, and the fifth flow passage 115 are also formed in the base substrate 100a, and the base substrate 100a is covered with the cover substrate 100b, to thereby form an upper portion and a lower portion of a space of each flow passage. In this embodiment, the base substrate 100a and the cover substrate 100b define an upper surface and a lower surface, respectively. The substrate 100' may be formed of a resin, for example, an acrylic resin, a polycarbonate resin, a polystyrene resin, or the like.

As described with reference to FIG. 1, the reaction chamber 105 is a reaction site in which the magnetized particle immobilized antibody 305, a specimen containing the antigen 306, and the labeling antibody 308 are caused to react with each other to form the complex 310. The shape of the reaction chamber 105 is not particularly limited.

In this embodiment, the reaction chamber 105 is arranged as the reaction site in which the complex 310 is formed. The magnetized particle immobilized antibody 305, the specimen containing the antigen 306, and the labeling antibody 308 may be transported to the reaction chamber 105 in various manners.

For example, a mixed solution in which the magnetized particle immobilized antibody 305, the specimen containing the antigen 306, and the labeling antibody 308 are mixed in advance may be weighed and injected into the substrate 100 for sample analysis, to thereby form the complex in the reaction chamber 105.

The substrate 100 for sample analysis may include, for example, chambers configured to retain the magnetized particle immobilized antibody 305, the specimen containing the antigen 306, and the labeling antibody 308, respectively, and flow passages (for example, capillary paths) by which the chambers and the reaction chamber 105 are connected to each other. In this case, the magnetized particle immobilized antibody 305, the specimen containing the antigen 306, and the labeling antibody 308 may be weighed into each of the chambers, and the magnetized particle immobilized antibody 305, the specimen containing the antigen 306, and the labeling antibody 308 injected into each of the chambers may be transported to the reaction chamber 105 and mixed in the reaction chamber 105, to thereby form the complex 310.

Further, the magnetized particle immobilized antibody 305 and the labeling antibody 308 may be dried (hereinafter referred to as "dried reagent"). In this case, for example, the dried reagent may be retained in the reaction chamber 105, and the dried reagent may be dissolved in a liquid containing a specimen solution containing the antigen 306, to thereby form the complex 310. Further, the dried reagent retained in a certain chamber may be dissolved in a predetermined solution during measurement, and the specimen solution containing the antigen 306 may be mixed therewith in the reaction chamber 105, to thereby form the complex 310.

A solution containing the complex 310 is transported to the second chamber 102 through the fourth flow passage 114.

The storage chamber 104 is configured to store a washing liquid to be used for washing during B/F separation. As described in detail below, in the sample analysis system of this embodiment, the complex 310 may be washed a plurality of times during the B/F separation. Therefore, the storage chamber 104 may retain a total volume of the washing liquid in accordance with the number of times of washing.

The first chamber 101 retains the entire washing liquid stored in the storage chamber 104. Then, in order to wash the complex 310 in the second chamber 102, a part of the washing liquid is transported to the second chamber 102, and a remainder of the liquid is retained. The amount of the washing liquid to be used for one time of washing is weighed with the first flow passage 111 as described below.

Therefore, the first chamber 101 has a capacity equal to or more than that of the first flow passage 111 and has a capacity equal to or more than the total amount of the washing liquid for the number of times of washing (for example, a capacity that is twice or more that of the first flow passage 111 in the case of two times of washing, and a capacity that is three times or more that of the first flow passage 111 in the case of three times of washing).

A space (first space) of the first chamber 101 includes a first region 101a and a second region 101b. The first region 101a is connected to a first opening 111c of the first flow passage 111 described below. The first region 101a includes a portion extending from the first opening 111c toward a side farther from the rotation axis 110. With this, the washing liquid positioned in the first region 101a can be transported to the second chamber 102 through the first flow passage 111. The second region 101b is connected to the first region 101a at a position farther from the rotation axis 110 than the first opening 111c. That is, the second region 101b includes a portion positioned farther from the rotation axis 110 than the first region 101a, and a portion of the second region 101b connected to the first region 101a is positioned farther from the rotation axis 110 than the first region 101a. Further, the washing liquid in an excess amount as compared to the amount to be used for one time of washing can be retained in the second region 101b. In order to transport the washing liquid from the storage chamber 104 to the first chamber 101, at least a part of the second region 101b is positioned farther from the rotation axis 110 than the storage chamber 104.

As described in detail below, in order to cause the washing liquid to move smoothly to the first flow passage 111, the first region 101a includes a connecting portion 101c connected to the first opening 111c. The connecting portion 101c is at least a part of the first region 101a and extends from the first opening 111c to a side farther from the rotation axis 110. The connecting portion 101c is capable of sucking the washing liquid retained in the first chamber 101 through the capillary phenomenon and retaining the washing liquid in the connecting portion 101c. With this, the washing liquid is allowed to move to the first flow passage 111 more reliably. The first chamber 101 excluding the connecting portion 101c is not a space to be filled with a liquid through the capillary phenomenon, but a space in which the liquid can move through the first chamber 101 with gravity.

In this embodiment, as described above, the first chamber 101 includes the first region 101a and the second region 101b. The second region 101b is positioned farther from the rotation axis 110 than the storage chamber 104, and the second region 101b and the storage chamber 104 are connected to each other through the third flow passage 113.

Under a state in which the substrate 100 for sample analysis is stopped at a predetermined angle, the third flow passage 113 is filled with a part of the washing liquid stored in the storage chamber 104 through the capillary phenomenon. When the substrate 100 for sample analysis is rotated under a state in which the third flow passage 113 is filled with the washing liquid, the washing liquid in the storage chamber 104 is transported to the second region 101b through the third flow passage with the centrifugal force caused by rotation. That is, when the first chamber 101 includes the second region 101b positioned farther from the rotation axis 110 than the storage chamber 104, the washing liquid can be transported with the centrifugal force.

In this embodiment, the first chamber 101 having a configuration including the first region 101a and the second region 101b is described, but it is only necessary that the first chamber 101 include the first region 101a. That is, it is only necessary that the first chamber 101 include a portion farther from the rotation axis 110 than the first opening 111c. In this case, it is preferred that a connecting portion between the first chamber 101 and the third flow passage 113 be positioned farther from the rotation axis 110 than a connecting portion between the storage chamber 104 and the third flow passage 113.

The second chamber 102 is a site for performing the B/F separation of the solution containing the complex 310. In order to perform the B/F separation, the substrate 100 for sample analysis includes a magnet 126 arranged in the substrate 100'.

The magnet 126 is positioned close to the space of the second chamber 102 in the substrate 100 for sample analysis. More specifically, the magnet 126 is arranged close to a side surface 102s positioned farthest from the rotation axis 110 among a plurality of side surfaces of the second chamber 102. However, the magnet 126 in the substrate 100 for sample analysis may be arranged at a position close to an upper surface or a lower surface other than the side surface 102s of the second chamber 102. That is, as long as magnetized particles can be trapped onto a wall surface of the second chamber 102 with the magnet 126, the position of the magnet 126 is not particularly limited. The magnet 126 may be configured to be removable depending on the B/F separation, or may be non-removably mounted to the substrate 100', or may be arranged on the sample analysis device 200 side.

When the magnet 126 is configured to be removable, the substrate 100' includes, for example, an accommodating chamber capable of accommodating the magnet 126. For example, as illustrated in FIG. 3E, the substrate 100' may include a recessed accommodating chamber 120 having an opening 120a in the principal surface 100c. The accommodating chamber 120 has a space capable of accommodating the magnet 126. The magnet 126 can be loaded into the substrate 100' by inserting the magnet 126 into the accommodating chamber 120 from the opening 120a. The opening 120a of the accommodating chamber 120 may be arranged on the principal surface 100d or on a side surface positioned between the two principal surfaces 100c and 100d.

When the magnet 126 is arranged on the sample analysis device 200 side, for example, a magnet unit including the magnet 126 may be arranged on the turntable 201a of the sample analysis device 200. In this case, when a user arranges the substrate 100 for sample analysis at a predetermined position of the turntable 201a (magnet unit), the magnet 126 is arranged at a position where magnetized particles can be trapped onto the wall surface of the second chamber 102. As another example of arranging the magnet 126 in the sample analysis device 200, the sample analysis device 200 may include, for example, the magnet 126 and a drive mechanism configured to move the magnet 126. In this case, the substrate 100 for sample analysis may include an accommodating chamber configured to hold the magnet 126, and the drive mechanism may insert the magnet 126 into the accommodating chamber of the substrate 100 for sample analysis and remove the magnet 126 from the accommodating chamber depending on the B/F separation.

When the reaction solution is transported to the second chamber 102 through the fourth flow passage 114, the complex 310 and the unreacted magnetized particle immobilized antibody 305 in the reaction solution (when both the complex 310 and the unreacted magnetized particle immobilized antibody 305 are referred to, both of those are hereinafter simply referred to as "magnetized particles 311") are trapped onto the side surface 102s side with an attractive force (magnetic force) of the magnet 126 arranged close to the side surface 102s.

The reaction solution excluding the magnetized particles 311 is transported to the third chamber 103 through the second flow passage 112. Further, a predetermined amount of the washing liquid is transported from the first flow passage 111 to the second chamber 102, and the trapped magnetized particles 311 are washed in the second chamber 102. The washing liquid is transported to the third chamber 103 through the second flow passage 112. As described in detail below, a space (second space) of the second chamber 102 includes the first region 102a and the second region 102b, and the second region 102b is capable of sucking the reaction solution or the washing liquid retained in the second chamber 102 through the capillary phenomenon and retaining the reaction solution or the washing liquid in the second region 102b. The side surface 102s is positioned in the second region 102b, and the second flow passage 112 is connected to the side surface 102s.

The third chamber 103 is configured to store the reaction solution excluding the magnetized particles 311 and the used washing liquid which are transported from the second chamber 102 through the second flow passage 112. In order to more reliably suppress the return of those liquids to the second chamber 102 due to rotation and/or a change in angle position of the substrate 100 for sample analysis, in this embodiment, the third chamber 103 includes the first sub-chamber 103A and the second sub-chamber 103B. The first sub-chamber 103A and the second sub-chamber 103B are formed of separate independent spaces, and are connected to each other through the fifth flow passage 115. That is, a space (third space) of the third chamber 103 includes a space of the first sub-chamber 103A and a space of the second sub-chamber 103B.

In this embodiment, the second sub-chamber 103B is positioned farther from the rotation axis 110 than the first sub-chamber 103A. Further, the first sub-chamber 103A is positioned farther from the rotation axis 110 than the second chamber 102. That is, the third chamber 103 as a whole is positioned farther from the rotation axis 110 than the second chamber 102. The space of the first sub-chamber 103A has a volume larger than the amount of the reaction solution or the amount of the washing liquid for one time of washing, which is larger. The second sub-chamber 103B has a volume larger than a total amount of the reaction solution and the washing liquid for a plurality of times of washing.

Further, in this embodiment, the third chamber 103 having a configuration including the first sub-chamber 103A and the second sub-chamber 103B is described. However, the second sub-chamber 103B (and the fifth flow passage 115) may be omitted, and the shape of the third chamber 103 is not particularly limited.

Next, each flow passage is described. The first flow passage 111 is configured to transport the washing liquid stored in the first chamber 101 to the second chamber 102. In this case, instead of the total amount of the washing liquid in the first chamber 101, the washing liquid for one time of washing is weighed with the volume of the space defined by the first flow passage 111, and the weighed washing liquid is transported to the second chamber 102. The first flow passage 111 has the first opening 111c and a second opening 111d. The first opening 111c is connected to the first chamber 101, and the second opening 111d is connected to the second chamber 102. More specifically, the first flow passage 111 includes a first portion 111a having the first opening 111c and a second portion 111b having the second opening 111d.

The first portion 111a and the second portion 111b are connected to each other at each one end in which the first opening 111c and the second opening 111d are not positioned.

The first opening 111c is positioned on a side closer to the rotation axis 110 than the second opening 111d. In order to transport a substantially total amount of the liquid in the first flow passage 111 to the second chamber 102, it is preferred that each portion of the first flow passage 111 be positioned at the same place as that of the first opening 111c from the rotation axis 110 or positioned farther from the rotation axis 110 than the first opening 111c. With this, when a centrifugal force stronger than a capillary force applied to the liquid in the first flow passage 111 acts on the washing liquid under a state in which the first flow passage 111 is filled with the washing liquid, the entire washing liquid in the first flow passage 111 is transported to the second chamber 102 without being returned to the first chamber 101.

It is preferred that, among the side surfaces of the second chamber 102, the second opening 111d be formed on an inner peripheral side surface positioned on a side closer to the rotation axis 110 than the space of the second chamber 102 or on a side surface adjacent to the inner peripheral side surface, which is in the vicinity of a connecting position with respect to the inner peripheral side surface. The reason for this is to prevent the washing liquid having been transported to the second chamber 102 from being brought into contact with the second opening 111d to flow reversely to the first flow passage 111.

When a total volume of the first portion 111a and the second portion 111b corresponds to the amount of the washing liquid for one time of washing, and the space between the first opening 111c and the second opening 111d of the first flow passage 111 is filled with the washing liquid, the washing liquid for one time of washing is weighed. Both the first portion 111a and the second portion 111b of the first flow passage 111 can be filled with the washing liquid retained in the first chamber 101 through the capillary phenomenon.

In an example of FIG. 3B, a space 111ab having two air holes 108 is arranged along the rotation axis side of the first portion 111a. The space 111ab is a space configured to secure the air holes 108 and is not a space capable of being filled with a liquid through the capillary phenomenon. For example, when the thickness of the space 111ab is larger than that of the first portion 111a, and the first portion 111a is filled with the liquid through the capillary phenomenon, a capillary force does not substantially act on the space 111ab, and the space 111ab is not filled with the liquid. When air bubbles are generated in the liquid retained in the first portion 111a for some reason, the arrangement of the space 111ab allows the air bubbles to move to the space 111ab, with the result that the air bubbles in the liquid are easily eliminated. With this, when the substrate 100 for sample analysis is rotated, in particular, the air bubbles can be prevented from entering the second portion 111b to hinder the movement of the liquid.

Figure 3C:
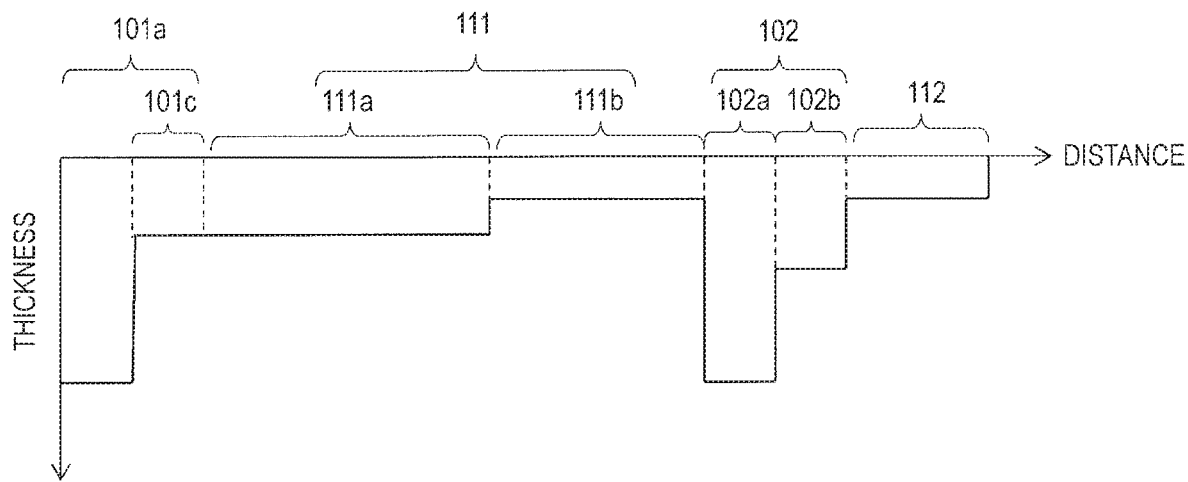
FIG. 3C is a graph for showing an example of thicknesses of chambers and flow passages in a cross section of a thick broken line portion of FIG. 3B.

FIG. 3C is a graph for showing a thickness (depth), in a direction parallel to the thickness of the substrate 100', of a space in a path represented by the thick broken line in FIG. 3B, which extends from the first region 101a of the first chamber 101 to the second flow passage 112 through the first portion 111a and the second portion 111b of the first flow passage 111 and the first region 102a and the second region 102b of the second chamber 102. In FIG. 3C, the horizontal axis represents a distance from one end of the first region 101a, and the vertical axis represents a thickness. In FIG. 3C, the horizontal axis represents an example for illustration, and does not show each distance accurately. Similarly, the vertical axis represents a relative magnitude relationship of thicknesses in adjacent regions, and the value of each thickness is not shown accurately.

As shown in FIG. 3C, in this embodiment, the thickness of the second portion 111b is smaller than that of the first portion 111a in the first flow passage 111, and the second portion 111b has a capillary force larger than that of the first portion 111a. Therefore, when the washing liquid retained in the first region 101a of the first chamber is sucked into the first portion 111a of the first flow passage 111 from the first opening 111c, the washing liquid extends to the second portion 111b on which the larger capillary force acts. With this, the entire first flow passage 111 is filled with the washing liquid.

Further, in the first region 101a of the first chamber 101, the thickness of the connecting portion 101c is smaller than that of any other portion of the first region 101a in FIG. 3C. Further, the thickness of the connecting portion 101c is equal to that of the first portion 111a. With this, a capillary force is also allowed to act on the connecting portion 101c. Further, as illustrated in FIG. 3B, the connecting portion 101c has an opening 101d (represented by the thick line) larger than the first opening 111c and is brought into contact with the remaining portion of the first region 101a at the opening 101d. Therefore, even under a state in which the substrate 100 for sample analysis is stopped at various rotation angles, a part of the opening 101d of the connecting portion 101c is brought into contact with the washing liquid in the first chamber 101, with the result that the connecting portion 101c can suck the washing liquid to be filled with the washing liquid.

The thickness of the connecting portion 101c may be different from that of the first portion 111a. Further, the entire first region 101a of the first chamber 101 may be the connecting portion 101c, or the connecting portion 101c may be omitted. A capillary force of the first portion 111a of the first flow passage 111 is larger than that of the connecting portion 101c. Thus, the washing liquid retained in the connecting portion 101c may be sucked to move to the first portion 111a of the first flow passage 111. Further, the opening 101d of the connecting portion 101c is larger than the first opening 111c of the first flow passage 111. Therefore, the connecting portion 101c serves as a funnel, and a large amount of the washing liquid may be sucked into the first flow passage 111 smoothly through the connecting portion 101c.

The second flow passage 112 includes a third opening 112c and a fourth opening 112d. The third opening 112c is connected to the second chamber 102, and the fourth opening 112d is connected to the first sub-chamber 103A of the third chamber 103.

It is preferred that, among the side surfaces of the second chamber 102, the third opening 112c of the second flow passage 112 be formed on a side surface (outermost peripheral side surface) positioned on a side farthest from the rotation axis 110 or on a side surface adjacent to the outermost peripheral side surface, which is a position including a connecting portion with respect to the outermost peripheral side surface. This is because, when the liquid in the second chamber 102 is transported to the first sub-chamber 103A of the third chamber 103, the occurrence of a residual liquid in the second chamber 102 can be suppressed. FIG. 3B is a view for illustrating a configuration in which the third opening 112c is formed in a part of the outermost peripheral side surface.

The fourth opening 112d of the second flow passage 112 is positioned on a side farther from the rotation axis 110 than the third opening 112c. Further, it is desired that, among side surfaces of the first sub-chamber 103A, the fourth opening 112d be formed on a side surface (innermost peripheral side surface) positioned on a side closest to the rotation axis 110 or on a side surface adjacent to the innermost peripheral side surface, which is a position close to the innermost peripheral side surface. FIG. 3B is a view for illustrating a configuration in which the fourth opening 112d is formed in a part of the innermost peripheral side surface of the first sub-chamber 103A.

The second flow passage 112 can also suck the liquid retained in the second chamber 102 through the capillary phenomenon. As illustrated in FIG. 3C, the thickness of the second flow passage 112 is smaller than that of the second region 102b of the second chamber 102. Further, in the second chamber 102, the second region 102b is smaller than the first region 102a and has a thickness larger than that of the second flow passage 112. Therefore, a capillary force is also allowed to act on the second region 102b, and the washing liquid transported from the first flow passage 111 is sucked into the second region 102b of the second chamber 102 through the capillary phenomenon. The second flow passage 112 is connected to the second region 102b of the second chamber 102. Therefore, a part of the washing liquid is sucked from the second chamber 102 to the second flow passage 112 with a capillary force larger than that of the second region 102b of the second chamber 102.

Inner portions of the third flow passage 113 and the fourth flow passage 114 can also be filled with the liquid through the capillary phenomenon. Specifically, the inner portions of the third flow passage 113 and the fourth flow passage 114 can be filled with the liquid that is filled in the storage chamber 104 and the reaction chamber 105, respectively, through the capillary phenomenon.

The fourth flow passage 114 has a fifth opening 114c and a sixth opening 114d. The fifth opening 114c is connected to the reaction chamber 105, and the sixth opening 114d is connected to the second chamber 102.

It is preferred that, among side surfaces of the reaction chamber 105, the fifth opening 114c of the fourth flow passage 114 be formed on a side surface (outermost peripheral side surface) positioned on a side farthest from the rotation axis 110 or on a side surface adjacent to the outermost peripheral side surface, which is a position including a connecting portion with respect to the outer peripheral side surface. This is because, when the reaction solution in the reaction chamber 105 is transported to the second chamber 102, the occurrence of a residual liquid in the reaction chamber 105 can be suppressed. FIG. 3B is a view for illustrating a configuration in which the fifth opening 114c is formed in a part of the outermost peripheral side surface.

It is preferred that, among the side surfaces of the second chamber 102, the sixth opening 114d be formed on an inner peripheral side surface positioned on a side closer to the rotation axis 110 than the space of the second chamber 102 or on a side surface adjacent to the inner peripheral side surface, which is in the vicinity of a connecting position with respect to the inner peripheral side surface. The reason for this is to prevent the reaction solution having been transported to the second chamber 102 from being brought into contact with the sixth opening 114d to flow reversely to the fourth flow passage 114.

The first flow passage 111 is a space capable of being filled with a liquid through the capillary phenomenon, and hence an inner surface of the substrate 100' defining a flow passage, and an inner surface thereof in the vicinity of a connecting portion of a chamber to which the flow passage is connected may be subjected to hydrophilic treatment. A capillary force significantly acts on those inner surfaces by virtue of the hydrophilic treatment. The hydrophilic treatment can be performed by, for example, applying a non-ionic, cationic, anionic, or zwitterionic surfactant to the above-mentioned inner surfaces, subjecting the inner surfaces to corona discharge treatment, or forming physical fine roughness on the inner surfaces (see, for example, Japanese Patent Application Laid-Open Publication No. 2007-3361). When the second flow passage 112, the third flow passage 113, and the fourth flow passage 114 are spaces in which inner portions thereof can be filled with a liquid through the capillary phenomenon, those flow passages may also be similarly subjected to the hydrophilic treatment.

The second flow passage 112 and the fourth flow passage 114 may further control the movement of a liquid based on the principle of siphon. To this end, as a siphon structure, the second flow passage 112 and the fourth flow passage 114 each have a first bent portion and a second bent portion. Description is given of the second flow passage 112. The second flow passage 112 includes a first bent portion 112a and a second bent portion 112b. The first bent portion 112a has a protruding shape on a side opposite to the rotation axis 110, and the second bent portion 112b has a protruding shape on the rotation axis 110 side. The first bent portion 112a is positioned between the second chamber 102 positioned on a side close to the rotation axis 110, among the second chamber 102 and the third chamber 103 to which the flow passage is connected, and the second bent portion 112b. Similarly, the fourth flow passage 114 includes a first bent portion 114a and a second bent portion 114b. The first bent portion 114a has a protruding shape on a side opposite to the rotation axis 110, and the second bent portion 114b has a protruding shape on the rotation axis 110 side. The first bent portion 114a is positioned between the reaction chamber 105 positioned on a side close to the rotation axis 110, among the reaction chamber 105 and the second chamber 102 to which the flow passage is connected, and the second bent portion 114b.

According to the principle of siphon as used herein, liquid feeding control is performed with a balance between the centrifugal force applied to a liquid caused by rotation of the substrate 100 for sample analysis and the capillary force of the flow passage. Specifically, description is given of an example in which a liquid is transported from the reaction chamber 105 to the second chamber 102, and the liquid is further transported to the third chamber 103.

For example, when the second flow passage 112 is a capillary path not having the siphon structure, during a step in which a liquid is transported from the reaction chamber 105 to the second chamber 102 through the fourth flow passage 114 with a centrifugal force caused by rotation of the substrate 100 for sample analysis, the liquid having been transported to the second chamber 102 is filled into the second flow passage 112 with the capillary force of the second flow passage 112. When the rotation of the substrate 100 for sample analysis continues in this state, the liquid is not retained in the second chamber 102 and is transported to the third chamber 103 through the second flow passage 112. The rotation of the substrate 100 for sample analysis as used herein refers to a rotation speed at which a centrifugal force stronger than the capillary force of the second flow passage 112 can be applied.

Meanwhile, as long as the second flow passage 112 has the siphon structure, the liquid having been transported from the reaction chamber 105 to the second chamber 102 is pulled into the second flow passage 112 with the capillary force of the second flow passage 112. However, when the substrate 100 for sample analysis continues to be rotated at a rotation speed at which a centrifugal force stronger than the capillary force of the second flow passage 112 can be applied, the centrifugal force is stronger than the capillary force applied to the liquid, and hence the second flow passage 112 is not completely filled with the liquid. That is, the second flow passage 112 is filled with the liquid only up to a height that is equal to the distance of a liquid surface of the liquid present in the second chamber 102 with respect to the rotation axis 110.

Further, when the substrate 100 for sample analysis is rotated at a rotation speed (including a state in which rotation is stopped) at which a centrifugal force weaker than the capillary force of the second flow passage 112 is applied, the second flow passage 112 is filled with a liquid with the capillary force, and the liquid does not move any more with the capillary force.

When the liquid in the second chamber 102 is intended to be transported to the third chamber 103, the second flow passage 112 is completely filled with the liquid with the capillary force by rotating the substrate 100 for sample analysis at a rotation speed (also including a state in which rotation is stopped) at which a centrifugal force equal to or less than the capillary force of the second flow passage 112 can be applied. After that, when the substrate 100 for sample analysis is rotated at a rotation speed at which a centrifugal force stronger than the capillary force of the second flow passage 112 can be applied, the liquid in the second chamber 102 can be transported to the third chamber 103.

Thus, when it is intended that the liquid is transported from the reaction chamber 105 to the second chamber 102 at the above-mentioned rotation speed and retained in the second chamber 102 temporarily without being directly transported to the third chamber 103, it is preferred that the second flow passage 112 have the siphon structure.

The same also applies to the fourth flow passage 114. Further, even when the above-mentioned liquid control is not required in the second flow passage 112, the third flow passage 113, and the fourth flow passage 114, a capillary path having the siphon structure may be adopted.

In order to construct the siphon structure, when a distance between the rotation axis 100 and a side surface of a chamber positioned farther from the rotation axis 110, which is closest to the rotation axis 110, is represented by R1, and a distance from the rotation axis 110 to a point of the first bent portion, which is positioned on a side farthest from the rotation axis 110, is represented by R2, it is preferred that R1>R2 (condition 1) be satisfied.

Further, in the case where the rotation axis 110 and the liquid retained in the chamber positioned close to the rotation axis 110 are held while being urged to the side surface due to a centrifugal force, when a distance from the rotation axis 110 to the liquid surface of the liquid is represented by R4, and a distance from the rotation axis 110 to a point of the second bent portion, which is positioned on a side closest to the rotation axis 110, is represented by R3, it is preferred that R4>R3 (condition 2) be satisfied.

Figure 3D:
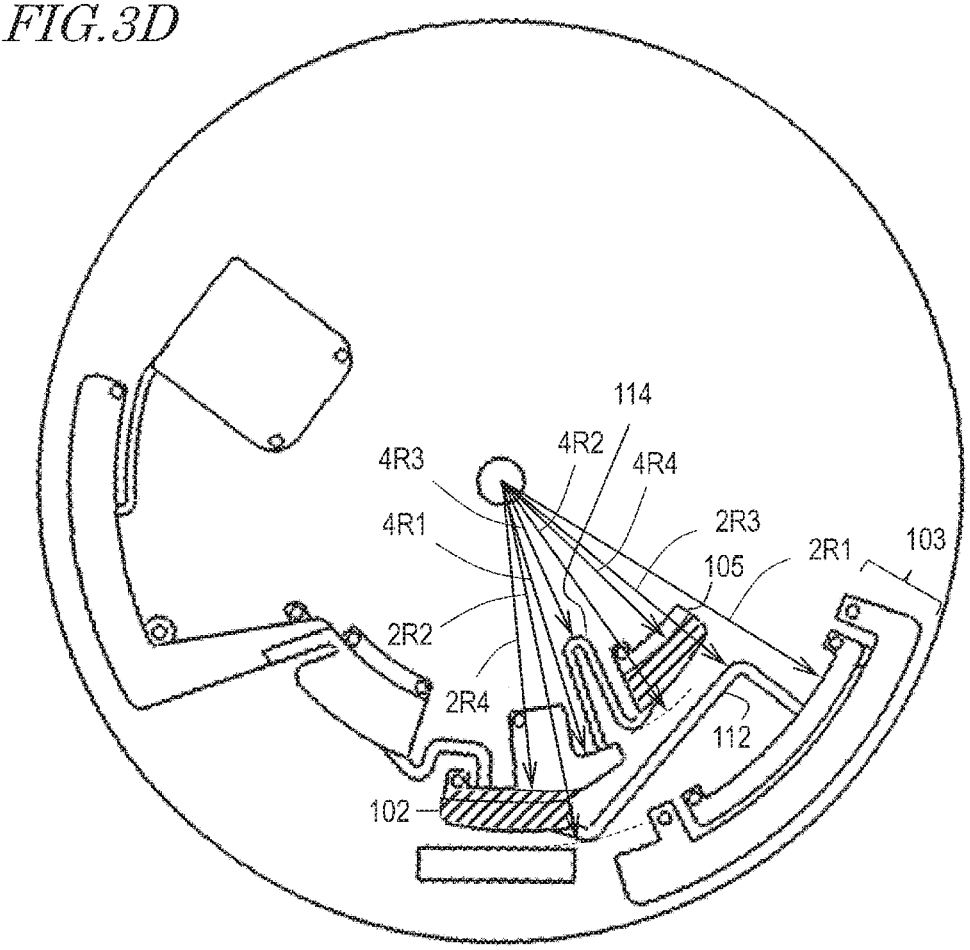
FIG. 3D is a view for illustrating an example of an arrangement relationship of a reaction chamber, a second chamber, a third chamber, a second path, and a fourth path from a rotation axis on the substrate for sample analysis.
Figure 3E:
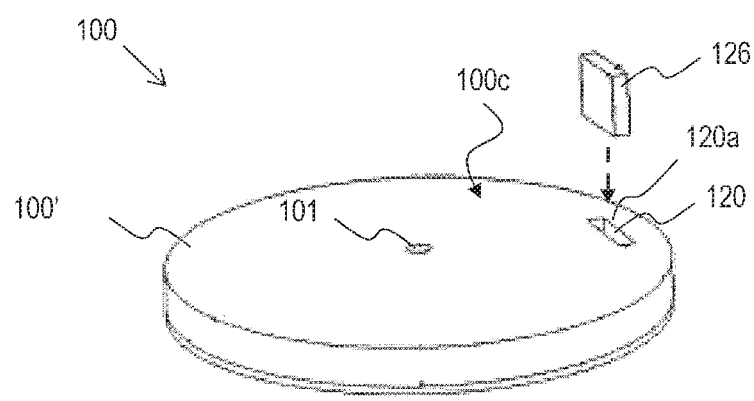
FIG. 3E is a view for schematically illustrating an example of another structure of the substrate for sample analysis.

As illustrated in FIG. 3D, when the distances R1 to R4 are defined as distances 2R1 to 2R4 and 4R1 to 4R4, respectively, regarding the second flow passage 112 and the fourth flow passage 114, the conditions 1 and 2 are represented as follows.
Second flow passage 112
  Condition 1: 2R1>2R2
  Condition 2: 2R4>2R3
Fourth flow passage 114
  Condition 1: 4R1>4R2
  Condition 2: 4R4>4R3

In the case where the flow passage 112 satisfies the conditions 1 and 2, when the substrate 100 for sample analysis is rotated at a rotation speed at which a centrifugal force stronger than a capillary force applied to the liquid in the second flow passage 112 acts at a time when the reaction solution is transported from the reaction chamber 105 to the second chamber 102 or when the washing liquid is transported from the first flow passage 111 to the second chamber 102, the reaction solution or the washing liquid having been transported to the second chamber 102 may be prevented from being directly transported to the third chamber 103.

Further, in the case where the fourth flow passage 114 satisfies the conditions 1 and 2, when the liquid is transported from another chamber (not shown) to the reaction chamber 105 by rotating the substrate 100 for sample analysis at a rotation speed at which a centrifugal force stronger than a capillary force applied to the liquid in the fourth flow passage 114 acts, the complex 310 is formed, and the reaction solution may be prevented from being transferred to the second chamber 102.

When the capillary phenomenon is used, each flow passage or each chamber has a thickness of, for example, from 50 μm to 300 μm. When regions of chambers and flow passages, which have different thicknesses, are formed, different thicknesses can be realized by, for example, differentiating depths of spaces formed in the base substrate 100a. Alternatively, the thicknesses of each flow passage and each chamber may be differentiated by setting the depths of the spaces formed in the base substrate 100a to be constant, and forming protruding portions having different heights at positions corresponding to each chamber and each flow passage of the cover substrate 100b.

At least one air hole 108 is formed in each of the first chamber 101, the second chamber 102, the third chamber 103, the storage chamber 104, and the reaction chamber 105. With this, an inner portion of each chamber is kept at an atmospheric pressure in an environment, and the liquid may move through each flow passage through the capillary phenomenon and the principle of siphon. Further, the reaction chamber 105 and the storage chamber 104 may each have an opening 109 for injection of a liquid, for example, the specimen solution, the reaction solution, and the washing liquid. Further, the air hole 108 may also serve as the opening 109.

It is preferred that the air hole 108 and the opening 109 be formed on an upper surface on a side of a side surface close to the rotation axis 110 in each chamber. With this, even when the substrate 100 for sample analysis is rotated under a state in which each chamber is filled with a liquid, the air hole 108 and the opening 109 can be prevented from being brought into contact with the liquid to cause the liquid to move from the air hole 108 and the opening 109 to outside of the substrate 100 for sample analysis. The air hole 108 and the opening 109 may be formed in a side surface portion of each chamber.

The space of each chamber has, for example, a protruding portion 105p protruding toward the rotation axis 110 side, and it is preferred that the air hole 108 and the opening 109 be positioned in the protruding portion. With this configuration, the positions of the air hole 108 and the opening 109 in each chamber can be set close to the rotation axis 110 to the extent possible in a radial direction. As a result, it becomes possible to increase the amount of a liquid that can be retained in each chamber without being brought into contact with the air hole 108 and the opening 109 under a state in which the substrate 100 for sample analysis is rotated, and a dead space that cannot be used for retaining a liquid in the spaces of those chambers can be reduced.

Operation of Sample Analysis System 501

Figure 4:
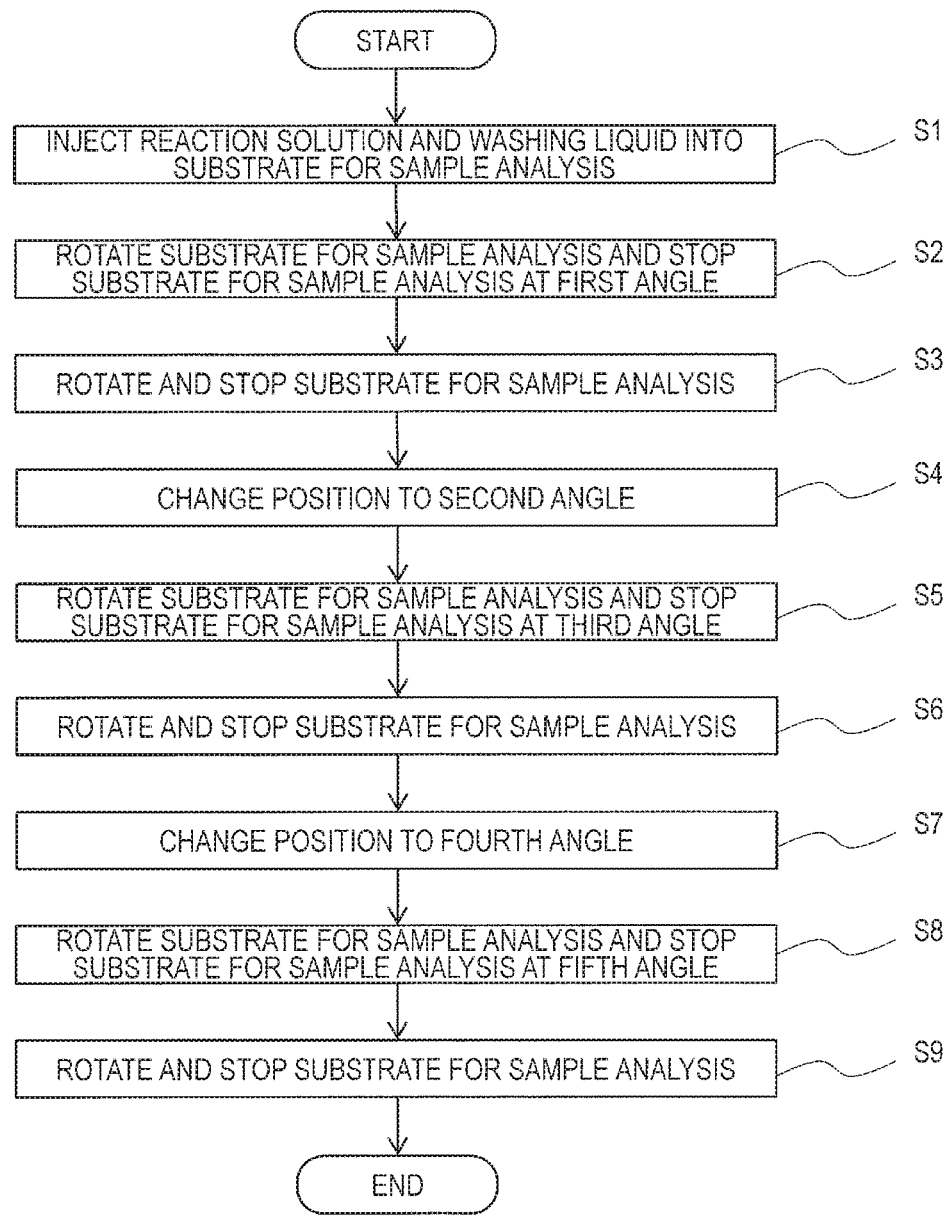
FIG. 4 is a flowchart for illustrating an example of an operation of the sample analysis system.

An operation of the sample analysis system 501 is described. FIG. 4 is a flowchart for illustrating the operation of the sample analysis system 501. A program defining a procedure for controlling each portion of the sample analysis system 501, configured to operate the sample analysis system 501, is stored in, for example, a memory of the control circuit 205, and the following operation is realized through execution of the program by a computing unit. Prior to the following steps, the substrate 100 for sample analysis is loaded onto the sample analysis device 200, and an original point of the substrate 100 for sample analysis is detected.
[Step S1]

Figure 5:
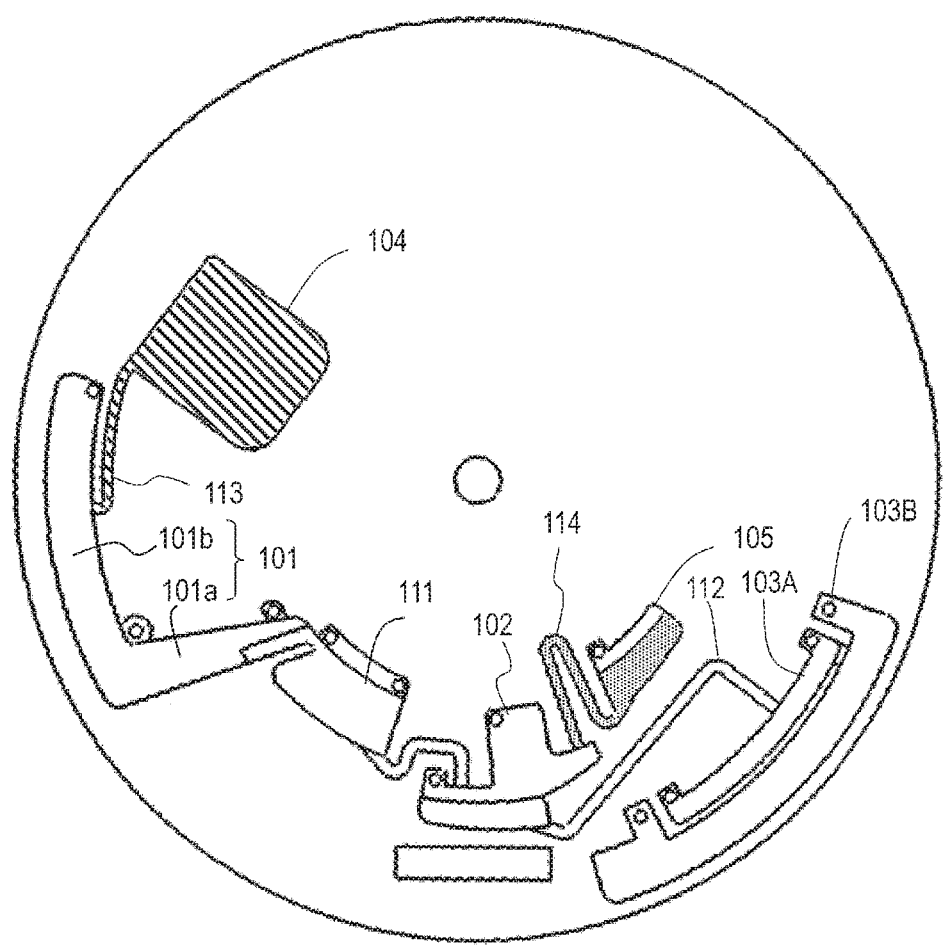
FIG. 5 is a view for schematically illustrating an example of a stopping angle of the substrate for sample analysis and a position of a liquid during operation of the sample analysis system.

First, as illustrated in FIG. 5, a washing liquid is introduced into the storage chamber 104 of the substrate 100 for sample analysis. Further, the magnetized particle immobilized antibody 305, a specimen containing the antigen 306, and the labeling antibody 308 are introduced into the reaction chamber 105. For example, a liquid containing the magnetized particle immobilized antibody 305 may be retained in the reaction chamber 105, and liquids containing the antigen 306 and the labeling antibody 308 may be separately retained in chambers (not shown) arranged in the substrate 100 for sample analysis, respectively. Those liquids may be transported to the reaction chamber 105 with a centrifugal force caused by rotation of the substrate 100 for sample analysis. In the reaction chamber 105, the magnetized particle immobilized antibody 305, the specimen containing the antigen 306, and the labeling antibody 308 are simultaneously reacted with each other by the antigen-antibody reaction, to thereby form the complex 310. At this time, the third flow passage 113 and the fourth flow passage 114 are filled with the washing liquid and the reaction solution containing the complex 310, respectively, through the capillary phenomenon.
[Step S2]

After the complex 310 is generated, the substrate 100 for sample analysis is rotated to cause the reaction solution containing the complex 310 to move to the second chamber 102. In this case, the fourth flow passage 114 is filled with the reaction solution through the capillary phenomenon. Therefore, when a centrifugal force stronger than a capillary force applied to the reaction solution in the fourth flow passage 114 acts on the reaction solution containing the complex 310 in the reaction chamber 105 due to the rotation of the substrate 100 for sample analysis, the reaction solution is transported to the second chamber 102. The reaction solution having been transported to the second chamber 102 is not successively transported to the third chamber 103 under a state in which the substrate 100 for sample analysis is rotated. The reason for this is as follows. The second flow passage 112 forms a siphon as described above, and hence the liquid does not move through the second flow passage 112 in a direction toward the rotation axis 110 against the centrifugal force. In the reaction solution containing the complex 310 having been transported to the second chamber 102, most of the magnetized particles 311 are trapped onto the side surface 102s with an attractive force of the magnet 126.

The rotation speed of the substrate 100 for sample analysis is set so that the liquid, for example, the reaction solution does not move due to gravity when a centrifugal force caused by rotation occurs, and so that a centrifugal force stronger than a capillary force of each capillary path can be applied. This rotation speed is hereinafter set in rotation using a centrifugal force.

Simultaneously with the movement of the reaction solution, the washing liquid is transported from the storage chamber 104 to the second region 101b of the first chamber 101 through the third flow passage 113. A part of the first region 101a may be filled with the washing liquid depending on the volume (size of the space) of the second region 101b and the amount of the washing liquid.

Figure 6:
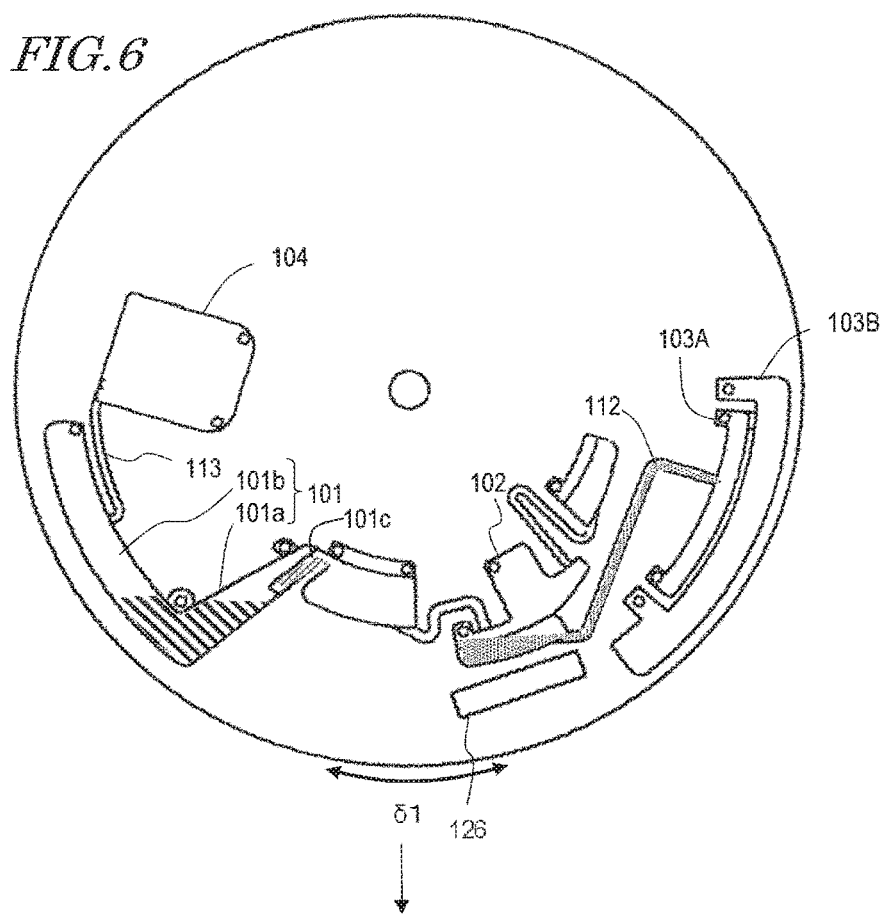
FIG. 6 is a view for schematically illustrating an example of a stopping angle of the substrate for sample analysis and a position of the liquid during operation of the sample analysis system.

After the entire reaction solution and washing liquid are transported to the second chamber 102 and the first chamber 101, respectively, the substrate 100 for sample analysis is stopped at a predetermined angle. As illustrated in FIG. 6, a predetermined first angle refers to an angle at which, in the substrate 100 for sample analysis, the washing liquid having been transported to the first chamber 101 is not brought into contact with the connecting portion 101c of the first chamber 101, and the reaction solution having been shifted to the second chamber 102 can be brought into contact with the opening of the second flow passage 112. This angle depends on the shapes of the first chamber 101 and the second chamber 102, the positions thereof in the substrate 100', the amounts of the washing liquid and the reaction solution, the inclination angle θ of the substrate 100 for sample analysis, and the like. For example, in an example illustrated in FIG. 6, it is only necessary that the gravity direction (represented by the arrow) in the sample analysis system 501 projected onto a flat plane parallel to the substrate 100 for sample analysis fall within an angle range represented by δ1 of the substrate 100 for sample analysis.

The reaction solution in the second chamber 102 is brought into contact with the opening of the second flow passage 112, thereby being filled into the second flow passage 112 through the capillary phenomenon.
[Step S3]

Figure 7:
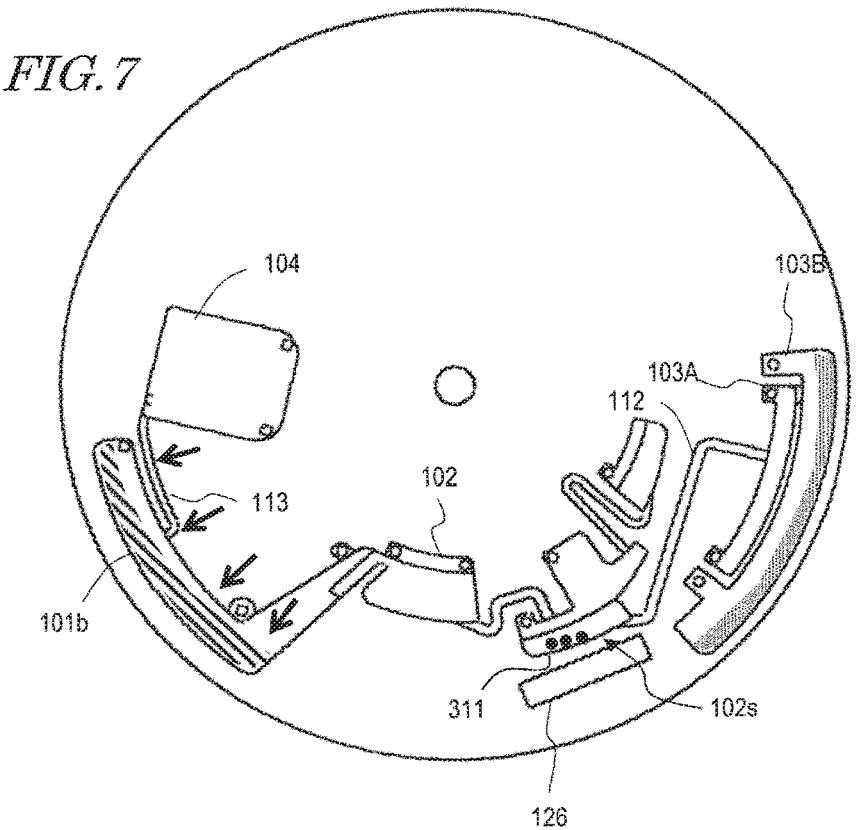
FIG. 7 is a view for schematically illustrating an example of a stopping angle of the substrate for sample analysis and a position of the liquid during operation of the sample analysis system.

The substrate 100 for sample analysis is rotated. A centrifugal force occurs along with the rotation and acts on the reaction solution in the second chamber 102 and the magnetized particles 311 (complex 310 and unreacted magnetized particle immobilized antibody 305). This centrifugal force acts so that the liquid and the complex move to the side surface 102s side of the second chamber 102. Therefore, as illustrated in FIG. 7, the magnetized particles 311 are pressed against the side surface 102s.

The reaction solution having received the centrifugal force is discharged from the second flow passage 112 and transported to the first sub-chamber 103A of the third chamber 103. Further, the reaction solution is transported to the second sub-chamber 103B through the fifth flow passage 115. The magnetized particles 311 are strongly pressed against the side surface 102s and trapped thereon through the combination of the centrifugal force and the attractive force of the magnet 126.

As a result, only the reaction solution is discharged from the second flow passage 112, and the magnetized particles 311 remain in the second chamber 102. The washing liquid in the first chamber 101 receives the centrifugal force caused by rotation and moves to the second region 101*b*. After the transportation of the reaction solution to the second sub-chamber 103B is completed, the rotation of the substrate 100 for sample analysis is stopped.

With this, the reaction solution and the magnetized particles 311 are separated. Specifically, the reaction solution moves to the second sub-chamber 103B of the third chamber 103, and the magnetized particles 311 remain in the second chamber 102. Even when the rotation of the substrate 100 for sample analysis is stopped, the magnetized particles 311 may keep a state of aggregating on the side surface 102*s* due to the attractive force from the magnet 126. The stopping angle in this case may be the first angle, a second angle in a next step, or other angles.

[Step S4 (Step (a))]

Figure 8:
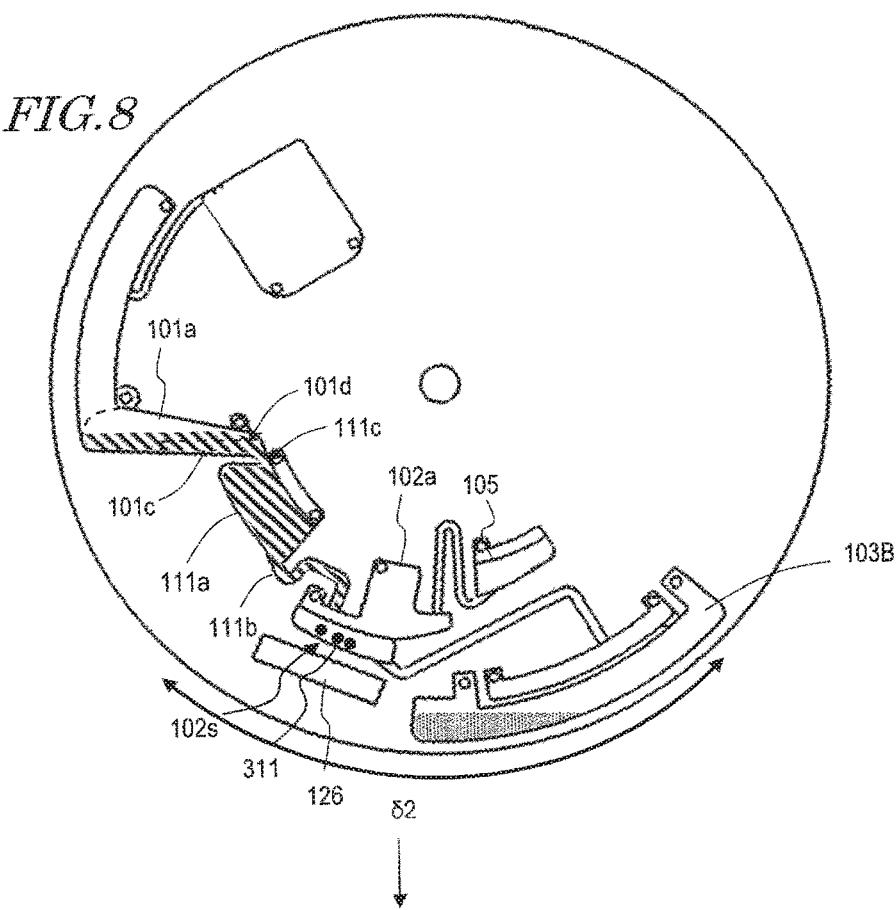
FIG. 8 is a view for schematically illustrating an example of a stopping angle of the substrate for sample analysis and a position of the liquid during operation of the sample analysis system.

As illustrated in FIG. 8, the substrate 100 for sample analysis is slightly rotated and stopped at a predetermined second angle. The second angle refers to an angle at which the washing liquid having been transported to the first chamber 101 is brought into contact with the connecting portion 101*c* of the first chamber 101. For example, in an example illustrated in FIG. 8, the second angle is an angle at which the gravity direction is positioned within an angle range represented by δ2 of the substrate 100 for sample analysis.

The washing liquid is sucked from the first chamber 101 with the capillary force in the connecting portion 101*c* and the first portion 111*a* and the second portion 111*b* of the first flow passage 111, and the first portion 111*a* and the second portion 111*b* of the first flow passage 111 are filled with the washing liquid. With this, the washing liquid for one time of washing is weighed.

The substrate 100 for sample analysis may be rotated, that is, shaken several times alternately clockwise or counterclockwise with respect to the second angle so that the first flow passage 111 is filled with the washing liquid reliably. The capillary force acts on the first flow passage 111, and hence the washing liquid does not move from the second portion 111*b* of the first flow passage 111 to the second chamber 102 in this case.

[Step S5 [Steps (b) and (c)]]

Figure 9:
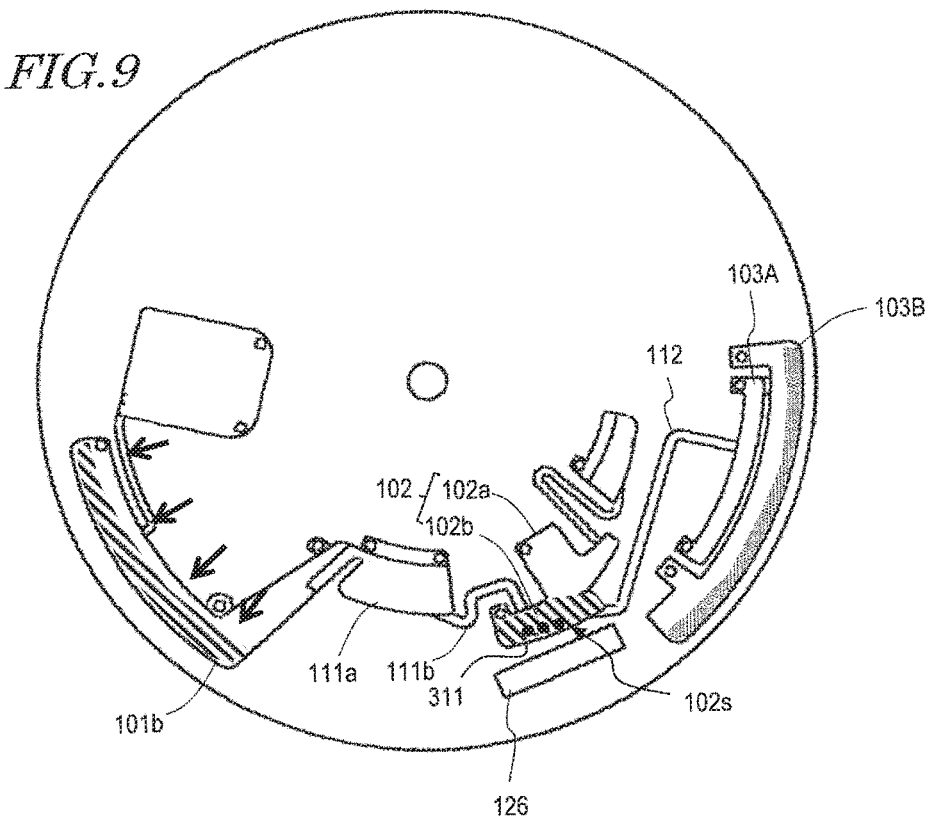
FIG. 9 is a view for schematically illustrating an example of a stopping angle of the substrate for sample analysis and a position of the liquid during operation of the sample analysis system.

Subsequently, the substrate 100 for sample analysis is rotated. The centrifugal force caused by the rotation acts on the washing liquid in the first flow passage 111 and the first chamber 101. As illustrated in FIG. 9, the washing liquid in the first flow passage 111 is transported to the second chamber 102 with the centrifugal force. Meanwhile, the excess washing liquid positioned in the first region 101*a* in the first chamber 101 moves to the second region 101*b* in the first chamber 101 with the centrifugal force. Thus, only the washing liquid weighed with the first flow passage 111 is transported to the second chamber 102. The centrifugal force also acts on the washing liquid having been transported to the second chamber 102, and hence the washing liquid remains substantially in the second chamber 102 without moving toward the rotation axis 110 in the second flow passage 112. With this, the magnetized particles 311 in the second chamber 102 are brought into contact with the washing liquid and subjected to the first washing.

Figure 10:
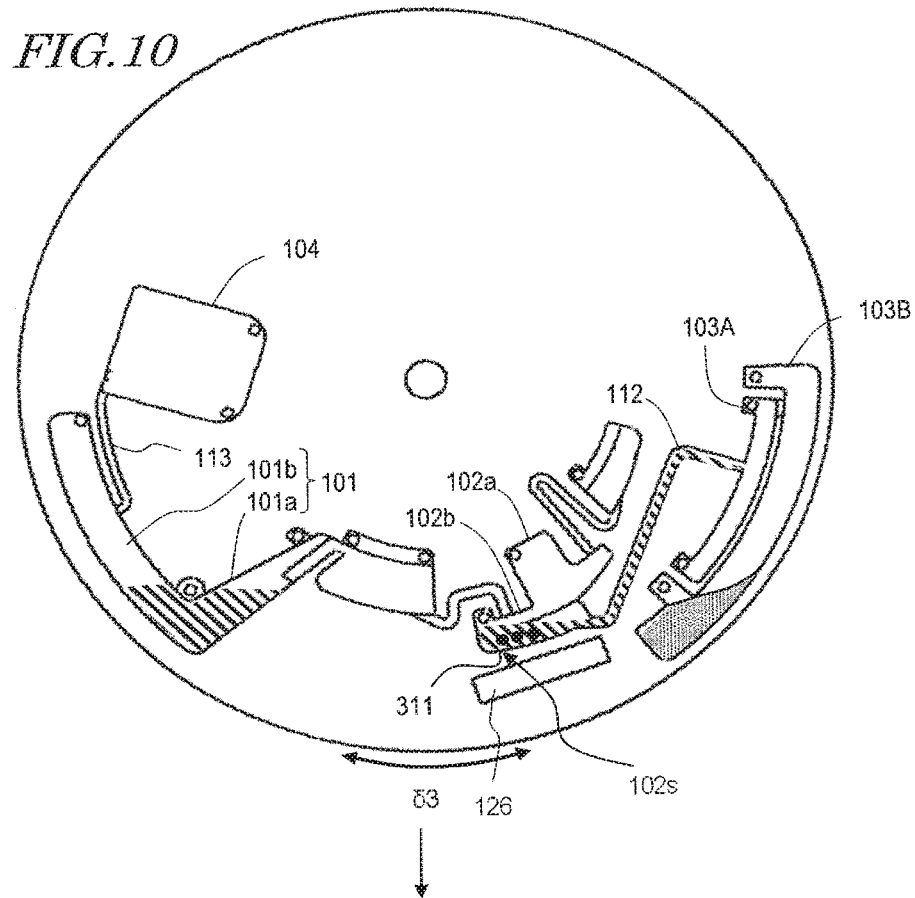
FIG. 10 is a view for schematically illustrating an example of a stopping angle of the substrate for sample analysis and a position of the liquid during operation of the sample analysis system.

As illustrated in FIG. 10, after the entire washing liquid in the first flow passage 111 has moved to the second chamber 102, the substrate 100 for sample analysis is stopped at a predetermined third angle. The third angle refers to an angle at which the washing liquid in the first chamber 101 is not brought into contact with the connecting portion 101*c*, and the washing liquid having been shifted to the second chamber 102 can be brought into contact with the opening of the second flow passage 112. For example, in an example illustrated in FIG. 10, it is only necessary that the gravity direction in the sample analysis system 501 projected onto a flat plane parallel to the substrate 100 for sample analysis fall within an angle range represented by 63 of the substrate 100 for sample analysis.

The washing liquid in the second chamber 102 is brought into contact with the opening of the second flow passage 112, thereby being filled into the second flow passage 112 through the capillary phenomenon.

[Step S6 (Step (d))]

The substrate 100 for sample analysis is rotated. A centrifugal force occurs along with the rotation and acts on washing liquid in the second chamber 102 and the magnetized particles 311. This centrifugal force acts so that the washing liquid and the magnetized particles 311 move to the side surface 102*s* side of the second chamber 102, and the magnetized particles 311 are trapped onto the side surface 102*s* with the centrifugal force and the attractive force of the magnet 126.

The washing liquid having received the centrifugal force is discharged from the second flow passage 112 and transported to the first sub-chamber 103A of the third chamber 103. Further, the washing liquid is transported to the second sub-chamber 103B through the fifth flow passage 115.

Figure 11:
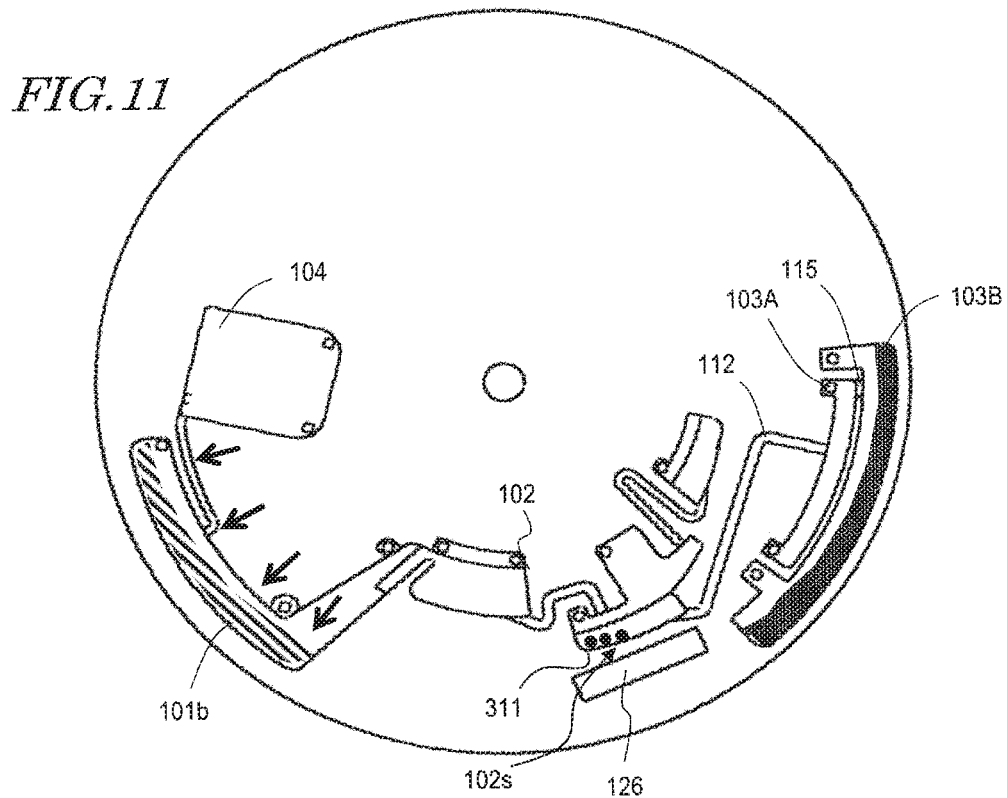
FIG. 11 is a view for schematically illustrating an example of a stopping angle of the substrate for sample analysis and a position of the liquid during operation of the sample analysis system.

As a result, as illustrated in FIG. 11, only the washing liquid is discharged from the second flow passage 112, and the magnetized particles 311 remain in the second chamber 102. The washing liquid in the first chamber 101 receives the centrifugal force caused by rotation and moves to the second region 101*b*. After the transportation of the washing liquid to the second sub-chamber 103B is completed, the rotation of the substrate 100 for sample analysis is stopped. With this, the washing liquid and the magnetized particles 311 are separated. Specifically, the washing liquid moves to the second sub-chamber 103B of the third chamber 103, and the magnetized particles 311 remain in the second chamber 102. Even when the rotation of the substrate 100 for sample analysis is stopped, the magnetized particles 311 may keep a state of aggregating on the side surface 102*s* due to the attractive force from the magnet 126. The stopping angle in this case may be the third angle or a fourth angle in a next step.

[Step S7 (Step (e))]

Figure 12:
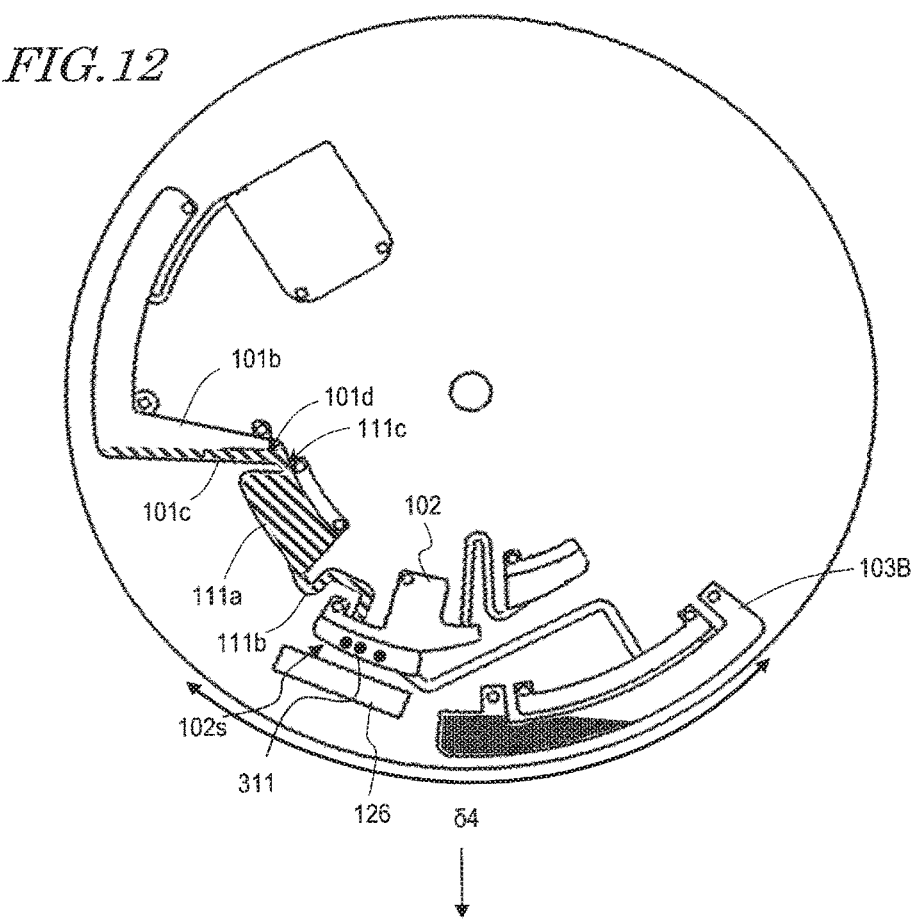
FIG. 12 is a view for schematically illustrating an example of a stopping angle of the substrate for sample analysis and a position of the liquid during operation of the sample analysis system.

As illustrated in FIG. 12, the substrate 100 for sample analysis is slightly rotated and stopped at a predetermined fourth angle. The fourth angle refers to an angle at which the washing liquid having been transported to the first chamber 101 is brought into contact with the connecting portion 101*c* of the first chamber 101. For example, in an example illustrated in FIG. 12, the fourth angle is an angle at which the gravity direction is positioned within an angle range represented by δ4 of the substrate 100 for sample analysis. The amount of the washing liquid remaining in the first chamber 101 is different from that in Step S4, and hence the angle range δ4 may be different from the angle range δ2.

The washing liquid is sucked from the first chamber 101 with the capillary force in the connecting portion 101*c* and the first portion 111*a* and the second portion 111*b* of the first flow passage 111, and the first portion 111*a* and the second portion 111*b* of the first flow passage 111 are filled with the washing liquid. With this, the washing liquid for one time of washing is weighed again.

The substrate 100 for sample analysis may be shaken with respect to the fourth angle so that the first flow passage 111 is filled with the washing liquid reliably. The capillary force acts on the first flow passage 111, and hence the washing liquid does not move from the second portion 111b of the first flow passage 111 to the second chamber 102 in this case.

[Step S8]

Figure 13:
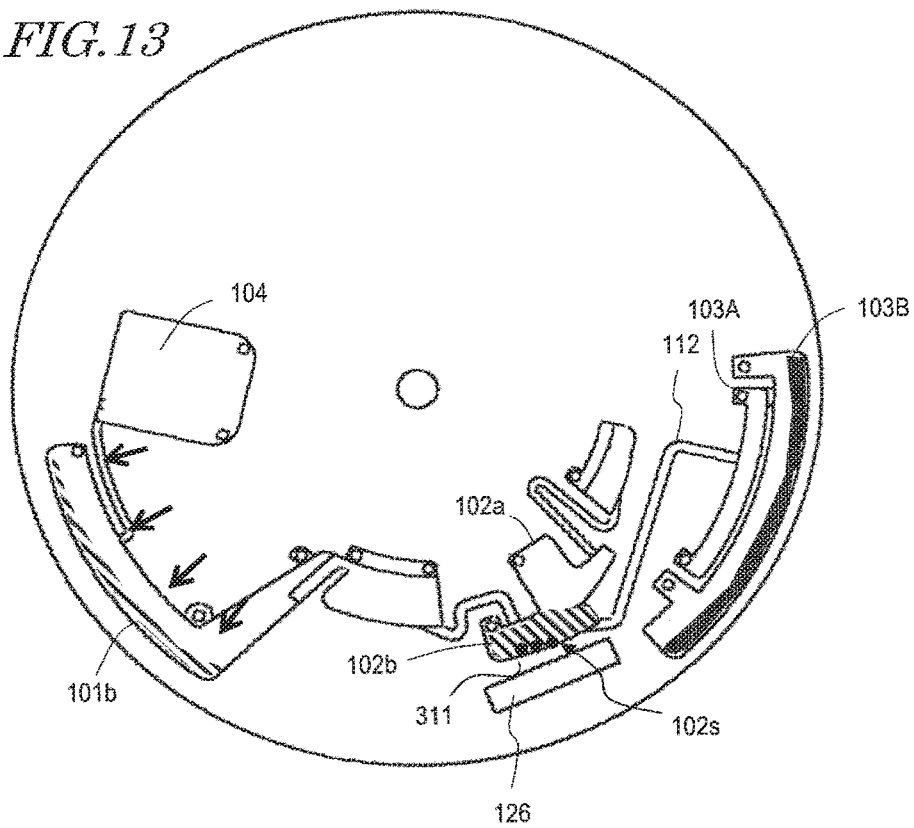
FIG. 13 is a view for schematically illustrating an example of a stopping angle of the substrate for sample analysis and a position of the liquid during operation of the sample analysis system.

Subsequently, the substrate 100 for sample analysis is rotated. The centrifugal force caused by the rotation acts on the washing liquid in the first flow passage 111 and the first chamber 101. As illustrated in FIG. 13, the washing liquid in the first flow passage 111 is transported to the second chamber 102 with the centrifugal force. Meanwhile, the excess washing liquid positioned in the first region 101a in the first chamber 101 moves to the second region 101b in the first chamber 101 with the centrifugal force. Thus, only the washing liquid weighed with the first flow passage 111 is transported to the second chamber 102. The centrifugal force also acts on the washing liquid having been transported to the second chamber 102, and hence the washing liquid remains substantially in the second chamber 102 without moving toward the rotation axis 110 in the second flow passage 112. With this, the magnetized particles 311 in the second chamber 102 are brought into contact with the washing liquid and subjected to the second washing.

Figure 14:
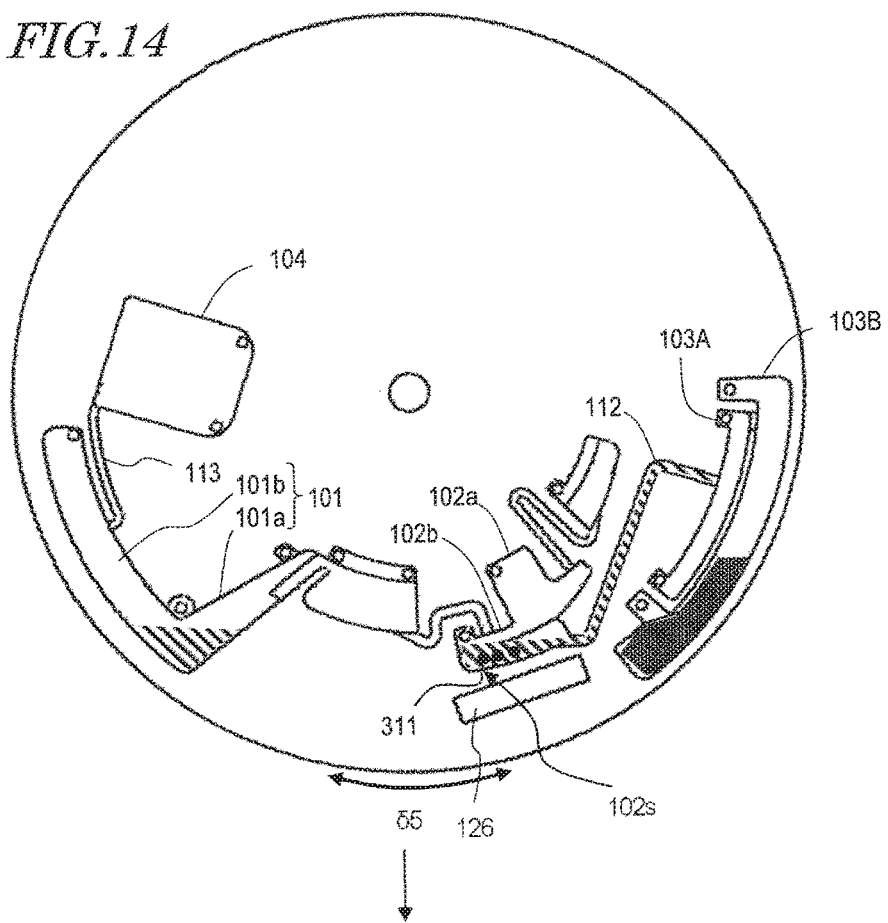
FIG. 14 is a view for schematically illustrating an example of a stopping angle of the substrate for sample analysis and a position of the liquid during operation of the sample analysis system.

As illustrated in FIG. 14, after the entire washing liquid in the first flow passage 111 has moved to the second chamber 102, the substrate 100 for sample analysis is stopped at a predetermined fifth angle. The fifth angle refers to an angle at which the washing liquid in the first chamber 101 is not brought into contact with the connecting portion 101c, and the washing liquid having been shifted to the second chamber 102 can be brought into contact with the opening of the second flow passage 112. For example, in an example illustrated in FIG. 14, it is only necessary that the gravity direction in the sample analysis system 501 projected onto a flat plane parallel to the substrate 100 for sample analysis fall within an angle range represented by 65 of the substrate 100 for sample analysis.

The washing liquid in the second chamber 102 is brought into contact with the opening of the second flow passage 112, thereby being filled into the second flow passage 112 through the capillary phenomenon.

[Step S9 (Step (f))]

The substrate 100 for sample analysis is rotated. A centrifugal force occurs along with the rotation and acts on the washing liquid in the second chamber 102 and the magnetized particles 311. This centrifugal force acts so that the washing liquid and the magnetized particles 311 move to the side surface 102s side of the second chamber 102. The magnetized particles 311 are trapped onto the side surface 102s with the centrifugal force and the attractive force of the magnet 126.

The washing liquid having received the centrifugal force is discharged from the second flow passage 112 and transported to the first sub-chamber 103A of the third chamber 103. Further, the washing liquid is transported to the second sub-chamber 103B through the fifth flow passage 115.

Figure 15:
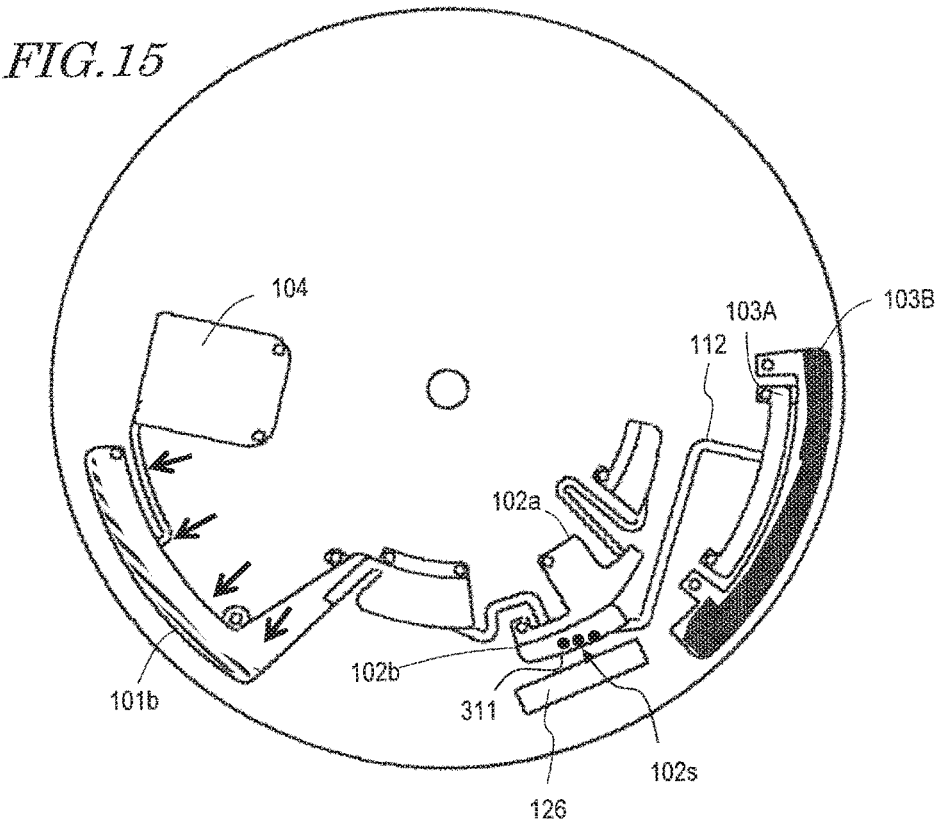
FIG. 15 is a view for schematically illustrating an example of a stopping angle of the substrate for sample analysis and a position of the liquid during operation of the sample analysis system.

As a result, as illustrated in FIG. 15, only the washing liquid is discharged from the second flow passage 112, and the magnetized particles 311 remain in the second chamber 102. The washing liquid in the first chamber 101 receives the centrifugal force caused by rotation and moves to the second region 101b. After the transportation of the washing liquid to the second sub-chamber 103B is completed, the rotation of the substrate 100 for sample analysis is stopped. With this, the washing liquid and the magnetized particles 311 are separated. Specifically, the washing liquid moves to the second sub-chamber 103B of the third chamber 103, and the magnetized particles 311 remain in the second chamber 102. Even when the rotation of the substrate 100 for sample analysis is stopped, the magnetized particles 311 may keep a state of aggregating on the side surface 102s due to the attractive force from the magnet 126.

Through the above-mentioned steps, the B/F separation is performed. Specifically, the magnetized particles 311 are separated from various unreacted substances and the washing liquid.

After that, signals such as a dye, luminescence, fluorescence, and the like in accordance with the labeling substance 307 of the labeling antibody 308 bound in the complex 310 contained in the magnetized particles 311 are detected through use of the optical measurement unit 207. With this, the detection of the antigen 306, the quantitative determination of a concentration of the antigen 306, and the like can be performed.

As described above, in the substrate for sample analysis, sample analysis device, and sample analysis system according to this embodiment, a liquid can be introduced into the same chamber in divided portions. Therefore, when the B/F separation is performed through use of the substrate for sample analysis, sufficient washing can be performed. When a liquid is weighed, a flow passage that exhibits a capillary force is used, and hence each weighing can be performed more reliably and more accurately. Further, this operation may be realized by control of rotation and stoppage of the substrate for sample analysis and control of an angle at a time of stopping. Therefore, this operation is suitably applicable to an analysis method involving analyzing a component in a specimen through complicated reaction steps including the B/F separation without using large analysis equipment or performing manual operation by an operator.

Figure 16:
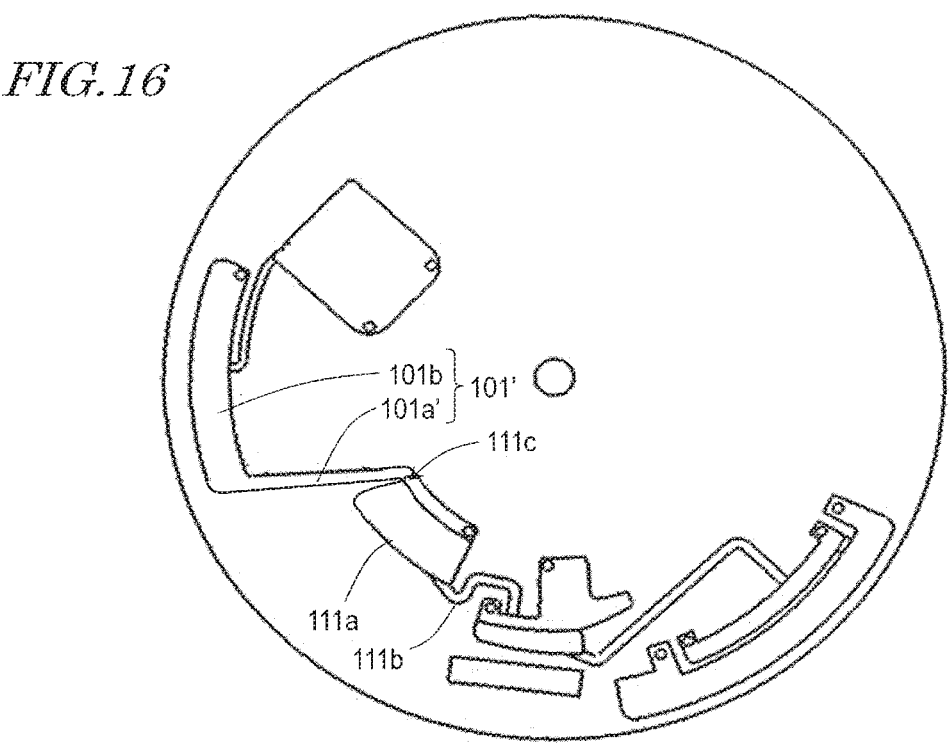
FIG. 16 is a plan view for illustrating another example of the substrate for sample analysis.

The shape and arrangement of each chamber and flow passage of the substrate for sample analysis illustrated in the above-mentioned embodiment are examples and may be altered variously. For example, a substrate 150 for sample analysis illustrated in FIG. 16 includes a first chamber 101' including a first region 101a' and a second region 101b. Unlike the substrate 100 for sample analysis illustrated in FIG. 3B, the first region 101a' does not include the connecting portion 101c and includes only a portion extending from the first opening 111c of the first region toward a side farther from the rotation axis 110. The entire first region 101a' can suck a liquid retained in the second region 101b through the capillary phenomenon. The entire first region 101a' can suck the washing liquid retained in the first chamber 101' through the capillary phenomenon and retain the washing liquid. One end of the first region 101a' is connected to the first opening 111c of the first flow passage 111, and the second region 101b is connected to the first region 101a at a position farther from the rotation axis 110 than the first opening 111c. The substrate 150 for sample analysis can also weigh the washing liquid for one time of washing with the first flow passage 111 as described above. In the substrate 150 for sample analysis, when a portion of the first region 101a' connected to the second region 101b is in contact with the washing liquid, the first region 101a' and the first flow passage 111 can be filled with the washing liquid with a capillary force. Therefore, the first flow passage 111 can be filled with the washing liquid in a range of a rotation angle larger than that of the substrate 100 for sample analysis, and the first angle range 61 and the second angle range δ2 are enlarged. Thus, the degree of freedom of control in the sample analysis system is enhanced.

Figure 17A:
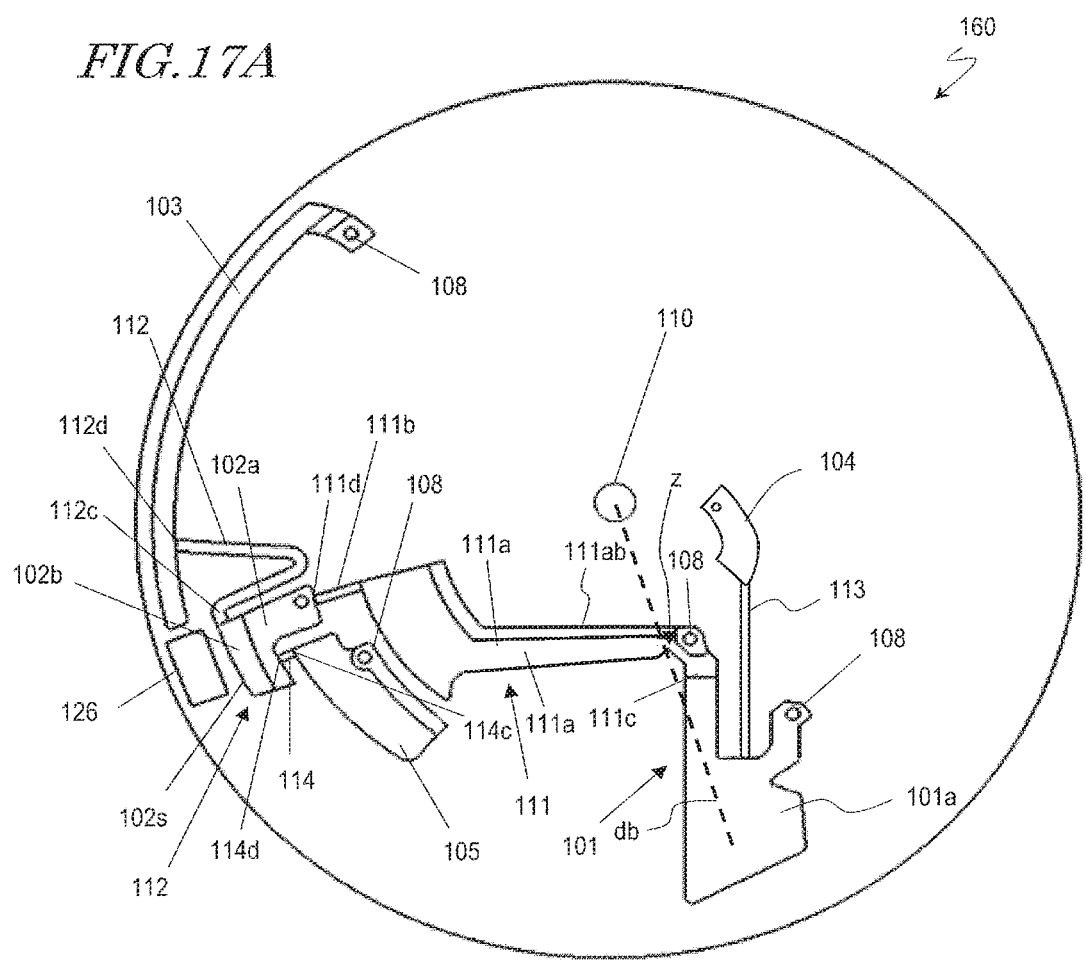
FIG. 17A is a plan view for illustrating another example of the substrate for sample analysis.

Further, a substrate 160 for sample analysis illustrated in FIG. 17A is another example of the substrate 100 for sample analysis illustrated in FIG. 3B. The substrate 160 for sample analysis is described in comparison with the substrate 100 for sample analysis illustrated in FIG. 3B.

As illustrated in FIG. 17A, unlike the substrate 100 for sample analysis illustrated in FIG. 3B, the first chamber 101 includes only the first region 101a. Specifically, the first chamber 101 includes the first region 101a including a portion extending from the first opening 111c toward a side farther from the rotation axis and does not include the second region 101b. The washing liquid having been transported from the storage chamber 104 through the third flow passage is retained in the first region 101a positioned farther from the rotation axis 110 than the first opening 111c. Unlike the substrate 100 for sample analysis illustrated in FIG. 3B, the first chamber 101 does not include the connecting portion 101c.

Similarly to FIG. 3B, the second chamber 102 includes the first region 102a and the second region 102b. Further, the magnet 126 is also arranged close to the side surface 102s of the second chamber 102 positioned farthest from the rotation axis 110.

Unlike the substrate 100 for sample analysis illustrated in FIG. 3B, the third chamber 103 does not include the first sub-chamber 103A and the second sub-chamber 103B and includes one chamber.

Similarly to the substrate 100 for sample analysis illustrated in FIG. 3B, the first flow passage 111 includes the first portion 111a and the second portion 111b. The first portion 111a includes the first opening 111c and is connected to the first chamber 101. The second portion 111b includes the second opening 111d and is connected to the second chamber 102. In the substrate 100 for sample analysis illustrated in FIG. 3B, a part of the first chamber 101 and a part of the first flow passage 111 are positioned in a circumferential direction with the rotation axis 110 being the center with the first opening 111c interposed therebetween. Meanwhile, in the substrate 160 for sample analysis, as illustrated in FIG. 17A, a part of the first chamber 101 and a part of the first flow passage 111 are positioned substantially in a radial direction with the rotation axis 110 being the center with the first opening 111c interposed therebetween.

The first flow passage 111 further includes a space 111ab having one air hole 108 along the first portion 111a. Similarly to the substrate 100 for sample analysis, the space 111ab is a space configured to secure the air hole 108 and is not a capillary path capable of being filled with a liquid through the capillary phenomenon. For example, the thickness of the space 111ab is larger than the thickness of the first portion 111a, and when the first portion 111a is filled with a liquid through the capillary phenomenon, the space 111ab is not filled with the liquid. When air bubbles are generated in the liquid retained in the first portion 111a for some reason, the arrangement of the space 111ab allows the air bubbles to move to the space 111ab, with the result that the air bubbles in the liquid are easily eliminated. With this, when the substrate 100 for sample analysis is rotated, in particular, the air bubbles can be prevented from entering the second portion 111b to hinder the movement of the liquid.

Figure 17B:
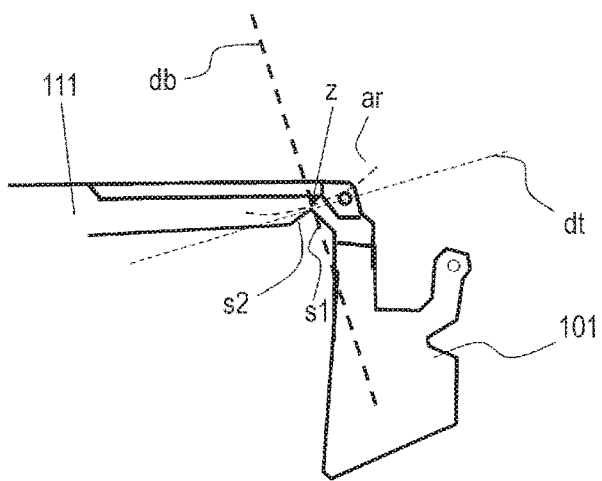
FIG. 17B is an enlarged plan view for illustrating a vicinity of a connecting portion between a first flow passage and a first chamber of the substrate for sample analysis illustrated in FIG. 17A.

As described in detail below, when the rotation angle of the substrate 160 for sample analysis is changed to a position at which the washing liquid is brought into contact with the first opening 111c under a state in which the washing liquid is retained in the first chamber 101, the first flow passage 111 excluding the space 111ab is filled with the washing liquid through the capillary phenomenon. In this state, the substrate 160 for sample analysis is rotated at a rotation speed at which a centrifugal force stronger than a capillary force applied to the washing liquid in the first flow passage 111 is applied. In this case, as illustrated in FIG. 17A, the washing liquid is separated into the washing liquid transported to the first chamber 101 and the washing liquid returned to the first flow passage 111, based on a straight line db connecting the rotation axis 110 to a position z on a flat plane perpendicular to the rotation axis 110. As illustrated in FIG. 17B, the reference position z is defined by two side surfaces s1 and s2 positioned farther from the rotation axis 110 than the space of the first chamber 101 or the space of the first flow passage 111, which are the surface s1 inclined to the first chamber 101 side and the surface s2 inclined to the second chamber side with respect to a tangential direction dt of an arc ar with the rotation axis 110 being the center.

As described above, in the substrate 100 for sample analysis illustrated in FIG. 3B, the entire liquid filled in the first flow passage 111 is transported to the second chamber 102. However, the present invention is not limited thereto, and a part of the liquid may be transported to the second chamber 102. Also in an example of FIG. 17A, when the first flow passage 111 is filled with the washing liquid, the weighed liquid can be transported to the second chamber 102.

Similarly to the substrate 100 for sample analysis illustrated in FIG. 3B, the second flow passage 112 is a capillary path and has a siphon structure. Similarly to the substrate 100 for sample analysis, the fourth flow passage 114 is a capillary path but does not have a siphon structure.

Second Embodiment

Now, a sample analysis system according to a second embodiment of this disclosure is described. The sample analysis system according to the second embodiment includes a substrate 162 for sample analysis and the sample analysis device 200. The configuration of the sample analysis device 200 is the same as that of the sample analysis device 200 in the sample analysis system 501 according to the first embodiment.

Figure 18:
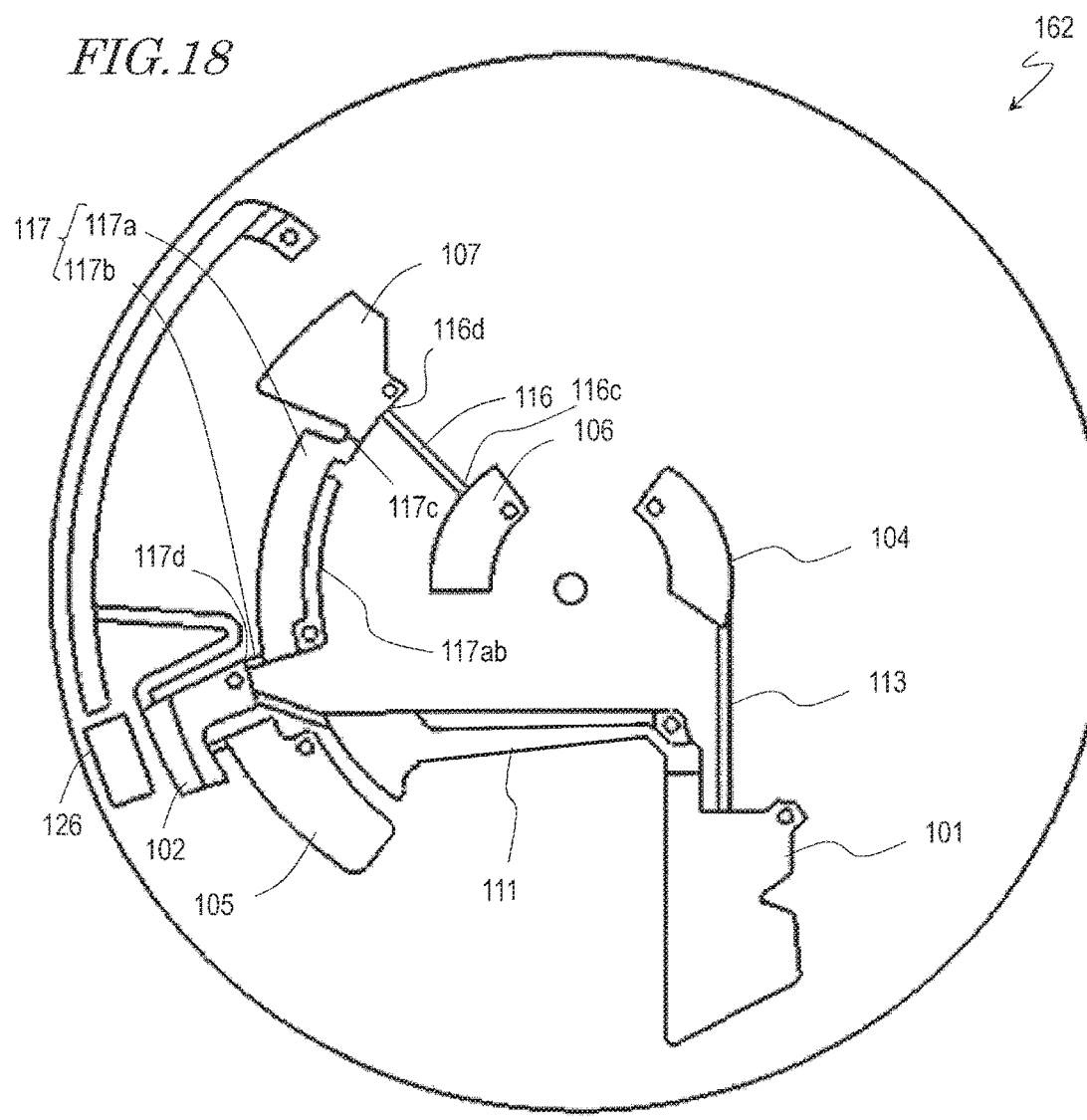
FIG. 18 is a plan view for illustrating an example of a substrate for sample analysis used in a second embodiment.

As illustrated in FIG. 18, the substrate 162 for sample analysis according to this embodiment includes a storage chamber 106, a fourth chamber 107, a sixth flow passage 116, and a seventh flow passage 117 in addition to the structure of the substrate 160 for sample analysis illustrated in FIG. 17A. The storage chamber 106 is positioned closer to the rotation axis 110 than the fourth chamber 107 in a radial direction. The storage chamber 106 is configured to store a substrate solution at a time of start of analysis using the sample analysis system. Further, after the start of the analysis using the sample analysis system, the fourth chamber 107 retains the substrate solution during washing of the complex 310. The shapes of the storage chamber 106 and the fourth chamber 107 are not particularly limited, and the storage chamber 106 and the fourth chamber 107 may have any shapes.

The sixth flow passage 116 connects the storage chamber 106 and the fourth chamber 107 to each other. The sixth flow passage 116 extends in a radial direction with the rotation axis 110 being the center and is formed of a capillary path. The sixth flow passage 116 has a seventh opening 116c and an eighth opening 116d, and the seventh opening 116c is positioned between the storage chamber 106 and the sixth flow passage 116. Further, the eighth opening 116d is positioned between the sixth flow passage 116 and the fourth chamber 107.

It is preferred that, among side surfaces of the storage chamber 106, the seventh opening 116c be formed on a side surface (outermost peripheral side surface) positioned on a side farthest from the rotation axis 110 or on a side surface adjacent to the outermost peripheral side surface, which is a position close to the outermost peripheral side surface.

Meanwhile, it is preferred that, among side surfaces of the fourth chamber 107, the eighth opening 116d be formed on a side surface (innermost peripheral side surface) positioned closest to the rotation axis 110 or a side surface adjacent to the innermost peripheral side surface, which is a position close to the innermost peripheral side surface.

The seventh flow passage 117 includes a first portion 117a and a second portion 117b, and a ninth opening 117c and a tenth opening 117d. The ninth opening 117c is positioned between the fourth chamber 107 and the first portion 117a of the seventh flow passage 117. The first portion 117a of the seventh flow passage 117 is a capillary path, and an inner portion thereof can be filled with a liquid through the capillary phenomenon. The first portion 117a extends substantially in a circumferential direction.

The tenth opening 117d is positioned between the second portion 117b and the second chamber 102, and the first portion 117a and the second portion 117b are connected to each other at each one end in which the ninth opening 117c and the tenth opening 117d are not positioned.

The ninth opening 117c is positioned on a side closer to the rotation axis 110 than the tenth opening 117d. In order to transport a substantially total amount of the liquid in the seventh flow passage 117 to the second chamber 102, it is preferred that each portion of the seventh flow passage 117 be arranged at the same position as that of the ninth opening 117c from the rotation axis 110 or at the position farther from the rotation axis 110 than the ninth opening 117c. With this, when a centrifugal force stronger than a capillary force applied to the substrate solution in the seventh flow passage 117 acts on the substrate solution under a state in which the seventh flow passage 117 is filled with the substrate solution, the entire substrate solution in the seventh flow passage 117 is transported to the second chamber 102 without being returned to the fourth chamber 107.

When a total volume of the first portion 117a and the second portion 117b corresponds to the amount of the substrate solution to be used for analysis, and a space between the ninth opening 117c and the tenth opening 117d of the seventh flow passage 117 is filled with the substrate solution, the substrate solution is weighed. As described above, both the first portion 117a and the second portion 117b of the seventh flow passage 117 can be filled with the substrate solution retained in the fourth chamber 107 through the capillary phenomenon.

As illustrated in FIG. 18, a space 117ab having one air hole 108 may be formed along the rotation axis side of the first portion 117a. When the thickness of the space 117ab is larger than the thickness of the first portion 117a, and the first portion 117a is filled with the substrate solution through the capillary phenomenon, a capillary force does not substantially act on the space 117ab, and the space 117ab is not filled with the substrate solution. Similarly to the space 111ab of the substrate 100 for sample analysis, when air bubbles are generated in the substrate solution retained in the first portion 117a for some reason, the arrangement of the space 117ab allows the air bubbles to move to the space 117ab, with the result that the air bubbles in the substrate solution are easily eliminated. With this, when the substrate 162 for sample analysis is rotated, in particular, the air bubbles can be prevented from entering the second portion 117b to hinder the movement of the substrate solution.

Other configurations of the substrate 162 for sample analysis are the same as those of the substrate 100 for sample analysis illustrated in FIG. 3B and the substrate 160 for sample analysis illustrated in FIG. 17A.

Figure 19:
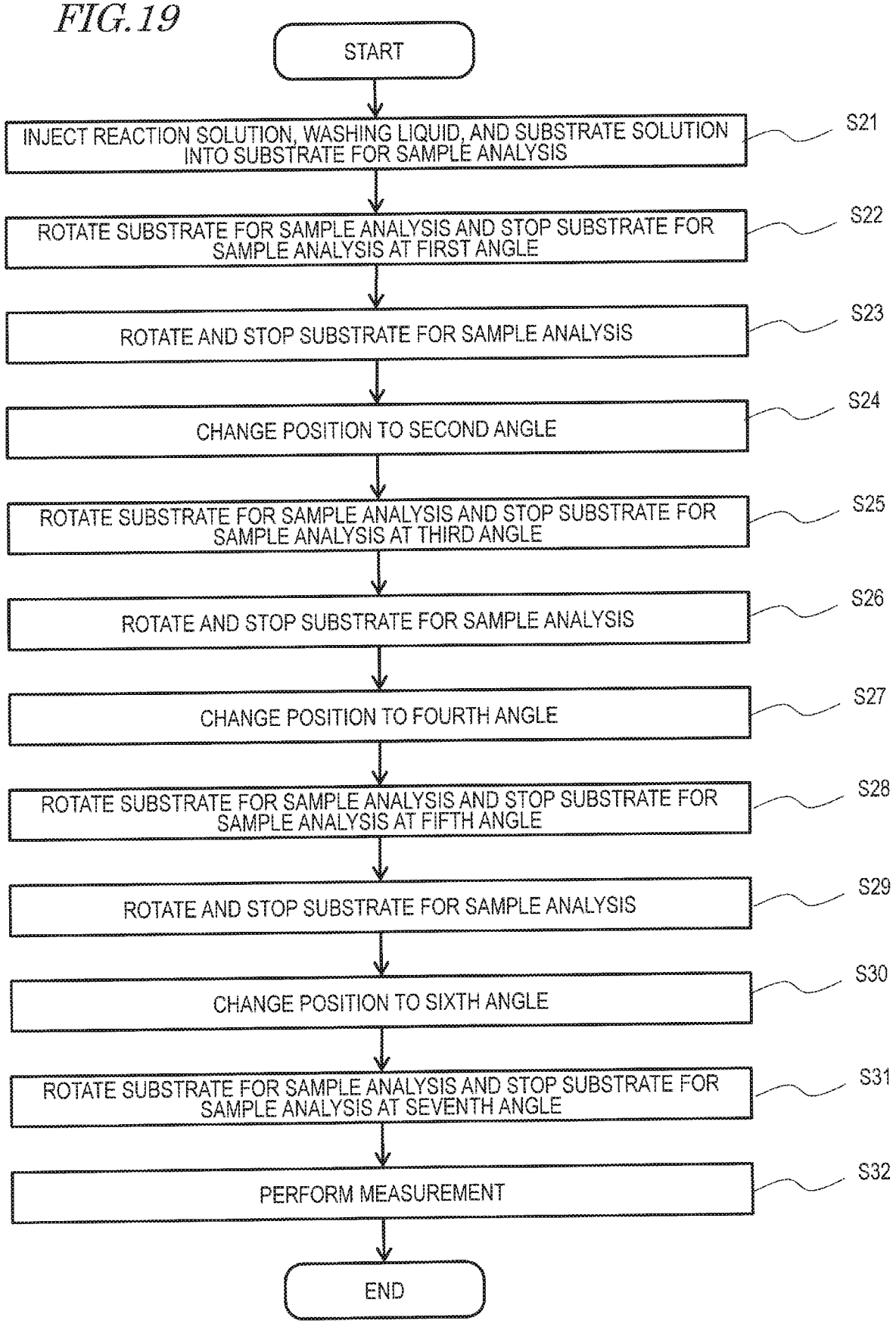
FIG. 19 is a flowchart for illustrating an example of an operation of a sample analysis system according to the second embodiment using the substrate for sample analysis illustrated in FIG. 18.

Next, an operation of the sample analysis system according to the second embodiment is described. FIG. 19 is a flowchart for illustrating the operation of the sample analysis system 502. A program defining a procedure for controlling each portion of the sample analysis system 502, configured to operate the sample analysis system 502, is stored in, for example, a memory of the control circuit 205, and the following operation is realized through execution of the program by a computing unit. Prior to the following steps, the substrate 162 for sample analysis is loaded onto the sample analysis device 200, and an original point of the substrate 162 for sample analysis is detected.

[Step S21]

Figure 20:
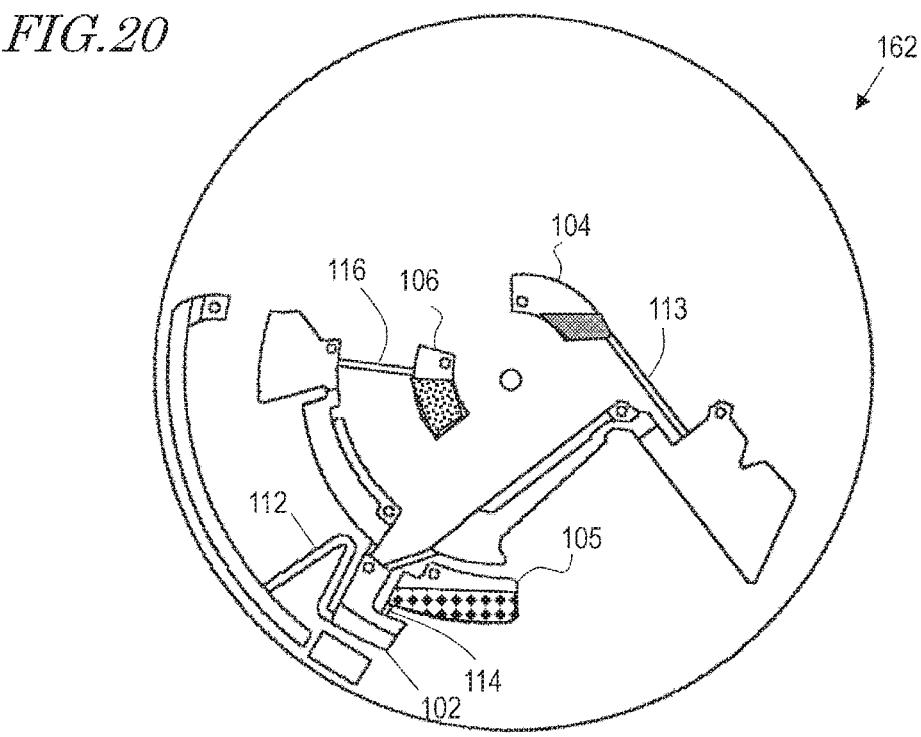
FIG. 20 is a view for schematically illustrating an example of a stopping angle of the substrate for sample analysis and a position of a liquid during operation of the sample analysis system according to the second embodiment.

First, as illustrated in FIG. 20, a washing liquid is introduced into the storage chamber 104 of the substrate 162 for sample analysis, and a substrate solution is introduced into the storage chamber 106. The substrate solution contains a substrate that causes luminescence, fluorescence, or a change in absorption wavelength by the reaction with the labeling substance 307 or the catalytic action of the labeling substance 307. Further, the magnetized particle immobilized antibody 305, the antigen 306, and a specimen containing the labeling antibody 308 are introduced into the reaction chamber 105. For example, a liquid containing the magnetized particle immobilized antibody 305 may be retained in the reaction chamber 105, and liquids containing the antigen 306 and the labeling antibody 308 may be retained in chambers (not shown) arranged in the substrate 162 for sample analysis, respectively. Those liquids may be transported to the reaction chamber 105 with a centrifugal force caused by rotation of the substrate 162 for sample analysis. In the reaction chamber 105, the magnetized particle immobilized antibody 305, the antigen 306 in the specimen, and the labeling antibody 308 are bound to each other by the antigen-antibody reaction, to thereby form the complex 310. At this time, the third flow passage 113 and the fourth flow passage 114 are filled with the washing liquid and the reaction solution containing the complex 310, respectively, through the capillary phenomenon. In an example illustrated in FIG. 20, the sixth flow passage 116 is not filled with the substrate solution. However, the sixth flow passage 116 may be filled with the substrate solution.

[Step S22]

After the complex 310 is generated, the substrate 162 for sample analysis is rotated to cause the reaction solution containing the complex 310 to move to the second chamber 102. In this case, the fourth flow passage 114 is filled with the reaction solution through the capillary phenomenon. Therefore, when a centrifugal force stronger than a capillary force applied to the reaction solution in the fourth flow passage 114 acts on the reaction solution containing the complex 310 in the reaction chamber 105 due to the rotation of the substrate 162 for sample analysis, the reaction solution is transported to the second chamber 102. The reaction solution having been transported to the second chamber 102 is not successively transported to the third chamber 103 under a state in which the substrate 162 for sample analysis is rotated. The reason for this is as follows. The second flow passage 112 forms a siphon as described above, and hence the liquid does not move through the second flow passage 112 in a direction toward the rotation axis 110 against the centrifugal force. In the reaction solution containing the complex 310 having been transported to the second chamber 102, most of the magnetized particles 311 are trapped onto the side surface 102s with an attractive force of the magnet 126.

The rotation speed of the substrate 162 for sample analysis is set so that the liquid, for example, the reaction solution does not move due to gravity when a centrifugal force caused by rotation occurs, and a centrifugal force stronger than a capillary force of each capillary path can be applied. This rotation speed is hereinafter set in rotation using a centrifugal force. In the case of the rotation using a centrifugal force, the substrate 162 for sample analysis may be rotated clockwise or counterclockwise.

Simultaneously with the movement of the reaction solution, the washing liquid is transported from the storage chamber 104 to the first chamber 101 through the third flow passage 113.

Figure 21:
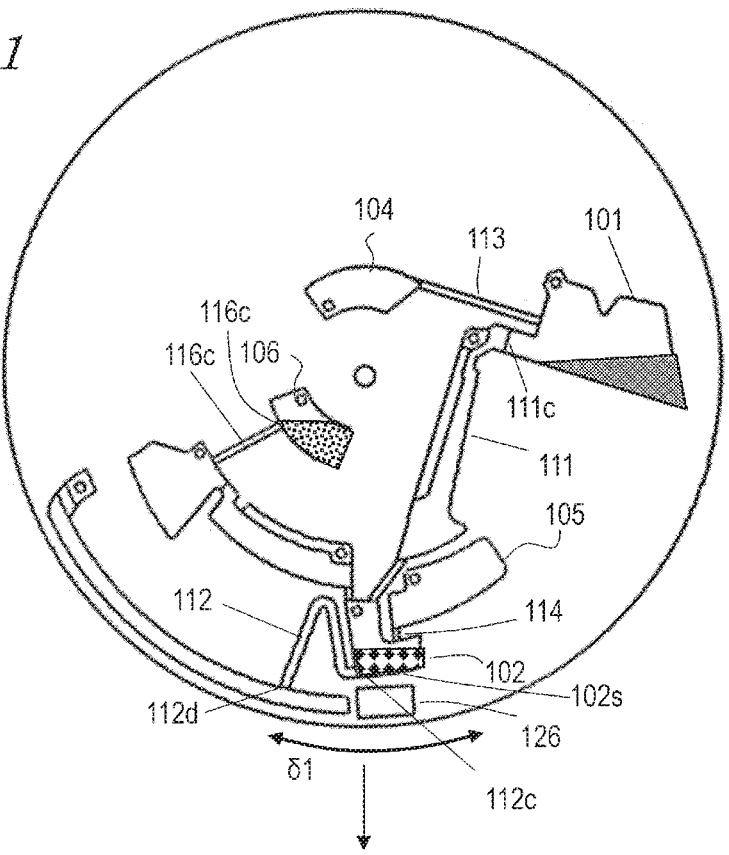
FIG. 21 is a view for schematically illustrating an example of a stopping angle of the substrate for sample analysis and a position of the liquid during operation of the sample analysis system according to the second embodiment.
Figure 22:
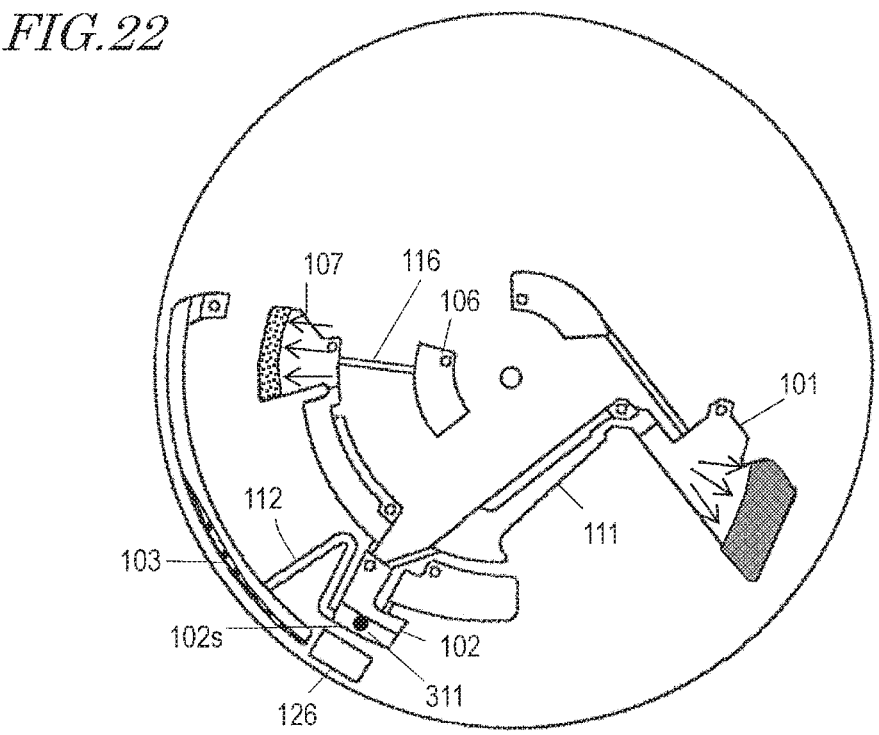
FIG. 22 is a view for schematically illustrating an example of a stopping angle of the substrate for sample analysis and a position of the liquid during operation of the sample analysis system according to the second embodiment.

After the entire reaction solution and washing liquid are transported to the second chamber 102 and the first chamber 101, respectively, the substrate 162 for sample analysis is stopped at a predetermined first angle. As illustrated in FIG. 21, the predetermined first angle refers to an angle at which, in the substrate 162 for sample analysis, the washing liquid having been transported to the first chamber 101 does not pass the first opening 111c of the first flow passage 111 to be brought into contact with the first portion 111a, and the substrate solution in the storage chamber 106 can be brought into contact with the seventh opening 116c of the sixth flow passage 116 and the reaction solution in the second chamber 102 can be brought into contact with the third opening 112c of the second flow passage 112. This angle depends on the shapes of the first chamber 101, the second chamber 102, and the storage chamber 106, the positions thereof in the substrate 162, the amounts of the washing liquid, the substrate solution, and the reaction solution, the inclination angle θ of the substrate 162 for sample analysis, and the like. In an example illustrated in FIG. 21, it is only necessary that the gravity direction (represented by the arrow) in the sample analysis system 501 projected onto a flat plane parallel to the substrate 162 for sample analysis fall within an angle range represented by δ1 of the substrate 162 for sample analysis.

The substrate solution in the storage chamber 106 is brought into contact with the seventh opening 116c of the sixth flow passage 116, thereby being filled into the sixth flow passage 116 through the capillary phenomenon. Further, the reaction solution in the second chamber 102 is brought into contact with the third opening 112c of the second flow passage 112, thereby being filled into the second flow passage 112 through the capillary phenomenon.

[Step S23]

The substrate 162 for sample analysis is rotated. A centrifugal force occurs along with the rotation and acts on the reaction solution in the second chamber 102 and the magnetized particles 311 (complex 310 and unreacted magnetized particles). This centrifugal force acts so that the liquid and the complex 310 move to the side surface 102s side of the second chamber 102. Therefore, the magnetized particles 311 are pressed against the side surface 102s.

The reaction solution having received the centrifugal force is discharged from the second flow passage 112 and transported to the third chamber 103. The magnetized particles 311 are strongly pressed against the side surface 102s and trapped thereon through the combination of the centrifugal force and the attractive force of the magnet 126.

As a result, only the reaction solution is discharged from the second flow passage 112 to the third chamber 103, and the magnetized particles 311 remain in the second chamber 102. The washing liquid in the first chamber 101 receives a centrifugal force caused by rotation. However, the washing liquid is pressed against a side surface of the first chamber 101 farthest from the rotation axis 110 and hence remains in the first chamber 101.

The substrate solution in the storage chamber 106 and the sixth flow passage receives a centrifugal force caused by rotation to move to the fourth camber 107. The substrate solution having moved to the fourth chamber 107 is pressed against a side surface of the fourth chamber 107 farthest from the rotation axis 110 with the centrifugal force. Therefore, the substrate solution remains in the fourth chamber 107.

After the transportation of the reaction solution to the third chamber 103 and the transportation of the substrate solution to the fourth chamber 107 are completed, the rotation of the substrate 162 for sample analysis is stopped.

With this, the reaction solution and the magnetized particles 311 are separated. Specifically, the reaction solution moves to the third chamber 103, and the magnetized particles 311 remain in the second chamber 102. Even when the rotation of the substrate 162 for sample analysis is stopped, the magnetized particles 311 may keep a state of aggregating on the side surface 102s due to the attractive force from the magnet 126. The stopping angle in this case may be the first angle, a second angle in a next step, or other angles.

[Step S24 (Step (a))]

Figure 23:
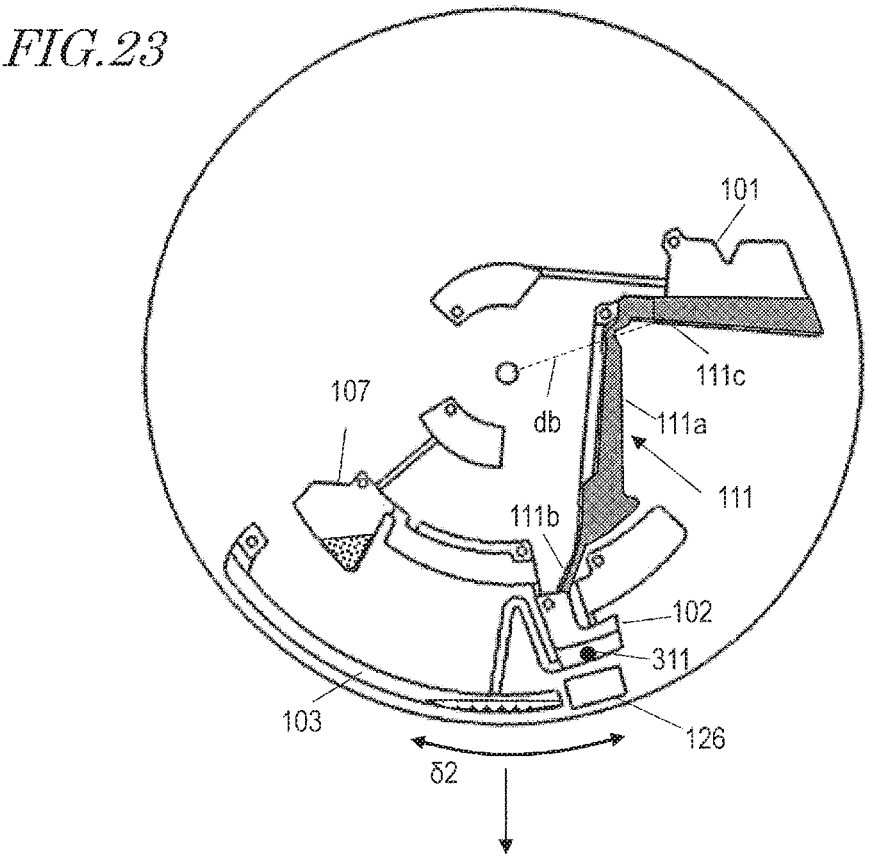
FIG. 23 is a view for schematically illustrating an example of a stopping angle of the substrate for sample analysis and a position of the liquid during operation of the sample analysis system according to the second embodiment.

As illustrated in FIG. 23, when the substrate 162 for sample analysis is not stopped at the second angle in the previous step, the substrate 162 for sample analysis is slightly rotated counterclockwise and stopped at a predetermined second angle. The second angle refers to an angle at which the washing liquid having been transported to the first chamber 101 is brought into contact with the first opening 111c of the first flow passage 111. For example, in an example illustrated in FIG. 23, the second angle is an angle at which the gravity direction is positioned within an angle range represented by δ2 of the substrate 162 for sample analysis.

When the washing liquid is brought into contact with the first portion 111a of the first flow passage 111 through the first opening 111c, the washing liquid is sucked into the entire first portion 111a with the capillary force, and the first portion 111a and the second portion 111b of the first flow passage 111 are filled with the washing liquid. With this, the washing liquid for one time of washing is weighed.

The substrate 162 for sample analysis may be rotated, that is, shaken several times alternately clockwise or counterclockwise with respect to the second angle so that the first flow passage 111 is filled with the washing liquid reliably. The capillary force acts on the first flow passage 111, and hence the washing liquid does not move from the second portion 111b of the first flow passage 111 to the second chamber 102 in this case.

[Step S25 (Steps (b) and (c))]

Figure 24:
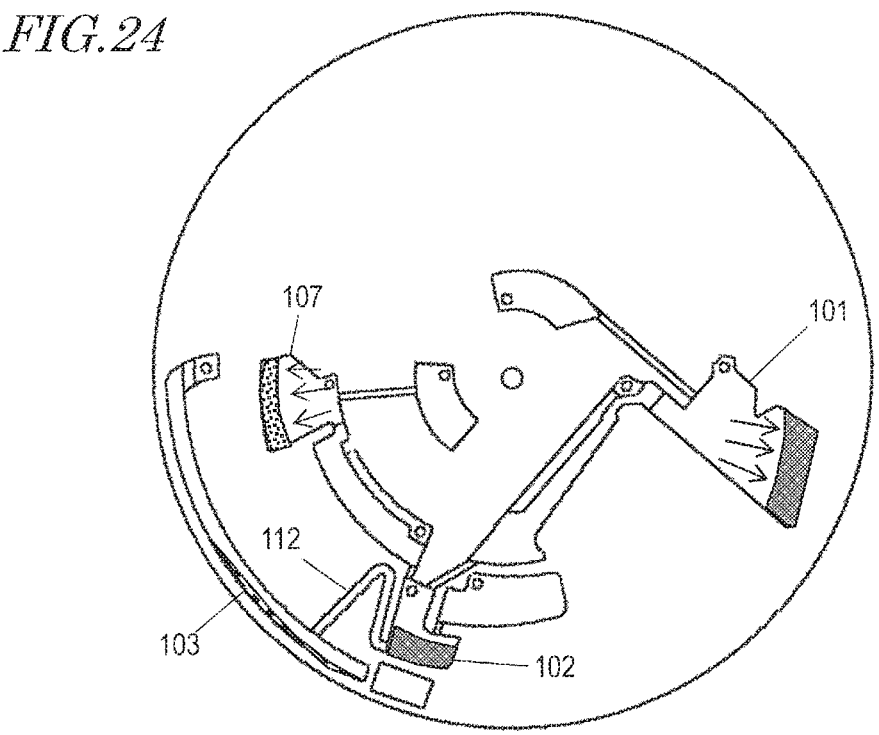
FIG. 24 is a view for schematically illustrating an example of a stopping angle of the substrate for sample analysis and a position of the liquid during operation of the sample analysis system according to the second embodiment.

Subsequently, the substrate 162 for sample analysis is rotated. The centrifugal force caused by the rotation acts on the washing liquid in the first flow passage 111 and the first chamber 101. As described with reference to FIG. 17A, the washing liquid positioned on the first flow passage 111 side based on the straight line db illustrated in FIG. 23 moves to the second chamber 102 through the first flow passage 111. Further, the washing liquid positioned on the first chamber 101 side based on the straight line db is returned to the first chamber 101 with the centrifugal force. Thus, as illustrated in FIG. 24, only the washing liquid weighed with the first flow passage 111 is transported to the second chamber 102.

The centrifugal force also acts on the washing liquid having been transported to the second chamber 102, and hence the washing liquid remains substantially in the second chamber 102 without moving toward the rotation axis 110 in the second flow passage 112. With this, the magnetized particles 311 in the second chamber 102 are brought into contact with the washing liquid and subjected to the first washing.

The substrate solution is pressed against a side surface of the fourth chamber 107 positioned farthest from the rotation axis 110 with the centrifugal force. Therefore, the substrate solution remains in the fourth chamber 107.

Figure 25:
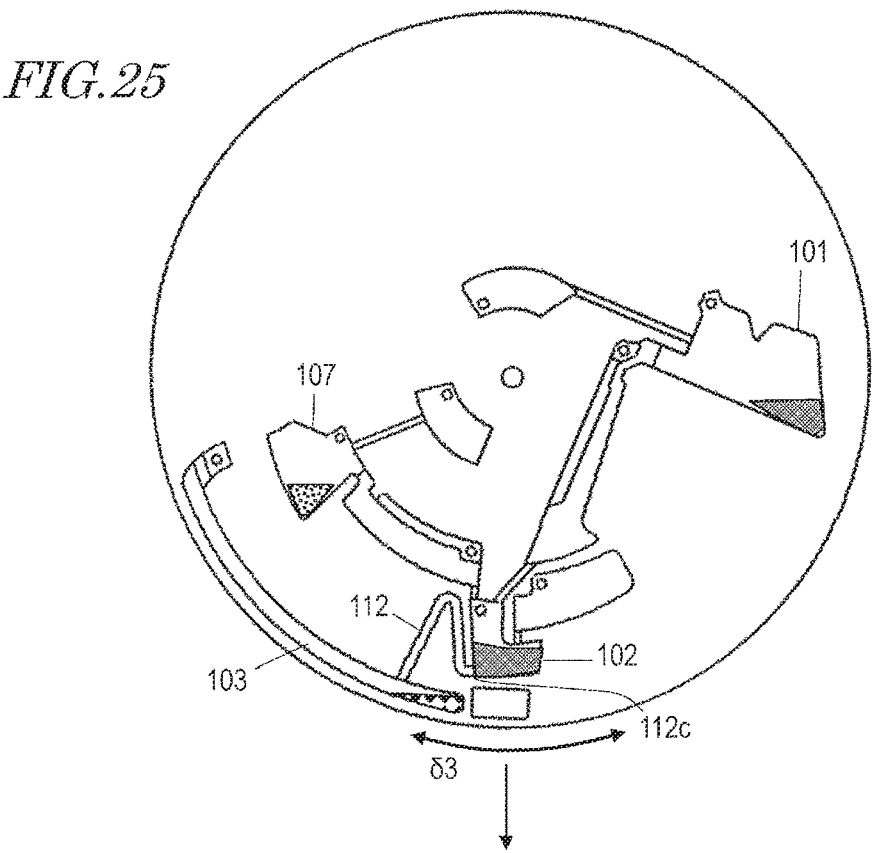
FIG. 25 is a view for schematically illustrating an example of a stopping angle of the substrate for sample analysis and a position of the liquid during operation of the sample analysis system according to the second embodiment.

As illustrated in FIG. 25, after the entire washing liquid in the first flow passage 111 has moved to the second chamber 102, the substrate 162 for sample analysis is stopped at a predetermined third angle. The third angle refers to an angle at which the washing liquid in the first chamber 101 is not brought into contact with the first opening 111c, and the washing liquid having been shifted to the second chamber 102 can be brought into contact with the third opening 112c of the second flow passage 112. For example, in an example illustrated in FIG. 25, it is only necessary that the gravity direction in the sample analysis system 501 projected onto a flat plane parallel to the substrate 162 for sample analysis fall within an angle range represented by 63 of the substrate 162 for sample analysis.

The reaction solution in the second chamber 102 is brought into contact with the third opening 112c of the second flow passage 112, thereby being filled into the second flow passage 112 through the capillary phenomenon.

[Step S26 (Step (d))]

The substrate 162 for sample analysis is rotated. A centrifugal force occurs along with the rotation and acts on washing liquid in the second chamber 102 and the magnetized particles 311. This centrifugal force acts so that the washing liquid and the magnetized particles 311 move to the side surface 102s side of the second chamber 102, and the magnetized particles 311 are trapped onto the side surface 102s with the centrifugal force and the attractive force of the magnet 126.

The washing liquid having received the centrifugal force is discharged from the second flow passage 112 and transported to the third chamber 103.

Figure 26:
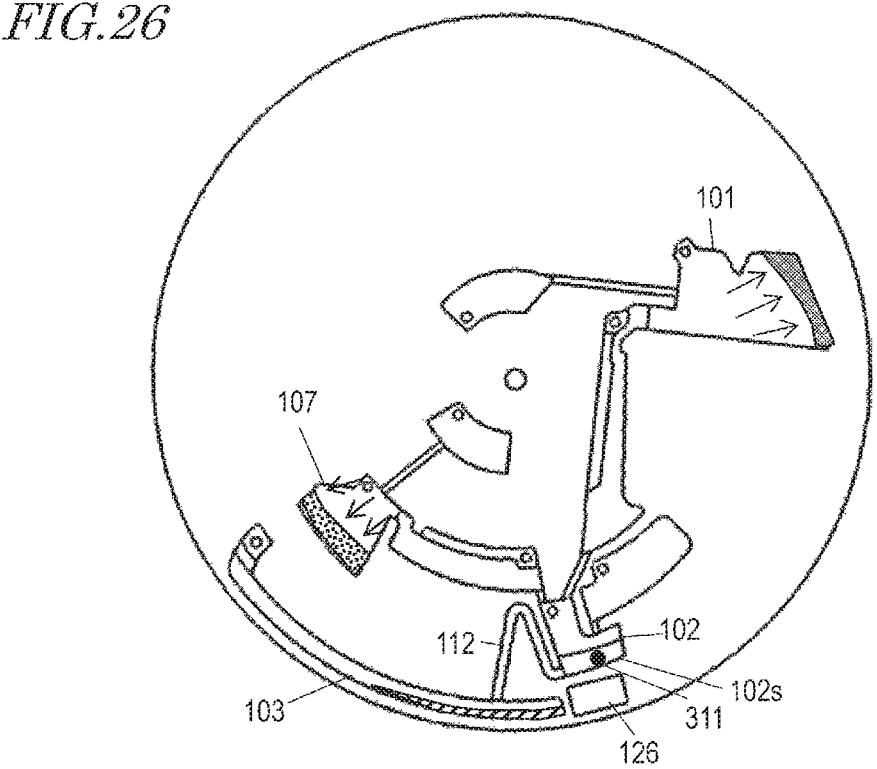
FIG. 26 is a view for schematically illustrating an example of a stopping angle of the substrate for sample analysis and a position of the liquid during operation of the sample analysis system according to the second embodiment.

Thus, as illustrated in FIG. 26, only the washing liquid is discharged from the second flow passage 112, and the magnetized particles 311 remain in the second chamber 102. The washing liquid in the first chamber 101 is pressed against a side surface positioned farthest from the rotation axis 110 and remains in the first chamber 101.

After the transportation of the washing liquid to the third chamber 103 is completed, the rotation of the substrate 162 for sample analysis is stopped. With this, the washing liquid and the magnetized particles 311 are separated. Specifically, the washing liquid moves to the third chamber 103, and the magnetized particles 311 remain in the second chamber 102. Even when the rotation of the substrate 162 for sample analysis is stopped, the magnetized particles 311 may keep a state of aggregating on the side surface 102s due to the attractive force from the magnet 126. The stopping angle in this case may be the third angle or a fourth angle in a next step.

[Step S27 (Step (e))]

Figure 27:
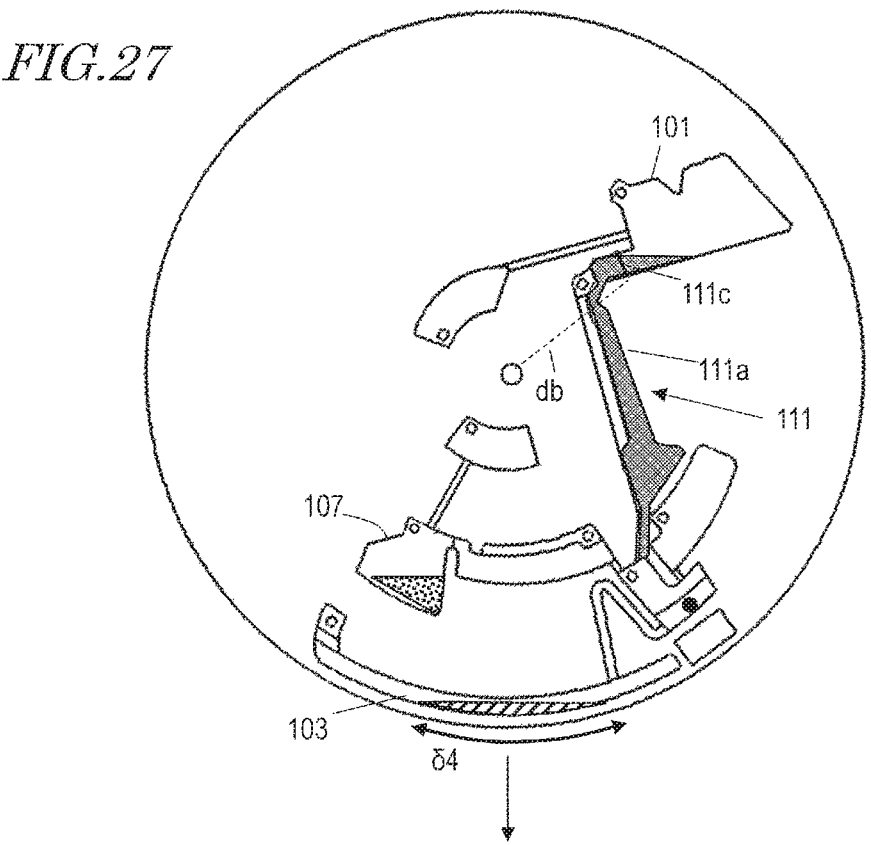
FIG. 27 is a view for schematically illustrating an example of a stopping angle of the substrate for sample analysis and a position of the liquid during operation of the sample analysis system according to the second embodiment.

As illustrated in FIG. 27, when the substrate 162 for sample analysis is not stopped at the fourth angle in the previous step, the substrate 162 for sample analysis is slightly rotated counterclockwise and stopped at a predetermined fourth angle. The fourth angle refers to an angle at which the washing liquid having been transported to the first chamber 101 is brought into contact with the first opening 111c of the first flow passage 111. For example, in an example illustrated in FIG. 27, the fourth angle is an angle at which the gravity direction is positioned within an angle range represented by δ4 of the substrate 162 for sample analysis. The amount of the washing liquid remaining in the first chamber 101 is different from that in Step S4, and hence the angle range δ4 may be different from the angle range δ2.

The washing liquid is sucked from the first chamber 101 into the first flow passage 111 with the capillary force in the first portion 111a of the first flow passage 111, and the first portion 111a and the second portion 111b of the first flow passage 111 are filled with the washing liquid. With this, the washing liquid for one time of washing is weighed again.

The substrate 162 for sample analysis may be shaken with respect to the fourth angle so that the first flow passage 111 is filled with the washing liquid reliably. The capillary force acts on the first flow passage 111, and hence the washing liquid does not move from the first flow passage 111 to the second chamber 102 in this case.

[Step S28 (Steps (f) and (g))]

Figure 28:
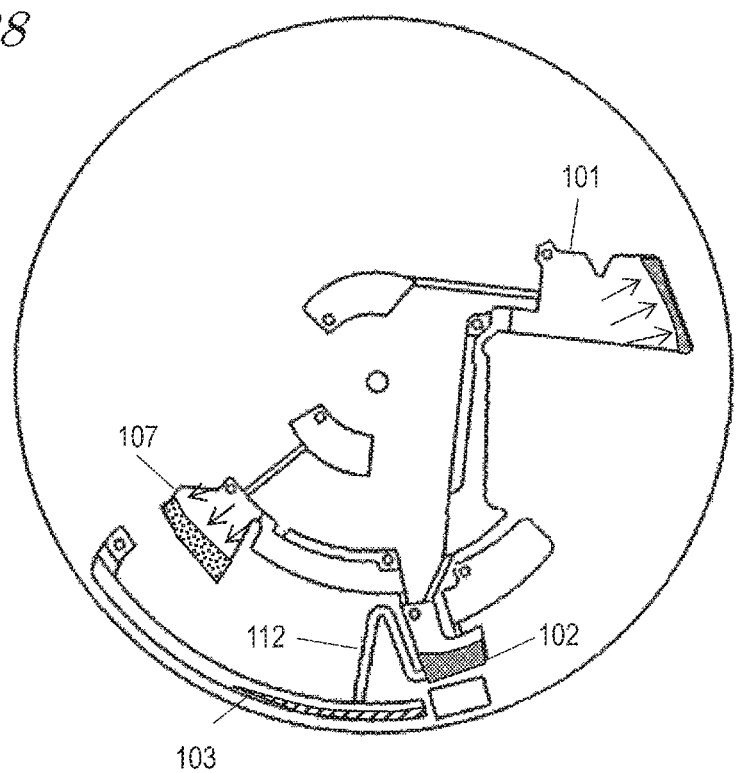
FIG. 28 is a view for schematically illustrating an example of a stopping angle of the substrate for sample analysis and a position of the liquid during operation of the sample analysis system according to the second embodiment.

Subsequently, the substrate 162 for sample analysis is rotated. The centrifugal force caused by the rotation acts on the washing liquid in the first flow passage 111 and the first chamber 101. Similarly to the first washing, the washing liquid positioned on the first flow passage 111 side based on the straight line db illustrated in FIG. 27 moves to the second chamber 102 through the first flow passage 111. Further, the washing liquid positioned on the first chamber 101 side based on the straight line db is returned to the first chamber 101 with the centrifugal force. Thus, as illustrated in FIG. 28, only the washing liquid weighed with the first flow passage 111 is transported to the second chamber 102. The centrifugal force also acts on the washing liquid having been transported to the second chamber 102, and hence the washing liquid remains substantially in the second chamber 102 without moving toward the rotation axis 110 in the second flow passage 112. With this, the magnetized particles 311 in the second chamber 102 are brought into contact with the washing liquid and subjected to the second washing.

The substrate solution is pressed against a side surface of the fourth chamber 107 positioned farthest from the rotation axis 110 with the centrifugal force. Therefore, the substrate solution remains in the fourth chamber 107.

Figure 29:
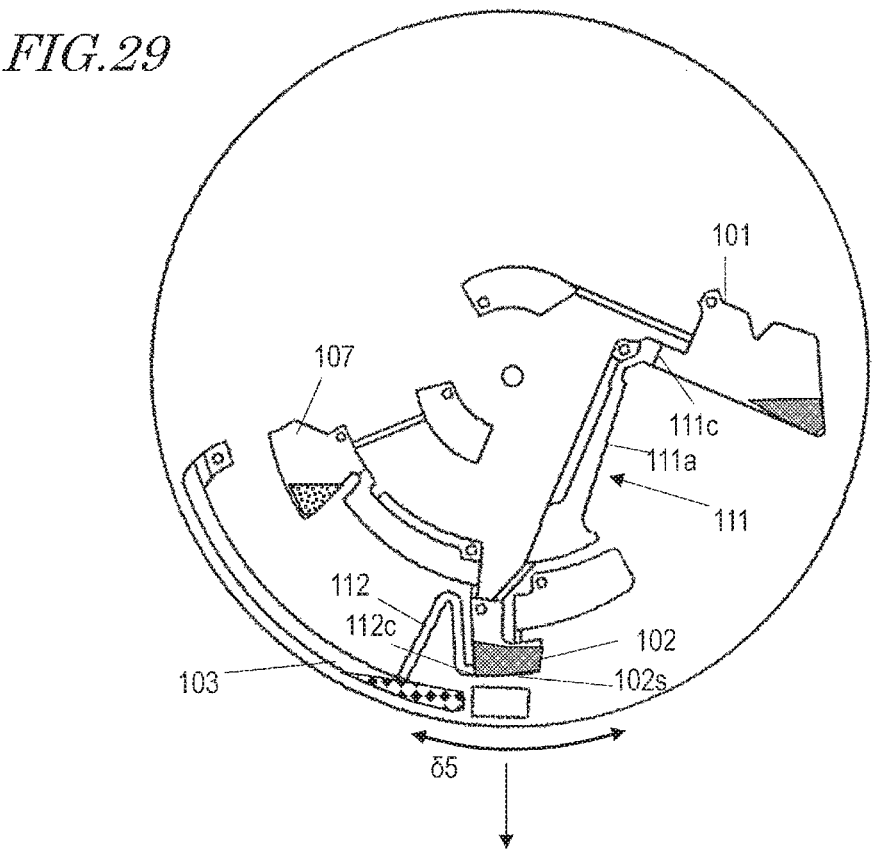
FIG. 29 is a view for schematically illustrating an example of a stopping angle of the substrate for sample analysis and a position of the liquid during operation of the sample analysis system according to the second embodiment.

As illustrated in FIG. 29, after the entire washing liquid in the first flow passage 111 has moved to the second chamber 102, the substrate 162 for sample analysis is stopped at a predetermined fifth angle. The fifth angle refers to an angle at which the washing liquid in the first chamber 101 is not brought into contact with the first opening 111c, and the washing liquid having been shifted to the second chamber 102 can be brought into contact with the third opening 112c of the second flow passage 112. For example, in an example illustrated in FIG. 29, it is only necessary that the gravity direction in the sample analysis system 501 projected onto a flat plane parallel to the substrate 162 for sample analysis fall within an angle range represented by 65 of the substrate 162 for sample analysis.

The washing liquid in the second chamber 102 is brought into contact with the third opening 112c of the second flow passage 112, thereby being filled into the second flow passage 112 through the capillary phenomenon.

[Step S29 (Step (h))]

The substrate 162 for sample analysis is rotated. A centrifugal force occurs along with the rotation and acts on washing liquid in the second chamber 102 and the magnetized particles 311. This centrifugal force acts so that the washing liquid and the magnetized particles 311 move to the side surface 102s side of the second chamber 102, and the magnetized particles 311 are trapped onto the side surface 102s with the centrifugal force and the attractive force of the magnet 126.

The washing liquid having received the centrifugal force is discharged from the second flow passage 112 and transported to the third chamber 103.

Figure 30:
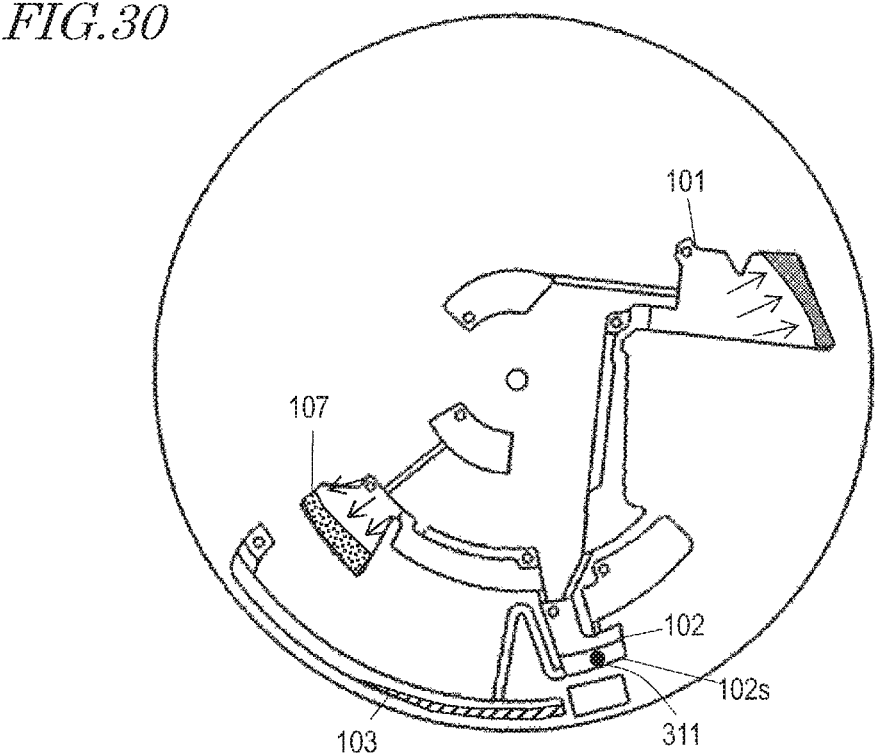
FIG. 30 is a view for schematically illustrating an example of a stopping angle of the substrate for sample analysis and a position of the liquid during operation of the sample analysis system according to the second embodiment.

Thus, as illustrated in FIG. 30, only the washing liquid is discharged from the second flow passage 112, and the magnetized particles 311 remain in the second chamber 102. The washing liquid in the first chamber 101 is pressed against a side surface positioned farthest from the rotation axis 110 and remains in the first chamber 101.

Figure 31:
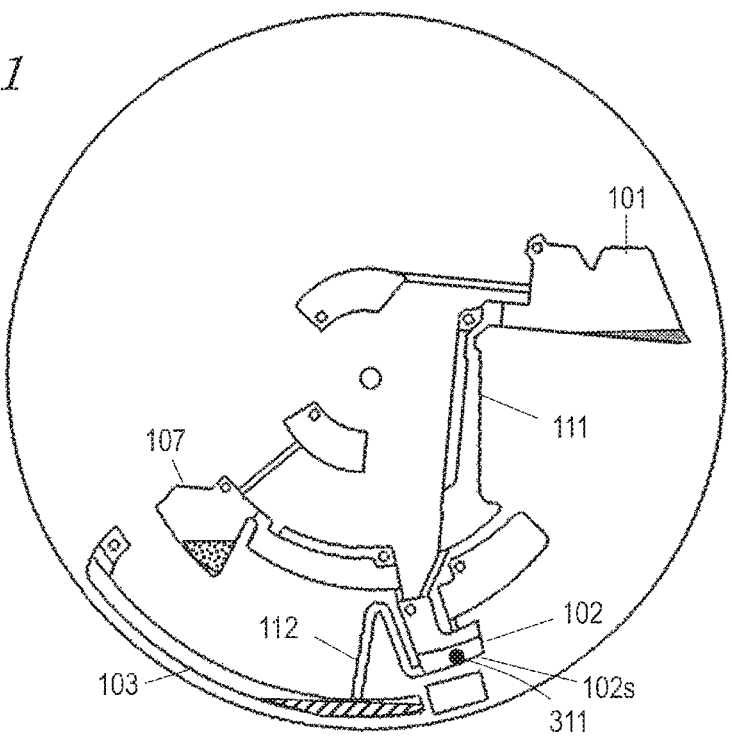
FIG. 31 is a view for schematically illustrating an example of a stopping angle of the substrate for sample analysis and a position of the liquid during operation of the sample analysis system according to the second embodiment.

After the transportation of the washing liquid to the third chamber 103 is completed, the rotation of the substrate 162 for sample analysis is stopped. With this, as illustrated in FIG. 31, the washing liquid and the magnetized particles 311 are separated. Specifically, the washing liquid moves to the third chamber 103, and the magnetized particles 311 remain in the second chamber 102. Even when the rotation of the substrate 162 for sample analysis is stopped, the magnetized particles 311 may keep a state of aggregating on the side surface 102s due to the attractive force from the magnet 126. The stopping angle in this case may be the fifth angle or a sixth angle in a next step.

[Step S30 (Step (i))]

Figure 32:
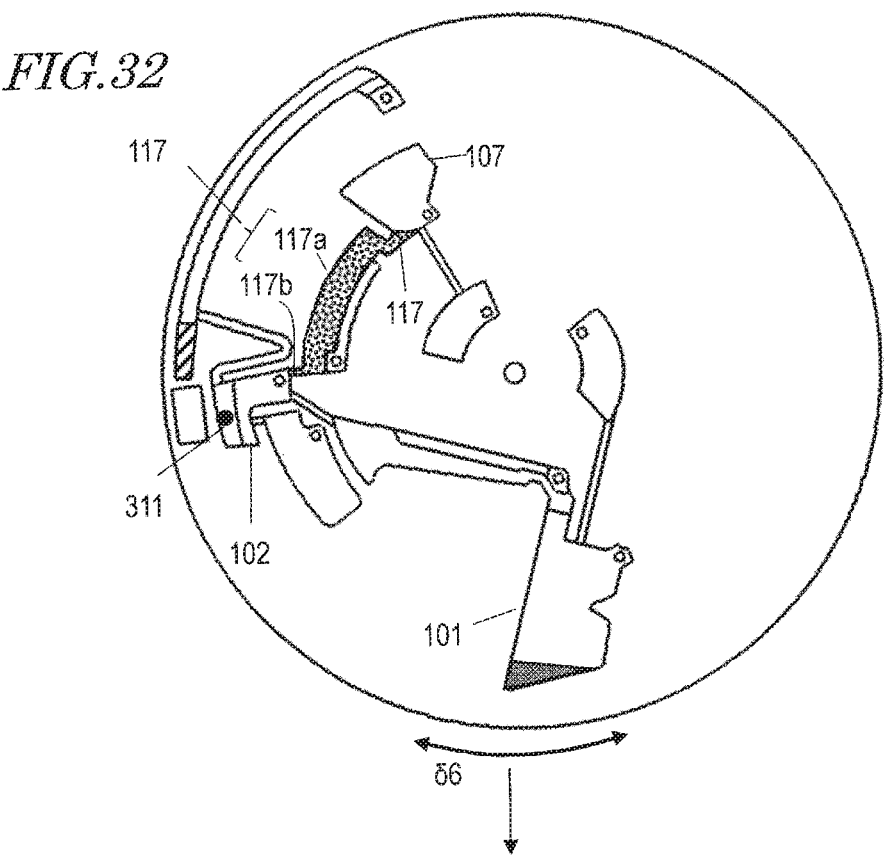
FIG. 32 is a view for schematically illustrating an example of a stopping angle of the substrate for sample analysis and a position of the liquid during operation of the sample analysis system according to the second embodiment.

As illustrated in FIG. 32, when the substrate 162 for sample analysis is not stopped at the sixth angle in the previous step, the substrate 162 for sample analysis is slightly rotated and stopped at the predetermined sixth angle. Unlike the foregoing procedure, in this case, the substrate 162 for sample analysis is rotated clockwise. The sixth angle refers to an angle at which the substrate solution having been transported to the fourth chamber 107 is brought into contact with the ninth opening 117c of the seventh flow passage 117. For example, in an example illustrated in FIG. 32, the sixth angle is an angle at which the gravity direction is positioned within an angle range represented by 66 of the substrate 162 for sample analysis.

When the substrate solution in the fourth chamber 107 is brought into contact with the first portion 117a of the seventh flow passage 117 through the ninth opening 117c, the substrate solution is sucked into the entire first portion 117a with a capillary force, and the first portion 117a and the second portion 117b of the seventh flow passage 117 are filled with the substrate solution. With this, the substrate solution is weighed.

The substrate 162 for sample analysis may be rotated, that is, shaken several times alternately clockwise or counterclockwise with respect to the sixth angle so that the seventh flow passage 117 is filled with the washing liquid reliably. The capillary force acts on the seventh flow passage 117, and hence the washing liquid does not move from the second portion 117b of the seventh flow passage 117 to the second chamber 102 in this case.

[Step S31 (Step (j))]

Subsequently, the substrate 162 for sample analysis is rotated. The centrifugal force caused by the rotation acts on the substrate solution in the seventh flow passage 117 and the fourth chamber 107. The substrate solution in the seventh flow passage 117 is transported to the second chamber 102 with the centrifugal force. The substrate solution positioned on the fourth chamber 107 side with respect to the ninth opening 117c is pressed against a side surface of the fourth chamber 107 positioned farthest from the rotation axis 110 with a centrifugal force, thereby being retained in the fourth chamber 107.

The substrate solution having moved to the second chamber 102 contains a substrate. This substrate causes luminescence, fluorescence, or a change in absorption wavelength by the reaction with the labeling substance 307 contained in the labeling antibody 308 in the magnetized particles 311 retained in the second chamber 102 or by the catalytic action of the labeling substance 307.

Figure 33:
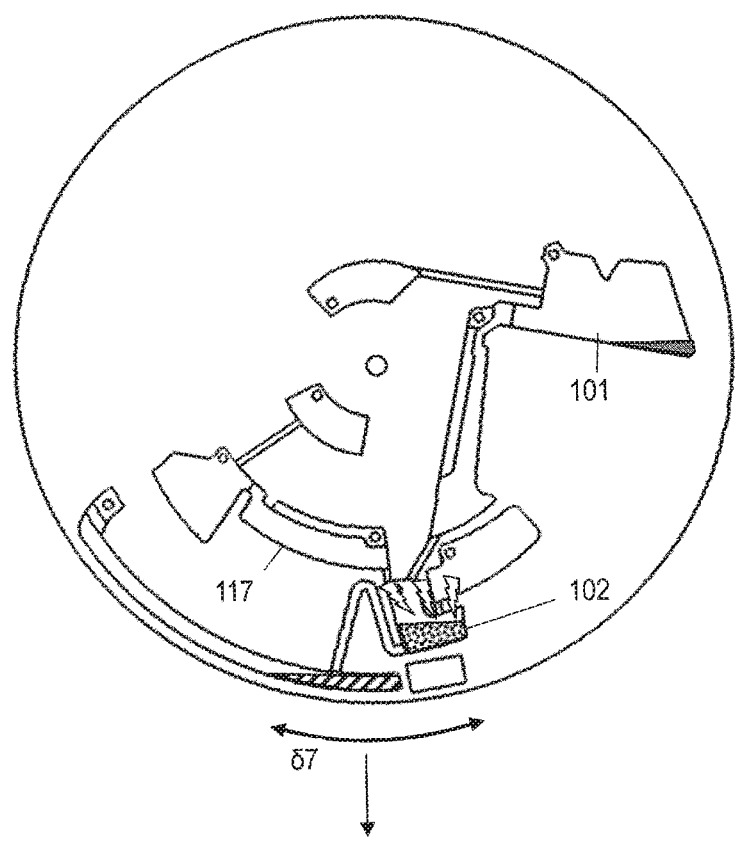
FIG. 33 is a view for schematically illustrating an example of a stopping angle of the substrate for sample analysis and a position of the liquid during operation of the sample analysis system according to the second embodiment.

After the transportation of the substrate solution to the second chamber 102 is completed, the rotation of the substrate 162 for sample analysis is stopped at a seventh angle as illustrated in FIG. 33. The seventh angle refers to an angle at which the second chamber 102 is arranged with a predetermined positional relationship with the optical measurement unit 207 so that a light receiving element of the optical measurement unit 207 can detect luminescence, fluorescence, or a change in absorption wavelength of the substrate in the second chamber 102 when the light receiving element of the optical measurement unit 207 is brought close to the second chamber 102.

[Step S32 (Step (k))]

The optical measurement unit 207 is configured to perform optical measurement of a liquid retained in the second chamber 102. Specifically, the optical measurement unit 207 is configured to detect signals such as a dye, luminescence, fluorescence, and the like of the substrate in accordance with the labeling substance 307 of the labeling antibody 308 bound in the complex 310 contained in the magnetized particles 311. With this, the detection of the antigen 306, the quantitative determination of a concentration of the antigen 306, and the like can be performed.

The optical measurement by the optical measurement unit 207 may be performed under a state in which the substrate 162 for sample analysis is rotated. In this case, in Step S31, after the transportation of the substrate solution to the second chamber 102 is completed, signals such as a dye, luminescence, fluorescence, and the like of the substrate may be detected under a state in which the substrate 162 for sample analysis is rotated. In this case, it is preferred that the substrate 162 for sample analysis be rotated at a rotation speed at which a centrifugal force weaker than a capillary force acts on the liquid in the second flow passage 112. The reason for this is as follows. When a centrifugal force stronger than a capillary force acts on the liquid in the second flow passage 112 due to the rotation of the substrate 162 for sample analysis, the substrate solution in the second chamber 102 is transported to the third chamber 103 through the second flow passage 112, with the result that the measurement may not be performed.

Other Mode Examples of Substrate 162 for Sample Analysis

Figure 34:
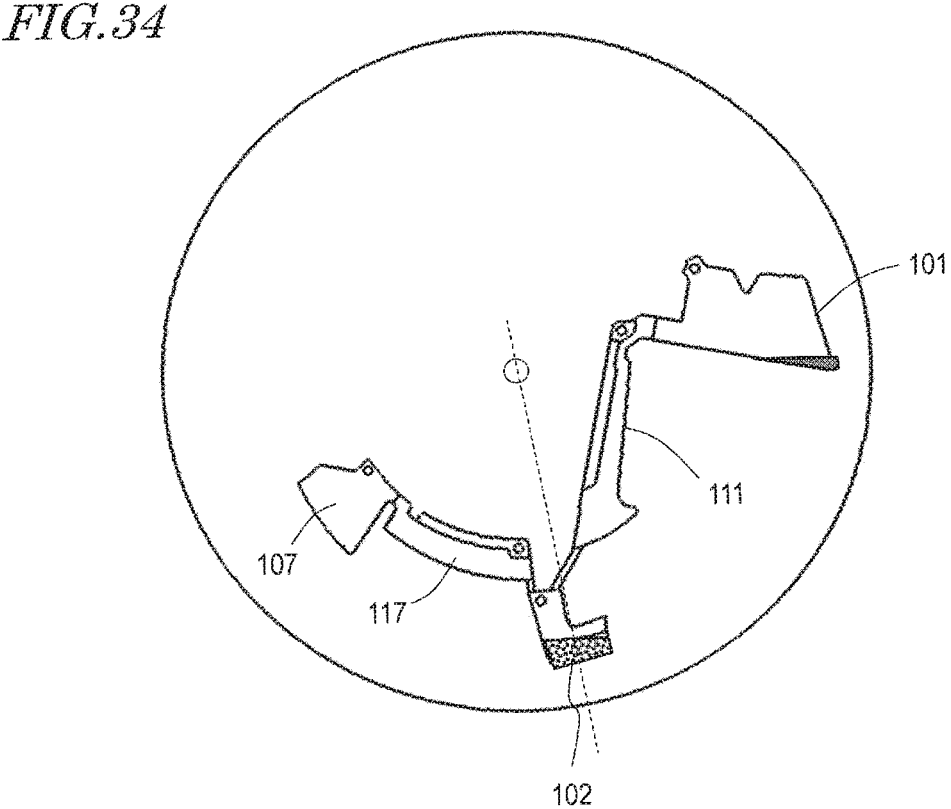
FIG. 34 is a plan view for illustrating another example of the substrate for sample analysis.
Figure 35:
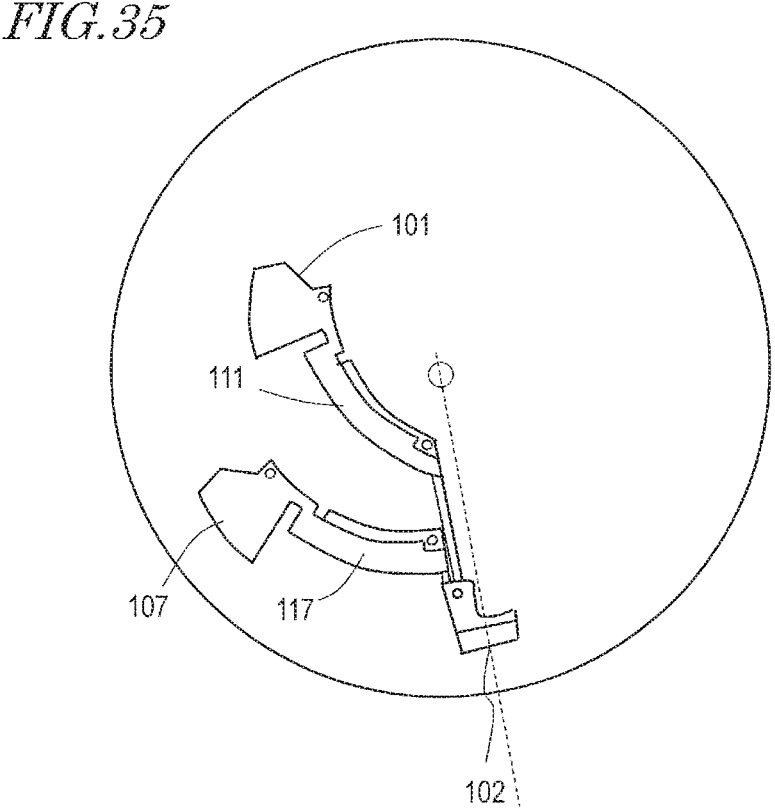
FIG. 35 is a plan view for illustrating another example of the substrate for sample analysis.

Now, other mode examples of the substrate 162 for sample analysis are described. FIG. 34 and FIG. 35 are each a view for illustrating another configuration example of the first chamber 101, the second chamber 102, the fourth chamber 107, the first flow passage 111, and the seventh flow passage 117 of the substrate 162 for sample analysis. For ease of understanding, in those figures, only the rotation axis 110, the first chamber 101, the second chamber 102, the fourth chamber 107, the first flow passage 111, and the seventh flow passage 117 in the substrate 162 for sample analysis are illustrated.

In the first example illustrated in FIG. 34, the first chamber 101 and the fourth chamber 107 are positioned on opposite sides with respect to the second chamber 102. Specifically, the first chamber 101 and the fourth chamber 107 are arranged, respectively, in two regions divided by a straight line (represented by the broken line) connecting a vicinity of a center of the second chamber 102 and the rotation axis 110 to each other. In the first example, the washing liquid retained in the first chamber 101 can be introduced into the first flow passage 111 to be weighed and moved to the second chamber 102 in divided portions by, for example, rotating the substrate for sample analysis counter-clockwise. It is possible to maintain a state in which the substrate solution is retained in the fourth chamber 107 by appropriately selecting an angle at which the substrate for sample analysis is stopped for introducing the washing liquid into the first flow passage 111.

Meanwhile, the substrate solution retained in the fourth chamber 107 can be introduced into the seventh flow passage 117 to be weighed and moved to the second chamber 102 by rotating the substrate for sample analysis clockwise. In this case, it is possible to maintain a state in which the washing liquid is retained in the first chamber 101 by appropriately selecting an angle at which the substrate for sample analysis is stopped.

In an example illustrated in FIG. 34, the substrate for sample analysis is rotated counterclockwise so as to move the washing liquid. However, when the positions of the first chamber 101 and the fourth chamber 107 are reversed, it is only necessary that the rotation direction of the substrate for sample analysis be reversed.

Thus, in the first example, the washing liquid in the first chamber 101 can be transported to the second chamber 102 in divided portions while the substrate solution is retained in the fourth chamber 107 by rotating the substrate for sample analysis in the same direction (anti-clockwise in the example of FIG. 34). Further, the substrate solution can be transported to the second chamber 102 while the washing liquid is retained in the first chamber 101 by rotating the substrate for sample analysis in an opposite direction.

In the second example illustrated in FIG. 35, the first chamber 101 and the fourth chamber 107 are positioned on the same side with respect to the second chamber 102. Specifically, both the first chamber 101 and the fourth chamber 107 are arranged only in one of two regions divided by a straight line (represented by the broken line) connecting a vicinity of a center of the second chamber 102 and the rotation axis 110 to each other.

In the example illustrated in FIG. 35, when the substrate for sample analysis is rotated clockwise from a state in which the first chamber 101 and the fourth chamber 107 are positioned below in the gravity direction, the washing liquid retained in the first chamber 101 is first brought into contact with the first flow passage 111. When the substrate for sample analysis is further rotated, the substrate solution in the fourth chamber 107 is brought into contact with the seventh flow passage 117.

Therefore, when the substrate for sample analysis is rotated clockwise from the state in which the first chamber 101 and the fourth chamber 107 are positioned below in the gravity direction and stopped at an angle at which the washing liquid is brought into contact with the first flow passage 111, and the substrate solution is not brought into contact with the seventh flow passage 117, the washing liquid in the first chamber 101 can be weighed and transported to the second chamber 102 in divided portions while the substrate solution is retained in the fourth chamber 107.

Further, when the substrate for sample analysis is rotated clockwise from the state in which the first chamber 101 and the fourth chamber 107 are positioned below in the gravity direction and stopped at an angle at which the substrate solution is brought into contact with the seventh flow passage 117, after the entire washing liquid in the first chamber 101 has been transported, the substrate solution can be moved from the fourth chamber 107 to the seventh flow passage 117 to be weighed with the seventh flow passage 117 and moved to the second chamber 102.

Thus, in the second example, the washing liquid in the first chamber 101 can be transported to the second chamber 102 in divided portions while the substrate solution is retained in the fourth chamber 107 by rotating the substrate for sample analysis in the same direction (clockwise in the example of FIG. 35). Further, after the entire washing liquid in the first chamber 101 has been transported to the second chamber 102, the substrate for sample analysis is rotated in the same direction, thereby being capable of transporting the substrate solution to the second chamber 102.

In those embodiments, description is given assuming the measurement system using magnetized particles. However, the substrate for sample analysis, the sample analysis device, the sample analysis system, and the program for a sample analysis system according to one embodiment of the present invention are not limited to the measurement system using magnetized particles. For example, an object onto which a primary antibody is immobilized may be a wall surface in a chamber instead of a magnetized particle. That is, when the chamber is made of a material, for example, polystyrene or polycarbonate, the primary antibody can be immobilized onto the wall surface in the chamber through physical adsorption, and a sandwich-type binding reaction can be performed between the primary antibody, and the antigen and the labeling antibody in the chamber. Further, the wall surface in the chamber may have a functional group (for example, an amino group or a carboxyl group) capable of binding to the primary antibody, and the primary antibody can be immobilized onto the wall surface through chemical bonding, with the result that a sandwich-type binding reaction can be performed between the primary antibody, and the antigen and the labeling antibody in the chamber. In a configuration including a metal substrate on the wall surface in the chamber, the primary antibody can be immobilized onto the wall surface so as to bind to the metal substrate through use of, for example, SAM, and a sandwich-type binding reaction can be performed between the primary antibody, and the antigen and the labeling antibody in the chamber. When the primary antibody is immobilized onto the wall surface of the chamber through physical adsorption or chemical bonding, the present invention is used mainly in a system configured to detect signals such as a dye, chemiluminescence, or fluorescence. Meanwhile, when the primary antibody is immobilized onto a metal substrate, the present invention is used mainly in a system configured to detect an electrochemical signal (for example, a current) and an electrochemiluminescent signal. In this case, the magnet 126 illustrated in FIG. 3B is not required. Further, the second chamber 102, instead of the reaction chamber 105, serves as a reaction site for forming the complex 310. Thus, it is necessary that the primary antibody be immobilized onto the wall surface of the second chamber 102.

Further, the substrate for sample analysis, the sample analysis device, the sample analysis system, and the program for a sample analysis system of this disclosure are also applicable to a competitive method and a gene detection method using hybridization, as well as a non-competitive method (sandwich immunoassay method).

In the above-mentioned embodiments, description is given of an example of washing of the B/F separation. However, the substrate for sample analysis, the sample analysis device, and the sample analysis system according to those embodiments are applicable to various sample analysis methods involving introducing a solution other than the washing liquid to the same chamber in divided portions as described above. Further, in the above-mentioned embodiments, the introduction of a liquid into a chamber is continuously performed. However, other steps may be included by appropriately performing control of rotation and stoppage of the substrate for sample analysis and control of an angle at a time of stopping.

Further, in the above-mentioned embodiments, washing is performed twice but may be performed three or more times as necessary.

INDUSTRIAL APPLICABILITY

The substrate for sample analysis, the sample analysis device, the sample analysis system, and the program for a sample analysis system disclosed in the present application are applicable to the analysis of a specific component in a specimen through use of various reactions.

REFERENCE SIGNS LIST 100 substrate for sample analysis
100' substrate
100a base substrate
100b cover substrate
101 first chamber
101a first region
101a' first region
101b second region
101c connecting portion
101d opening
102 second chamber
102a first region
102b second region
102s side surface
103 third chamber
103A first sub-chamber
103B second sub-chamber
104 storage chamber
105 reaction chamber
108 air hole
109 opening
110 rotation axis
111 first flow passage
111a first portion
111b second portion
111c first opening
111d second opening
112 second flow passage
112a first bent portion
112b second bent portion
113 third flow passage
114 fourth flow passage
114a first bent portion
114b second bent portion
115 fifth flow passage
116 magnet
150 substrate for sample analysis
200 sample analysis device
201 motor
201a turntable
203 original point detector
204 rotation angle detection circuit
205 control circuit
206 drive circuit
207 optical measurement unit
302 magnetized particle
304 primary antibody
305 magnetized particle immobilized antibody
306 antigen
307 labeling substance
308 labeling antibody
310 complex
311 magnetized particle
501 sample analysis system

The invention claimed is:

1. A substrate for sample analysis, which involves transportation of a liquid through rotational motion, the substrate for sample analysis comprising a substrate including a rotation axis; a first chamber, which is positioned in the substrate and includes a first space configured to retain the liquid; a second chamber, which is positioned in the substrate and includes a second space configured to retain the liquid discharged from the first chamber; and a first flow passage, which is positioned in the substrate, includes a path configured to connect the first chamber and the second chamber to each other, and is capable of being filled with the liquid retained in the first space through a capillary phenomenon, wherein the first flow passage has a first opening and a second opening, the first opening and the second opening are connected to the first chamber and the second chamber, respectively, and the first opening is positioned on a side closer to the rotation axis than the second opening, wherein the first space includes a first region, which is connected to the first opening and includes a portion extending from the first opening toward a side farther from the rotation axis, wherein the first space of the first chamber has a capacity larger than a capacity of the first flow passages wherein the first flow passage includes a first portion having the first opening and a second portion having the second opening, and wherein the second passage chamber has a capillary force larger than a capillary force of the first portion, and wherein the substrate has a thickness, and the first portion has a depth in a direction of the thickness of the substrate, the second portion has a depth in the direction of the thickness of the substrate, and the depth of the second portion is less than the depth of the first portion.

2. The substrate for sample analysis according to claim 1, wherein the first space further includes a second region connected to the extending portion of the first region at a position farther from the rotation axis than the first opening.

3. The substrate for sample analysis according to claim 1, wherein a part of the first chamber and a part of the first flow passage are positioned in a radial direction with the rotation axis being a center with the first opening interposed therebetween.

4. A substrate for sample analysis, which involves transportation of a liquid through rotational motion, the substrate for sample analysis comprising: a substrate including a rotation axis; a first chamber, which is positioned in the substrate and includes a first space configured to retain the liquid; a second chamber, which is positioned in the substrate and includes a second space configured to retain the liquid discharged from the first chamber: and a first flow passage, which is positioned in the substrate, includes a path configured to connect the first chamber and the second chamber to each other, and is capable of being filled with the liquid retained in the first space through a capillary phenomenon, wherein the first flow passage has a first opening and a second opening, the first opening and the second opening are connected to the first chamber and the second chamber, respectively, and the first opening is positioned on a side closer to the rotation axis than the second opening, wherein the first space includes a first region, which is connected to the first opening and includes a portion extending from the first opening toward a side farther from the rotation axis, wherein the first space of the first chamber has a capacity larger than a capacity of the first flow passage, wherein the first flow passage includes a first portion having the first opening and a second portion having the second opening, and wherein the second portion has a capillary force larger than a capillary force of the first portion, wherein the first flow passage further includes a space adjacent to the first portion and positioned on a side of the rotation axis from the first portion and an opening communicating to the space, and wherein the space is not a capillary path.

5. The substrate for sample analysis according to claim 1, wherein the first region of the first space includes a connecting portion connected to the first opening, and the connecting portion is capable of sucking the liquid retained in the first space through the capillary phenomenon, and
wherein the connecting portion has an opening larger than the first opening in the first region.

6. The substrate for sample analysis according to claim 5, wherein the connecting portion has a thickness smaller than a thickness of the first region in the direction of the thickness of the substrate.

7. The substrate for sample analysis according to claim 2, wherein the extending portion of the first region is capable of sucking the liquid retained in the second region through the capillary phenomenon.

8. The substrate for sample analysis according to claim 1, wherein the first space of the first chamber has a capacity that is twice or more of a capacity of the first flow passage.

9. The substrate for sample analysis according to claim 1, further comprising:
a third chamber, which is positioned farther from the rotation axis than the second chamber in the substrate and includes a third space configured to retain the liquid discharged from the second chamber; and
a second flow passage, which is positioned in the substrate, includes a path configured to connect the second chamber and the third chamber to each other, and is capable of being filled with the liquid retained in the second space through the capillary phenomenon.

10. The substrate for sample analysis according to claim 9, further comprising:
a fourth chamber, which is positioned in the substrate and includes a fourth space configured to retain the liquid; and
another flow passage, which is positioned in the substrate, includes a path configured to connect the fourth chamber and the second chamber to each other, and is capable of being filled with the liquid retained in the fourth space through the capillary phenomenon.

11. The substrate for sample analysis according to claim 10, wherein the first chamber and the fourth chamber are arranged in two regions divided by a straight line connecting a vicinity of a center of the second chamber and the rotation axis to each other in the substrate, respectively.

12. The substrate for sample analysis according to claim 10, wherein both the first chamber and the fourth chamber are arranged in one of two regions divided by a straight line connecting a vicinity of a center of the second chamber and the rotation axis to each other in the substrate.

13. The substrate for sample analysis according to claim 1, further comprising a magnet positioned adjacent to the second chamber.

14. A sample analysis system, comprising:
the substrate for sample analysis of claim 1; and
a sample analysis device comprising:
a motor, which is configured to rotate the substrate for sample analysis about the rotation axis under a state in which the rotation axis is held at an angle of more than 0° and 90° or less with respect to a gravity direction;
a rotation angle detection circuit, which is configured to detect a rotation angle of a rotation axis of the motor;
a drive circuit, which is configured to control the rotation angle of the motor at a time of rotation and stoppage based on a detection result of the rotation angle detection circuit; and
a control circuit, which includes a computing unit, a memory, and a program stored in the memory and configured to be executable by the computing unit, and which is configured to control operations of the motor, the rotation angle detection circuit, and the drive circuit based on the program,
wherein, when the substrate for sample analysis having the first chamber filled with the liquid is mounted to the sample analysis device, the program executes the steps of:
(a) stopping the substrate for sample analysis at a predetermined first angle, to thereby fill the first flow passage with a part of the liquid of the first chamber through the capillary phenomenon; and
(b) rotating the substrate for sample analysis, to thereby transport the part of the liquid in the first flow passage to the second chamber.

15. The sample analysis system according to claim 14, wherein the substrate for sample analysis comprises the substrate for sample analysis of claim 9, and
wherein, after the step (b), the program executes the steps of:
(c) stopping the substrate for sample analysis at a predetermined second angle, to thereby fill the second flow passage with the part of the liquid transported to the second chamber through the capillary phenomenon; and
(d) rotating the substrate for sample analysis, to thereby cause the liquid transported to the second chamber to move to the third chamber through the second flow passage with a centrifugal force.

16. The sample analysis system according to claim 15, wherein, after the step (d), the program executes the steps of:
(e) stopping the substrate for sample analysis at a predetermined third angle, to thereby fill the first flow passage with another part of the liquid in the first chamber through the capillary phenomenon; and
(f) rotating the substrate for sample analysis, to thereby transport the another part of the liquid in the first flow passage to the second chamber.

17. The sample analysis system according to claim 16, wherein, after the step (f), the program executes the steps of:
(g) stopping the substrate for sample analysis at a predetermined fourth angle, to thereby fill the second flow passage with the another part of the liquid transported to the second chamber through the capillary phenomenon; and (h) rotating the substrate for sample analysis, to thereby cause the another part of the liquid transported to the second chamber to move to the third chamber through the second flow passage with the centrifugal force.

18. The sample analysis system according to claim 17, wherein, after the step (h), the program executes the steps of:

(i) stopping the substrate for sample analysis at a predetermined fifth angle, to thereby fill the another flow passage with a part of the liquid in the fourth chamber through the capillary phenomenon; and (j) rotating the substrate for sample analysis, to thereby transport the part of the liquid to the second chamber.

19. The sample analysis system according to claim 18, wherein the sample analysis device further comprises an optical measurement unit, and wherein, after the step (j), the program executes the step of (k) causing the optical measurement unit to perform optical measurement of the liquid transported to the second chamber.

20. The sample analysis system according to claim 14, wherein the program executes the steps (a) and (b) repeatedly twice or more.

21. A sample analysis device, comprising:

a motor, which is configured to rotate the substrate for sample analysis of claim 1 about the rotation axis under a state in which the rotation axis is held at an angle of more than 0° and 90° or less with respect to a gravity direction;

a rotation angle detection circuit, which is configured to detect a rotation angle of a rotation axis of the motor;

a drive circuit, which is configured to control the rotation angle of the motor at a time of rotation and stoppage based on a detection result of the rotation angle detection circuit; and a control circuit, which includes a computing unit, a memory, and a program stored in the memory and configured to be executable by the computing unit, and which is configured to control operations of the motor, the rotation angle detection circuit, and the drive circuit based on the program, wherein, when the substrate for sample analysis having the first chamber filled with the liquid is mounted to the sample analysis device, the program executes the steps of:

(a) stopping the substrate for sample analysis at a predetermined first angle, to thereby fill the first flow passage with a part of the liquid in the first chamber through the capillary phenomenon; and (b) rotating the substrate for sample analysis, to thereby transport the part of the liquid in the first flow passage to the second chamber.

22. A non-transitory computer-readable storage medium storing a program for a sample analysis system, the sample analysis system comprising:

the substrate for sample analysis of claim 1; and a sample analysis device comprising:

a motor, which is configured to rotate the substrate for sample analysis about the rotation axis under a state in which the rotation axis is held at an angle of more than 0° and 90° or less with respect to a gravity direction;

a rotation angle detection circuit, which is configured to detect a rotation angle of a rotation axis of the motor;

a drive circuit, which is configured to control the rotation angle of the motor at a time of rotation and stoppage based on a detection result of the rotation angle detection circuit; and a control circuit, which includes a computing unit, a memory, and a program stored in the memory and configured to be executable by the computing unit, and which is configured to control operations of the motor, the rotation angle detection circuit, and the drive circuit based on the program, wherein, when the substrate for sample analysis having the first chamber filled with the liquid is mounted to the sample analysis device, the program executes the steps of:

(a) stopping the substrate for sample analysis at a predetermined first angle, to thereby fill the first flow passage with a part of the liquid in the first chamber through the capillary phenomenon; and (b) rotating the substrate for sample analysis, to thereby transport the part of the liquid in the first flow passage to the second chamber.

* * * * *